(12) United States Patent
Narayanan et al.

(10) Patent No.: US 12,202,815 B2
(45) Date of Patent: Jan. 21, 2025

(54) SELECTIVE ANDROGEN RECEPTOR DEGRADER (SARD) LIGANDS AND METHODS OF USE THEREOF

(71) Applicant: University of Tennessee Research Foundation, Knoxville, TN (US)

(72) Inventors: Ramesh Narayanan, Tuscaloosa, AL (US); Duane D. Miller, Collierville, TN (US); Yali He, Germantown, TN (US); Dong-Jin Hwang, Arlington, TN (US); Thamarai Ponnusamy, Daejeon (KR)

(73) Assignee: University of Tennessee Research Foundation, Knoxville, TN (US)

( * ) Notice: Subject to any disclaimer, the term of this patent is extended or adjusted under 35 U.S.C. 154(b) by 733 days.

(21) Appl. No.: 17/273,726

(22) PCT Filed: Sep. 5, 2019

(86) PCT No.: PCT/US2019/049769
§ 371 (c)(1),
(2) Date: Mar. 4, 2021

(87) PCT Pub. No.: WO2020/051344
PCT Pub. Date: Mar. 12, 2020

(65) Prior Publication Data
US 2021/0340122 A1 Nov. 4, 2021

Related U.S. Application Data

(60) Provisional application No. 62/727,542, filed on Sep. 5, 2018.

(51) Int. Cl.
*C07D 401/12* (2006.01)
*A61P 5/28* (2006.01)
(Continued)

(52) U.S. Cl.
CPC .............. *C07D 401/12* (2013.01); *A61P 5/28* (2018.01); *A61P 35/00* (2018.01); *C07D 231/16* (2013.01)

(58) Field of Classification Search
CPC ....... C07D 401/12; C07D 231/16; A61P 5/28; A61P 35/00
See application file for complete search history.

(56) References Cited

U.S. PATENT DOCUMENTS 5,480,656 A 1/1996 Okada et al.
5,575,987 A 11/1996 Kamei et al.
(Continued)

FOREIGN PATENT DOCUMENTS

CN 1597662 A 3/2005
CN 102884057 A 1/2013
(Continued)

OTHER PUBLICATIONS

Dörwald, F. Zaragoza. Side Reactions in Organic Synthesis: A Guide to Succesful Synthesis Design, Weinheim: WILEY-VCH Verlg GmbH & Co. KGaA, 2005. (Year: 2005).*
(Continued)

*Primary Examiner* — Matthew P Coughlin
*Assistant Examiner* — Ashli Ariana Chicks
(74) *Attorney, Agent, or Firm* — Knobbe, Martens, Olson & Bear, LLP

(57) ABSTRACT

This invention is directed to selective androgen receptor degrader (SARD) compounds including heterocyclic rings and pharmaceutical compositions and uses thereof in treating prostate cancer, advanced prostate cancer, castration resistant prostate cancer, triple negative breast cancer, other cancers expressing the androgen receptor, androgenic alopecia or other hyperandrogenic dermal diseases, Kennedys disease, amyotrophic lateral sclerosis (ALS), abdominal
(Continued)

aortic aneurysm (AAA), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

27 Claims, 22 Drawing Sheets

(51) Int. Cl.
*A61P 35/00* (2006.01)
*C07D 231/16* (2006.01)

(56) References Cited

U.S. PATENT DOCUMENTS

| | | | |
|---|---|---|---|
| 5,631,020 A | 5/1997 | Okada et al. | |
| 5,643,607 A | 7/1997 | Okada et al. | |
| 5,716,640 A | 2/1998 | Kamei et al. | |
| 5,814,342 A | 9/1998 | Okada et al. | |
| 6,036,976 A | 3/2000 | Takechi et al. | |
| 6,472,415 B1 | 10/2002 | Sovak et al. | |
| 7,022,870 B2 | 4/2006 | Dalton et al. | |
| 7,118,552 B2 | 10/2006 | Shaw et al. | |
| 7,186,854 B2 | 3/2007 | Thijs et al. | |
| 7,220,247 B2 | 5/2007 | Shaw et al. | |
| 7,500,964 B2 | 3/2009 | Shaw et al. | |
| 7,741,371 B2 | 6/2010 | Dalton et al. | |
| 8,735,440 B2 | 5/2014 | McKnight et al. | |
| 9,550,742 B2 | 1/2017 | Marugan et al. | |
| 9,814,698 B2 | 11/2017 | Narayanan et al. | |
| 9,815,776 B2 | 11/2017 | Narayanan et al. | |
| 9,834,507 B2 | 12/2017 | Narayanan et al. | |
| 10,017,471 B2 | 7/2018 | Narayanan et al. | |
| 10,035,763 B2 | 7/2018 | Narayanan et al. | |
| 10,093,613 B2 | 10/2018 | Narayanan et al. | |
| 10,441,570 B2 | 10/2019 | Narayanan et al. | |
| 10,597,354 B2 | 3/2020 | Narayanan et al. | |
| 10,654,809 B2 * | 5/2020 | Narayanan | C07C 255/60 |
| 10,806,719 B2 * | 10/2020 | Narayanan | C07C 317/46 |
| 10,806,720 B2 | 10/2020 | Narayanan et al. | |
| 10,865,184 B2 * | 12/2020 | Narayanan | C07D 217/04 |
| 11,230,523 B2 * | 1/2022 | Narayanan | C07D 239/74 |
| 11,230,531 B2 | 1/2022 | Narayanan et al. | |
| 11,873,282 B2 * | 1/2024 | Narayanan | C07D 235/06 |
| 2005/0101657 A1 | 5/2005 | Furuya et al. | |
| 2006/0142387 A1 | 6/2006 | Cadilla et al. | |
| 2006/0160845 A1 | 7/2006 | Schlienger et al. | |
| 2006/0173037 A1 | 8/2006 | Schlienger et al. | |
| 2006/0241180 A1 | 10/2006 | Dalton et al. | |
| 2007/0049629 A1 | 3/2007 | Scanlan et al. | |
| 2007/0123512 A1 | 5/2007 | Ratilainen | |
| 2007/0123563 A1 | 5/2007 | Dalton et al. | |
| 2007/0173546 A1 | 7/2007 | Dalton et al. | |
| 2007/0265290 A1 | 11/2007 | Dalton et al. | |
| 2008/0293766 A1 | 11/2008 | Diamond et al. | |
| 2009/0042844 A1 | 2/2009 | Labrie et al. | |
| 2009/0060873 A1 | 3/2009 | Sporn et al. | |
| 2009/0142323 A1 | 6/2009 | Quarles et al. | |
| 2010/0227846 A1 | 9/2010 | Ito et al. | |
| 2010/0331418 A1 | 12/2010 | Koh et al. | |
| 2011/0028719 A1 | 2/2011 | Slon-Usakiewicz | |
| 2013/0116258 A1 | 5/2013 | Smith et al. | |
| 2013/0253035 A1 | 9/2013 | Mcdonnell et al. | |
| 2014/0018433 A1 | 1/2014 | Dalton et al. | |
| 2014/0094474 A1 | 4/2014 | Törmakängas et al. | |
| 2016/0264540 A1 | 9/2016 | Wipf et al. | |
| 2017/0095446 A1 | 4/2017 | Narayanan et al. | |
| 2017/0368003 A1 | 12/2017 | Narayanan et al. | |
| 2018/0028521 A1 | 2/2018 | Gottardis et al. | |
| 2018/0271849 A1 | 9/2018 | Ge et al. | |
| 2020/0222365 A1 | 7/2020 | Narayanan et al. | |
| 2021/0024458 A1 | 1/2021 | Ponnusamy et al. | |
| 2021/0161864 A1 | 6/2021 | Miller et al. | |
| 2021/0196678 A1 | 7/2021 | Narayanan et al. | |
| 2021/0253525 A1 | 8/2021 | Narayanan et al. | |

FOREIGN PATENT DOCUMENTS

| | | | |
|---|---|---|---|
| CN | 106551934 A | 9/2016 | |
| EP | 0253503 | 1/1988 | |
| EP | 0524781 A1 | 1/1993 | |
| EP | 100172 A1 | 2/2004 | |
| EP | 2159049 A1 | 3/2010 | |
| JP | 2008526888 A | 7/2008 | |
| WO | WO 2001/058855 A1 | 8/2001 | |
| WO | WO 2002/016310 A1 | 2/2002 | |
| WO | WO 2002/046164 A1 | 6/2002 | |
| WO | WO2002098878 * | 12/2002 | A61P 25/28 |
| WO | WO 2003/074473 A2 | 9/2003 | |
| WO | WO 2003/106401 A1 | 12/2003 | |
| WO | WO 2004/035737 A2 | 4/2004 | |
| WO | WO 2004/035738 A2 | 4/2004 | |
| WO | WO 2005000794 A1 | 1/2005 | |
| WO | WO 2005/094531 A2 | 10/2005 | |
| WO | WO 2005/120477 A2 | 12/2005 | |
| WO | WO 2006/014420 A1 | 2/2006 | |
| WO | WO 2006-044359 A2 | 4/2006 | |
| WO | WO 2007/005887 A2 | 1/2007 | |
| WO | WO 2007/126988 A2 | 11/2007 | |
| WO | WO 2008/011072 A2 | 1/2008 | |
| WO | WO 2008/044033 A1 | 4/2008 | |
| WO | WO 2008/076918 A2 | 6/2008 | |
| WO | WO 2008/124000 A2 | 10/2008 | |
| WO | WO 2008/137038 A1 | 11/2008 | |
| WO | WO 2009/010480 A1 | 1/2009 | |
| WO | WO 2009/069736 A1 | 6/2009 | |
| WO | WO 2009/082437 A2 | 7/2009 | |
| WO | WO 2012/007644 A1 | 1/2012 | |
| WO | WO 2013/064681 A1 | 5/2013 | |
| WO | WO 2014/113260 A1 | 7/2014 | |
| WO | WO 2015/042297 A1 | 3/2015 | |
| WO | WO 2017/214634 A1 | 12/2017 | |

OTHER PUBLICATIONS

Patani et al. Chem. Rev. 1996, 96, 3147-3176 (Year: 1996).*
Sheridan, R.P. J. Chem. Inf. Comput. Sci. 2002, 42, 103-108 (Year: 2002).*
Andersen et al., "Regression of castrate-recurrent prostate cancer by a small-molecule inhibitor of the amino-terminus domain of the androgen receptor," Cancer cell, Jun. 15, 2010; 17(6): 535-546.
Antonarakis et al., "AR-V7 and resistance to enzalutamide and abiraterone in prostate cancer," New England Journal of Medicine, Sep. 11, 2014; 371(11): 1028-1038.
Aradi et al., "DFTB+, a sparse matrix-based implementation of the DFTB method", J Phys Chem. A. Jul. 5, 2007;111(26): 5678-5684.
Attard et al., "Selective inhibition of CYP17 with abiraterone acetate is highly active in the treatment of castration-resistant prostate cancer," Journal of clinical oncology, May 26, 2009; 27(23); 3742-3748.
Baek et al., "Ligand-specific allosteric regulation of coactivator functions of androgen receptor in prostate cancer cells" Proceedings of the National Academy of Sciences of the United States of America, Feb. 28, 2006; 103(9); 3100-3105.
Bassetto et al., "Design and synthesis of novel bicalutamide and enzalutamide derivatives as antiproliferative agents for the treatment of prostate cancer", Eur J Med Chem. Aug. 8, 2016;118: 230-243.
Berrevoets et al., "Effects of antiandrogens on transformation and transcription activation of wild-type and mutated (LNCaP) androgen receptors," The Journal of steroid biochemistry and molecular biology, Dec. 31, 1993; 46(6): 731-736.
Bohl et al., "Structural basis for antagonism and resistance of bicalutamide in prostate cancer," Proceedings of the National Academy of Sciences, Apr. 26, 2005; 102(17): 6201-6206.
Bohl et al., "A ligand-based approach to identify quantitative structure-activity relationships for the androgen receptor," J Med Chem., Jul. 15, 2004; 47(15): 3765-3776.

(56) References Cited

OTHER PUBLICATIONS

Bohl et al., "Structural basis for accommodation of nonsteroidal ligands in the androgen receptor," J Biol. Chem., Nov. 11, 2005; 280(45): 37747-37754.
Bratenko et al., "Polyfunctional pyrazoles. 3 .* Synthesis of 3-(3-aryl-4-formyl-1-pyrazolyl) propionic acids and their amides", Chem Heter Compounds. Oct. 2004;40(10): 1279-1282.
CAS Registry No. 55734-18-4; STN Entry Date: Nov. 16, 1984.
CAS Registry No. 945553-38-8; STN Entry Date: Aug. 24, 2007.
CAS Registry No. 1349723-51-8; STN Entry Date: Dec. 6, 2011.
CAS Registry No. 1480139-15-8; STN Entry Date: Nov. 24, 2013.
CAS Registry No. 1526624-00-9; STN Entry Date: Jan. 21, 2014.
CAS Registry No. 1839720-91-0; STN Entry Date: Jan. 1, 2016.
CAS Registry No. 1919463-97-0; STN Entry Date: May 27, 2016.
CAS Registry No. 1928217-46-2; STN Entry Date: Nov. 16, 2016.
Choi et al., "Collision tumor of hepatocellular carcinoma and neuroendocrine carcinoma involving the liver: case report and review of the literature", World J Gastroenterol. Nov. 7, 2016;22(41): 9229-9234.
Claessens et al., "Diverse roles of androgen receptor (AR) domains in AR-mediated signaling," J Nucl Recep Signal. Jun. 27, 2008; 6:e008 in 13 pages.
Clegg et al., "ARN-509: A novel antiandrogen for prostate cancer treatment," Cancer Res., Mar. 15, 2012; 72(6): 1494-1503.
ClinicalTrials.gov; "Enzalutamide in patients with androgen receptor positive (AR+) ovarian, primary peritoneal or fallopian tube cancer and one, two or three prior therapies", Study Sponsor: Memorial Sloan Kettering Cancer Center/Medivation, Inc., received: Oct. 25, 2013; last update: Jun. 2017 in 6 pages.
Colin et al., "New Access to fluorinated ketoglycolic acid derivatives from trifluoropyruvamides", Tetrahe Letts. Jul. 12, 2004;45(29): 5611-5613.
Dalvit et al., "Identification of compounds with binding affinity to proteins via magnetization transfer from bulk water", J Biomolecular NMR. Sep. 2000;18(1): 65-68.
Danquah et al., "Combination therapy of antiandrogen and XIAP inhibitor for treating advanced prostate cancer," Pharma Res., Aug. 1, 2012; 29(8): 2079-2091.
DATABASE Caplus Chemical Abstracts Service; Database Accession No. 2005: 14358, Abstract of WO 2005000794, published, Jan. 6, 2005; in 9 pages.
De Bono et al., "Abiraterone and increased survival in metastatic prostate cancer," N Eng J Med., May 26, 2011; 364(21): 1995-2005.
Dehm et al., "Alternatively spliced androgen receptor variants," Endocrine-related Cancer, Oct. 1, 2011; 18(5): R183-R196.
Dehm et al., "Splicing of a novel androgen receptor exon generates a constitutively active androgen receptor that mediates prostate cancer therapy resistance," Cancer Res., Jul. 1, 2008; 68(13): 5469-5477.
Dias et al., "NMR approaches in structure-based lead discovery: recent developments and new frontiers for targeting multi-protein complexes", Prog Biophys Mol Biol. Nov. 1, 2014;116(2-3): 101-112.
Duke III, Charles B., et al., "Synthesis and biological studies of androgen receptor ligands: Towards mutation-resistant nonsteroidal antagonism," Abstract of Papers of the American Chemical Society, vol. 240, 1155; 16th St, NW, Washington, DC 20036 USA: Amer Chem Soc, 2010; 1 page.
Elstner et al., "Self-consistent-charge density-functional tight-binding method for simulations of complex materials properties", Phys Rev B. Sep. 15, 1998;58(11): 7260-7268.
Epps et al., "Determination of the affinity of drugs toward serum albumin by measurement of the quenching of the intrinsic tryptophan fluorescence of the protein", J Pharm Pharmacol. Jan. 1999;51(1): 41-48.
Gal et al., "Efficient isothermal titration calorimetry technique identifies direct interation of small molecule inhibitors with the target protein", Combin Chem High Throughput Screen. Jan. 1, 2016;19(1): 4-13.

Gibson et al., "Evidence of androgen action in endometrial and ovarian cancers", Endocrine-related cancer. Aug. 1, 2014;21(4): T203-T218.
Gottlieb et al., "Androgen insensitivity syndrome", University of Washington, Seattle (WA) Publication, initial Posting: Mar. 24, 1999; last Update: May 11, 2017, in 15 pages.
Hara et al., "Novel mutations of androgen receptor: a possible mechanism of bicalutamide withdrawal syndrome", Cancer Res. Jan. 1, 2003;63(1): 149-153.
He et al., "ASC-J9 suppresses renal cell carcinoma progression by targeting an androgen receptor-dependent HIF2α/VEGF Signaling Pathway", Cancer Res. Aug. 2014.; 74(16): 4420-4430.
Hebenbrock K-F., "Preparation and reaction of 1-aryl-3-hydroxy-3-methyl-2,5-pyrrolidinediones", Justus Liebig's Annals of Chemistry, Aug. 1, 1978;vol. 2, pp. 320-336 (Abstract).
Hu et al., "Distinct transcriptional programs mediated by the ligand-dependent full-length androgen receptor and its splice variants in castration-resistant prostate cancer," Cancer Res., Jul. 15, 2012; 72(14): 3457-3462.
Hwang et al., "Arylisothiocyanato selective androgen receptor modulators (SARMs) for prostate cancer," Bioorg Med Chem., Oct. 1, 2006; 14(19): 6525-6538.
Isikbay et al., "Glucocorticoid receptor activity contributes to resistance to androgen-targeted therapy in prostate cancer", Horm Cancer. Apr. 2014;5(2): 72-89.
Jin et al., "Synthesis and biological evaluation of 1-substituted-3(5)-(6-methylpyridin-2-yl)-4-(quinoxalin-6-yl)pyrazoles as transforming growth factor-ß type 1 receptor kinase inhibitors," Euro J Med Chem. (2011)46: 3917-3925.
Jin et al., "Synthesis and biological evaluation of 1-substituted-3(5)-(6-methylpyridin-2-yl)-4-(quinolin-6-yl)pyrazoles as transforming growth factor-ß type 1 receptor kinase inhibitors", Bioorg Med Chem. 2011;19: 2633-2640.
Kamal et al., "Androgen receptors are acquired by healthy postmenopausal endometrial epithelium and their subsequent loss in endometrial cancer is associated with poor survival", Br J Cancer. Mar. 2016;114(6): 688-696.
Kim et al., "Ribosomal proteins as unrevealed caretakers for cellular stress and genomic instability," Oncotarget, Feb. 1, 2014; 5(4): 860-71.
Klotz L., "Maximal androgen blockade for advanced prostate cancer," Best Pract Res Clin Endocrin Metabol., Apr. 30, 2008; 22(2): 331-340.
Kominea et al., "Androgen receptor (AR) expression is an independent unfavorable prognostic factor in gastric cancer", J Cancer Res Clin Oncol. May 2004;130(5): 253-258.
La Spada et al., "Androgen receptor gene mutations in X-linked spinal and bulbar muscular atrophy", Nature. Jul. 1991;352(6330): 77-79.
Lazar et al., "Hyperandrogenism as a cause of early polycystic ovary syndrome (PCOS) in girls with central precocious puberty (CPP)", Pediatric Research. May 1993;33(5): S14; Abstract 64.
Li et al., "On the physical origin of blue-shifted hydrogen bonds", J Am Chem Soc. Aug. 14, 2002;124(32): 9639-9647.
Li et al., "Androgen receptor splice variants mediate enzalutamide resistance in castration-resistant prostate cancer cell lines," Cancer Res., Jan. 15, 2012; 73(2): 483-489.
Lieberman et al., [Eds.] Pharmaceutical Dosage Forms: Tablets; Marcel Dekker, 1989, TOC in 11 pages.
Maclean et al., "Spinal and bulbar muscular atrophy: androgen receptor dysfunction caused by a trinucleotide repeat expansion," Journal of the neurological sciences, Feb. 29, 1996; 135(2): 149-57.
Marhefka et al., "Homology modeling using multiple molecular dynamics simulations and docking studies of the human androgen receptor ligand binding domain bound to testosterone and nonsteroidal ligands," J Med Chem., May 24, 2001; 44(11): 1729-1740.
Marhefka et al., "Design, synthesis, and biological characterization of metabolically stable selective androgen receptor modulators," J Med Chem., Feb. 12, 2004; 47(4): 993-998.
Mayo Clinic, "Uterine Fibroids - Overview", Mayo Clinic Staff; printed Aug. 7, 2017; 2 pages.
McGinley et al., "Circumventing anti-androgen resistance by molecular design," J Am Chem Soc., Apr. 4, 2007; 129(13): 3822-3823.

(56) References Cited

OTHER PUBLICATIONS

Mikkonen et al., "Androgen receptor and androgen-dependent gene expression in lung", Mol Cell Endocrinol. Apr. 12, 2010;317(1-2): 14-24.
Miller D.D., "Irreversible Nonsteroida SARMs for Prostate Cancer", Aug. 15, 2003;online at http://grantome.com/grant/NIH/R01-DK065227-20, 2003, 4 pages.
Mitsiades N., "A road map to comprehensive androgen receptor axis targeting for castration-resistant prostate cancer," Cancer Res., Aug. 1, 2013; 73(15): 4599-4605.
Mohler et al., "Nonsteroidal selective androgen receptor modulators (SARMs): Dissociating the anabolic and androgenic activities of the androgen receptor for therapeutic benefit", J Med Chem., Jun. 2009;52(12): 3597-3617.
Mohler et al., "Androgen receptor antagonists: a patent review (2008-2011)," Expert Opinion Ther. Patents, (2012): 22(5): 541-565.
Monge et al., "Unfaithfulness and promiscuity of a mutant androgen receptor in a hormone-refractory prostate cancer," Cell Mol Life Sci., Feb. 1, 2006; 63(4): 487-497.
Morris et al., "Non-steroidal antiandrogens. Design of novel compounds based on an infrared study of the dominant conformation and hydrogen-bonding properties of a series of anilide antiandrogens", J Med Chem. Jan. 1991;34(1): 447-455.
Morvillo et al., "Androgen receptors in human melonoma cell lines IIB-MEL-LES and IIB-MEL-IAN and in human melanoma metastases", Melanomoa Res. Dec. 2002;12(6): 529-538 [Abstract].
Mostaghel et al., "Androgen receptor expression in mantle cell lymphoma: Potential novel therapeutic implications", Exp Hematol. May 2017;49: 34-38.e2.
Munoz et al., "Androgen receptors beyond prostate cancer: An old marker as a new target", Oncotarget. Jan. 2015;6(2): 592-603.
Nagata et al., "Preparation and reactions of cyclic a-monocarbonyl azo-compounds: 1-pyrazolin-3-one derivatives", J Chem Soc. C: Organic. 1970(4): 540-550.
Narayanan et al., "Biological synthesis of metal nanoparticles by microbes", Adv Colloid Interface Science. Apr. 22, 2010;156(1-2): 1-3.
Narayanan et al., "Selective Androgen Receptor Modulators (SARMs) Negatively Regulate Triple-Negative Breast Cancer Growth and Epithelial: Mesenchymal Stem Cell Signaling," PLOS ONE, Jul. 2014; 9(7): 1-12.
Nazareth et al., "Activation of the human androgen receptor through a protein kinase A signaling pathway," J Biol Chem., Aug. 16, 1996; 271(33): 19900-19907.
Nyquist et al., "TALEN-engineered AR gene rearrangements reveal endocrine uncoupling of androgen receptor in prostate cancer," Proc Nat Acad. Sci., Oct. 22, 2013; 110(43): 17492-17497.
Park et al., "Expression of DBC1 and androgen receptor predict poor prognosis in diffuse large B cell lymphoma", Transl Oncol. Jun. 1, 2013;6(3): 370-381.
Ponnusamy et al., "Novel Selective Agents for the Degradation of Androgen Receptor Variants to Treat Castration-Resistant Prostate Cancer," Cancer Res. (2017); 77(22): 6282-6298.
Pubchem, CID 3145286.09, Aug. 9, 2005, pp. 1-12; retrieved from the Internet <URL: https:Ilpubchem.ncbl.nlm.nih.gov/compound/3145286> in 12 pages.
Pubmed, CID 20221988, "Compound Summary for CID 20221988-C12H13N30"; Dec. 5, 2007, pp. 1-11; retrieved from the Internet <URL: https://pubchem.ncbi.nlm.nih.gov/compound/20221988>.
Rawel et al., "Determining the binding affinities of phenolic compounds to proteins by quenching of the intrinsic tryptophan fluorescence", Mol Nutri Food Res. Aug. 2006;50(8): 705-713.
Gennaro A.R. [Ed.], "Remington's pharmaceutical sciences", Mack Publishing Company, 18th Edition; 1990, TOC in 6 pages.
Rowe R.C. [Ed.], "Handbook Of Pharmaceutical Excipients", American Pharmaceutical Association; Fifth Edition, 2006, TOC in 6 pages.
Rygula et al., "Raman spectroscopy of proteins: a review", J Raman Spectrosc. Aug. 2013;44(8): 1061-1076.

Sadar M.D., "Androgen-independent induction of prostate-specific antigen gene expression via cross-talk between the androgen receptor and protein kinase a signal transduction pathways," J Biol Chem., Mar. 19, 1999; 274(12): 7777-7783.
Sadar et al., "Ligand-independent activation of the androgen receptor by the differentiation agent butyrate in human prostate cancer cells," Cancer Res., Oct. 15, 2000; 60(20): 5825-5831.
Sartor et al., "Androgen receptor variant-7: an important predictive biomarker in castrate resistant prostate cancer," Asian J Andrology, May 2015; 17(3): 439-440.
Scher et al., "Increased survival with enzalutamide in prostate cancer after chemotherapy," N Eng J Med., Sep. 27, 2012; 367(13): 1187-1197.
Schragl et al., "Novel pathway for the synthesis of arylpropionamide-derived selective androgen receptor modulator (SARM) metabolites of andarine and ostarine", Tetra Lettrs. May 1, 2013;54(18): 2239-2242.
Seligson et al., "Development of Fluridil, a topical suppressor of the androgen receptor in androgenetic alopecia", Drug Devel Res. Jul. 2003;59(3): 292-306.
Shortridge et al., "Estimating protein-ligand binding affinity using high-throughput screening by NMR", J Comb Chem. Nov. 10, 2008;10(6): 948-958.
Sieber PR., "Treatment of bicalutamide-induced breast events," Exp Review Anticancer Thera., Dec. 1, 2007; 7(12): 1773-1779.
Siegel et al., "Cancer statistics, 2014" CA Cancer. J. Clin., 2014; 64: 9-29.
Simanainen et al., "Androgen receptor actions modify skin structure and chemical carcinogen-induced skin cancer susceptibility in mice", Hormones and Cancer. Feb. 2015;6(1): 45-53.
Soper et al., "Definitive treatment of androgen receptor-positive salivary duct carcinoma with androgen deprivation therapy and external beam radiotherapy", Head Neck. Jan. 2014;36(1): E4-E7.
Sukocheva et al., "Androgens and esophageal cancer: What do we know?" World J Gastroenterol. May 28, 2015;21(20): 6146-6156.
Tan et al., "Dehydroepiandrosterone activates mutant androgen receptors expressed in the androgen-dependent human prostate cancer xenograft CWR22 and LNCaP cells", Mol Endocrin. Apr. 1, 1997;11(4): 450-459.
Tangen et al., "Androgen receptor as potential therapeutic target in metastatic endometrial cancer", Oncotarget. Aug. 2, 2016;7(31): 49289-49298.
Tarikogullari et al., "Synthesis and anticonvulsant activity of some alkanamide derivatives", Arzneimittelforschung. Oct. 2010;60(10): 593-598 (Abstract).
Tran et al., "Development of a second-generation antiandrogen for treatment of advanced prostate cancer," Science, May 8, 2009; 324(5928): 787-790.
Tucker et al., "Nonsteroidal antiandrogens. Synthesis and structure-activity relationships of 3-substituted derivatives of 2-hydroxypropionanilides", J Med Chem. May 1988;31(5): 954-959.
Tutton et al., "The influence of androgens, anti-androgens, and castration on cell proliferation in the jejunal and colonic crypt epithelia, and in dimehylhydrazine-induced adenocarcinoma of rat colon", Virchows Arch B Cell Pathol Incl Mol Pathol. 1982;38(3): 351-356 [Abstract].
Ueda et al., "Ligand-independent activation of the androgen receptor by interleukin-6 and the role of steroid receptor coactivator-1 in prostate cancer cells," J Biol Chem., Oct. 11, 2002; 277(41): 38087-38094.
Wang et al., "Small molecule inhibition of the steroid receptor coactivators, SRC-3 and SRC-1", Mol Endocrin. Dec. 1, 2011;25(12): 2041-2053.
Wang et al., "Effects of hydrogen bond and solvent polarity on the C=O stretching of bis (2-thienyl)ketone in solution", J Chem Physics. Mar. 28, 2012;136(12): 03B614.
Watson et al., "Constitutively active androgen receptor splice variants expressed in castration-resistant prostate cancer require full-length androgen receptor", PNAS. Sep. 28, 2010;107(39): 16759-16765.

(56) References Cited

OTHER PUBLICATIONS

Weiner L.P., "Possible role of androgen receptors in amyotrophic lateral sclerosis: a hypothesis," Arch Neurol. Mar. 1, 1980; 37(3): 129-131 (Abstract).
Wen et al., "LHRH-conjugated micelles for targeted delivery of antiandrogen to treat advanced prostate cancer," Pharma Res., Oct. 1, 2014; 31(10): 2784-2795.
Wen et al., "Targeting fatty acid synthase with ASC-J9 suppresses proliferation and invasion of prostate cancer cells", Mol Carcino. Dec. 2016;55(12): 2278-2290.
West A.R., "Solid state chemistry and its applications", John Wiley & Sons; 1988; Chapter 10; pp. 358, 365.
Wikipedia, "Hyperandrogenism", downloaded Aug. 7, 2017 in 8 pages.
Wong et al., "Circulating sex hormones and risk of uterine fibroids: Study of women's health across the nation (SWAN)," J Clin Endocrinol. Jan. 1, 2016;101(1): 123-130.
Xu et al., "hSSB1 binds and protects p21 from ubiquitin-mediated degradation and positively correlates with p21 in human hepatocellular carcinomas," Oncogene, May 12, 2011; 30(19): 2219-29.
Yamashita et al., "ASC-J9 suppresses castration-resistant prostate cancer growth through degradation of full-length and splice variant androgen receptors," Neoplasia, Jan. 1, 2012;14(1): 74-83.
Yepuru et al., "Steroidogenic enzyme AKR1C3 is a novel androgen receptor-selective coactivator that promotes prostate cancer growth", Clin Cancer Res. Oct. 15, 2013;19(20): 5613-5625.
Yoshida et al., "Antiandrogen bicalutamide promotes tumor growth in a novel androgen-dependent prostate cancer xenograft model derived from a bicalutamide-treated patient," Cancer Res., Nov. 1, 2005; 65(21): 9611-9616.
Yu et al., "Androgen receptor signaling regulates growth of glioblastoma multiforme in men", Tumour Biol. Feb. 2015;36(2): 967-972 [Abstract].
Zhou et al., "Study of the impact of the T877A mutation on ligand-induced helix-12 positioning of the androgen receptor resulted in design and synthesis of novel antiandrogens," Proteins: Structure, Function, and Bioinformatics, Feb. 15, 2010; 78(3): 623-37.
International Search Report dated Dec. 24, 2019.
Aggarwal, et al. "Androgens affect muscle, motor neuron, and survival in a mouse model of SOD1-related amyotrophic lateral sclerosis." Neurobiology of Aging 35.8 (2014): 1929-1938.
Antonarakis, et al., "Clinical significance of androgen receptor splice variant-7 mRNA detection in circulating tumor cells of men with metastatic castration-resistant prostate cancer treated with first-and second-line abiraterone and enzalutamide." J Clin Oncol 35.19 (2017): 2149-2156. doi: 10.1200/JCO.2016.70.1961.
Arora, et al. "Glucocorticoid receptor confers resistance to antiandrogens by bypassing androgen receptor blockade." Cell 155.6 (2013): 1309-1322.
Baniahmad, Aria. "Inhibition of the androgen receptor by antiandrogens in spinobulbar muscle atrophy." Journal of Molecular Neuroscience 58.3 (2016): 343-347.
Bryce, et al., "Androgen receptor splice variant 7 in castration-resistant prostate cancer: Clinical considerations." International Journal of Urology 23.8 (2016): 646-653. doi: 10.1111/iju.13134.
Cochrane et al., Role of the androgen receptor in breast cancer and preclinical analysis of enzalutamide., Breast Cancer Res. (2014) 16(1): R7, pp. 1-19.
Davis, et al. "Pharmacologic blockade and genetic deletion of androgen receptor attenuates aortic aneurysm formation." Journal of vascular surgery 63.6 (2016): 1602-1612.
Galbiati, et al. "The anabolic/androgenic steroid nandrolone exacerbates gene expression modifications induced by mutant SOD1 in muscles of mice models of amyotrophic lateral sclerosis." Pharmacological research 65.2 (2012): 221-230.
Hsieh, et al. "Androgen receptor trinucleotide polymorphism in leiomyoma." Journal of assisted reproduction and genetics 21.12 (2004): 453-457.
International Preliminary Report on Patentability from PCT/US2019/049769 dated Mar. 18, 2021.
Joseph, et al. "A clinically relevant androgen receptor mutation confers resistance to second-generation antiandrogens enzalutamide and ARN-509." Cancer discovery 3.9 (2013): 1020-1029.
Kanda et al. "Androgen receptor signaling in hepatocellular carcinoma and pancreatic cancers"., World J. Gastroenterology Jul. 2014, 20(29), 9229-9236.
Kawahara, et al. "ELK1 is up-regulated by androgen in bladder cancer cells and promotes tumor progression." Oncotarget 6.30 (2015): 29860-29876.
Lallous, et al. "Functional analysis of androgen receptor mutations that confer anti-androgen resistance identified in circulating cell-free DNA from prostate cancer patients." Genome biology 17.1 (2016): 1-15.
Lieberman, et al. "Peripheral androgen receptor gene suppression rescues disease in mouse models of spinal and bulbar muscular atrophy." Cell reports 7.3 (2014): 774-784.
Locati, et al. "Clinical activity of androgen deprivation therapy in patients with metastatic/relapsed androgen receptor-positive salivary gland cancers." Head & neck 38.5 (2016): 724-731.
McBeth et al., "Involvement of the Androgen and Glucocorticoid Receptors in Bladder Cancer". International journal of endocrinology 2015 (2015), pp. 1-11. Article ID 384860.
Miller, et al. "Phase III, randomized, placebo-controlled study of once-daily oral zibotentan (ZD4054) in patients with non-metastatic castration-resistant prostate cancer." Prostate cancer and prostatic diseases 16.2 (2013): 187-192.
Renier, et al. "Antiandrogen flutamide protects male mice from androgen-dependent toxicity in three models of spinal bulbar muscular atrophy." Endocrinology 155.7 (2014): 2624-2634.
Rosa, et al. "Polymorphisms of CYP17A1, CYP19, and androgen in Brazilian women with uterine leiomyomas." Clinical Chemistry and Laboratory Medicine (CCLM) 46.6 (2008): 814-823.
Sun et al. "Castration resistance in human prostate cancer is conferred by a frequently occurring androgen receptor splice variant." The Journal of clinical investigation 120.8 (2010): 2715-2730.

* cited by examiner

|  | 1002 | Enza | 1049 | 1066 | 1065 |
|---|---|---|---|---|---|
| P from veh. | 0.026 | 0.0027 | 0.024 | N.S. | <0.0001 |

|  | 1002 | Enza | 1049 | 1066 | 1065 |
|---|---|---|---|---|---|
| P from veh. | 0.026 | 0.0027 | 0.024 | N.S. | <0.0001 |

| | 1065 | | | | 1048 | |
|---|---|---|---|---|---|---|
| Groups | 1 | 5 | 10 | 20 | 1 | 5 |
| p Value | Not significant (N.S.) | N.S. | N.S. | N.S. | N.S. | <0.001 |

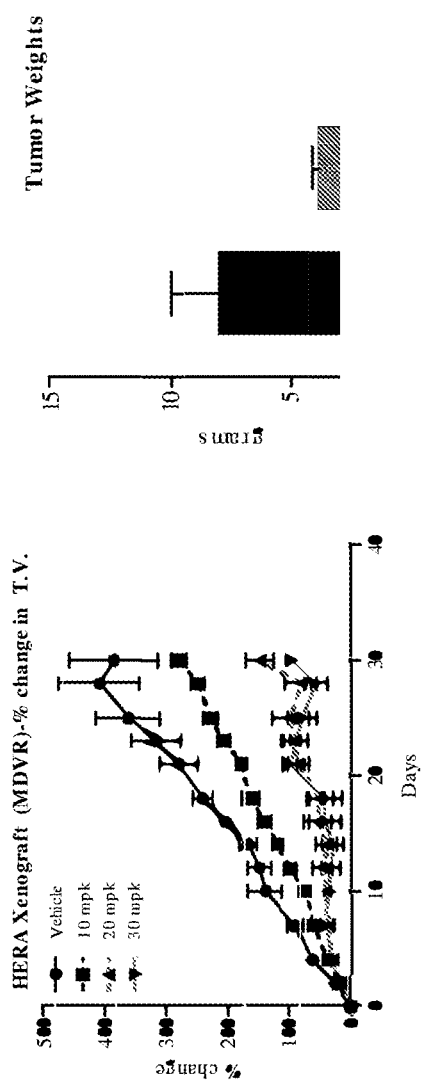
Figure 13A
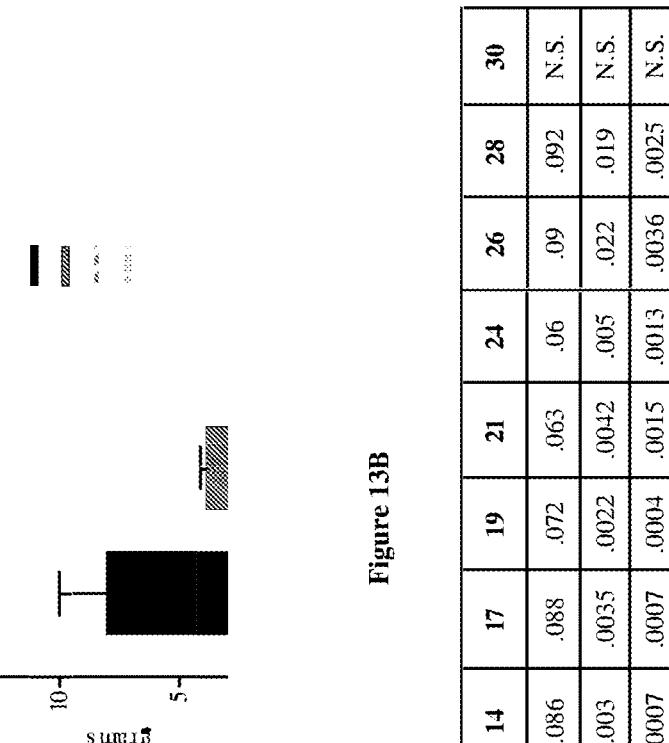
Figure 13B
| Group/Days | 0 | 3 | 5 | 7 | 10 | 12 | 14 | 17 | 19 | 21 | 24 | 26 | 28 | 30 |
|---|---|---|---|---|---|---|---|---|---|---|---|---|---|---|
| G2 (10 mg/kg) | .87 | .58 | .053 | .17 | .07 | .07 | .086 | .088 | .072 | .063 | .06 | .09 | .092 | N.S. |
| G3 (20 mg/kg) | .73 | .28 | .03 | .019 | .012 | .0061 | .003 | .0035 | .0022 | .0042 | .005 | .022 | .019 | N.S. |
| G4 (30 mg/kg) | .80 | .19 | .008 | .008 | .0025 | .0007 | .0007 | .0007 | .0004 | .0015 | .0013 | .0036 | .0025 | N.S. |
Figure 13C

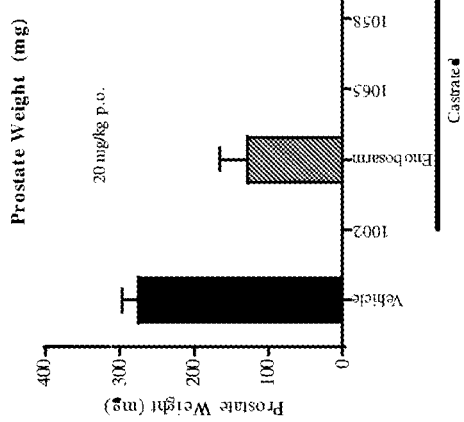
Figure 15A
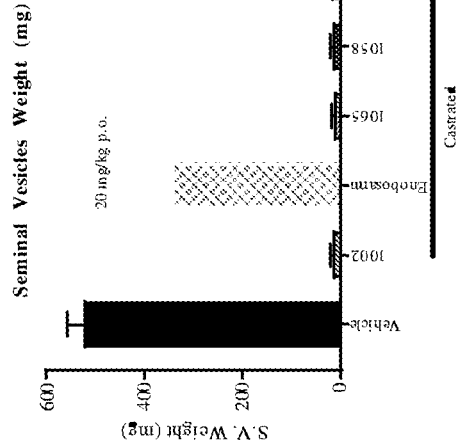
Figure 15B
| Groups | Treatment (20 mg/kg) | Prostate (mg) | S.V. (mg) |
|---|---|---|---|
| 1 | Intact Vehicle | 277.6 ± 9.95 | 524.6 ± 16.8 |
| 2 | 1002 | 0 ± 0 | 15.4 ± 1.3 |
| 3 | Enobosarm | 131 ± 17.5 | 344.7 ± 24.4 |
| 4 | 1065 | 0 ± 0 | 12.7 ± 1.6 |
| 5 | 1058 | 0 ± 0 | 15.7 ± 1.2 |
| 6 | Castrated Vehicle | 11.7 ± 1.04 | 18.3 ± 1.2 |
Figure 15C

SELECTIVE ANDROGEN RECEPTOR DEGRADER (SARD) LIGANDS AND METHODS OF USE THEREOF

CROSS-REFERENCE TO RELATED APPLICATIONS

This application is a National Phase Application of PCT International Application No. PCT/US2019/049769, filed Sep. 5, 2019, which claims the benefit of U.S. Provisional Patent Application Ser. No. 62/727,542, filed Sep. 5, 2018, both of which are hereby incorporated by reference in their entirety.

FIELD OF THE INVENTION

This invention is directed to selective androgen receptor degrader (SARD) compounds including heterocyclic rings and pharmaceutical compositions and uses thereof in treating prostate cancer, advanced prostate cancer, castration resistant prostate cancer, triple negative breast cancer, other cancers expressing the androgen receptor, androgenic alopecia or other hyperandrogenic dermal diseases, Kennedy's disease, amyotrophic lateral sclerosis (ALS), abdominal aortic aneurysm (AAA), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

BACKGROUND OF THE INVENTION

Prostate cancer (PCa) is one of the most frequently diagnosed noncutaneous cancers among men in the US and is the second most common cause of cancer deaths with more than 200,000 new cases and over 30,000 deaths each year in the United States. PCa therapeutics market is growing at an annual rate of 15-20% globally.

Androgen-deprivation therapy (ADT) is the standard of treatment for advanced PCa. Patients with advanced prostate cancer undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

Patients with CRPC have a median survival of 12-18 months. Though castration-resistant, CRPC is still dependent on the androgen receptor (AR) signaling axis for continued growth. The primary reason for CRPC re-emergence is re-activation of AR by alternate mechanisms such as: 1) intracrine androgen synthesis, 2) AR splice variants (AR-SV), e.g., that lack ligand binding domain (LBD), 3) AR-LBD mutations with potential to resist AR antagonists (i.e., mutants that are not sensitive to inhibition by AR antagonists, and in some cases AR antagonists act as agonists of the AR bearing these LBD mutations), and 4) amplifications of the AR gene within the tumor. A critical barrier to progress in treating CRPC is that AR signaling inhibitors such as darolutamide, enzalutamide, apalutamide, bicalutamide, and abiraterone, acting through the LBD, fail to inhibit growth driven by the N-terminal domain (NTD)-dependent constitutively active AR-S V such as AR-V7, the most prominent AR-SV. Recent high-impact clinical trials with enzalutamide and abiraterone in CRPC patients demonstrated that just 13.9% of AR-V7-positive patients among 202 patients starting treatment with enzalutamide (Xtandi) or abiraterone acetate (Zytiga) had PSA responses to either of the treatments (Antonarakis E S, Lu C, Luber B, et al. *J. Clin. Oncol.* 2017 Apr. 6. doi: 10.1200/JCO.2016.70.1961), indicating the requirement for next generation AR antagonists that target AR-SVs. In addition, a significant number of CRPC patients are becoming refractory to abiraterone or enzalutamide and apalutamide, and darolutamide, emphasizing the need for next generation AR antagonists.

Current evidences demonstrate that CRPC growth is dependent on constitutively active AR including AR-SV's that lack the LBD such as AR-V7 and therefore cannot be inhibited by conventional antagonists. AR inhibition and degradation through binding to a domain that is distinct from the AR LBD provides alternate strategies to manage CRPC.

Molecules that degrade the AR prevent any inadvertent AR activation through growth factors or signaling pathways, or promiscuous ligand-dependent activation. In addition, molecules that inhibit the constitutive activation of AR-SVs are extremely important to provide extended benefit to CRPC patients.

Currently only a few chemotypes are known to degrade AR which include the SARDs ARN-509, AZD-3514, and ASC-J9. However, these molecules degrade AR indirectly at much higher concentrations than their binding coefficient and they fail to degrade the AR-SVs that have become in recent years the primary reason for resurgence of treatment-resistant CRPC.

This invention describes novel AR antagonists with unique pharmacology that strongly (high potency and efficacy) and selectively bind AR (better than known antagonists in some cases; bind to LBD and/or NTD), antagonize AR, and degrade AR full length (AR-FL) and AR-SV. Selective androgen receptor degrader (SARD) compounds possess dual degradation and AR-SV inhibitory functions and hence are distinct from any available CRPC therapeutics. These novel selective androgen receptor degrader (SARD) compounds inhibit the growth of PCa cells and tumors that are dependent on AR-FL and AR-SV for proliferation.

SARDs have the potential to evolve as new therapeutics to treat CRPCs that are untreatable with any other antagonists. This unique property of degrading AR-S V has extremely important health consequences for prostate cancer. Till date only one series of synthetic molecules (EPI-001, EPI-506, etc.) and some marine natural products such as the sinkotamides and glycerol ether Naphetenone B, are reported to bind to AR-NTD and inhibit AR function and PCa cell growth, albeit at lower affinity and inability to degrade the receptor. The SARDs reported herein also bind to AR-NTD and inhibit NTD-driven (e.g., ligand independent) AR activity.

The positive correlation between AR and PCa and the lack of a fail-safe AR antagonist, emphasizes the need for molecules that inhibit AR function through novel or alternate mechanisms and/or binding sites, and that can elicit antagonistic activities within an altered cellular environment.

Although traditional antiandrogens such as darolutamide, enzalutamide, apalutamide, bicalutamide and flutamide and androgen deprivation therapies (ADT) were approved for use in prostate cancer, there is significant evidence that antiandrogens could also be used in a variety of other hormone dependent and hormone independent cancers. For example, antiandrogens have been tested in breast cancer (enzalutamide; Breast Cancer Res. (2014) 16(1): R7), non-small cell lung cancer (shRNAi AR), renal cell carcinoma (ASC-J9), partial androgen insensitivity syndrome (PAIS) associated malignancies such as gonadal tumors and seminoma, advanced pancreatic cancer (*World J. Gastroenterology* 20(29), 9229), cancer of the ovary, fallopian tubes, or peritoneum, cancer of the salivary gland (Head and Neck (2016) 38, 724-731; ADT was tested in AR-expressing recurrent/metastatic salivary gland cancers and was confirmed to have benefit on progression free survival and overall survival endpoints), bladder cancer (Oncotarget 6(30), 29860-29876); *Int J. Endocrinol* (2015), Article ID 384860), pancreatic cancer, lymphoma (including mantle cell), and hepatocellular carcinoma. Use of a more potent antiandrogen such as a SARD in these cancers may more efficaciously treat the progression of these and other cancers. Other AR-expressing cancers may also benefit from SARD treatment such as breast cancer (e.g., triple negative breast cancer (TNBC)), testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer.

Triple negative breast cancer (TNBC) is a type of breast cancer lacking the expression of the estrogen receptor (ER), progesterone receptor (PR), and HER2 receptor kinase. As such, TNBC lacks the hormone and kinase therapeutic targets used to treat other types of primary breast cancers. Correspondingly, chemotherapy is often the initial pharmacotherapy for TNBC. Interestingly, AR is often still expressed in TNBC and may offer a hormone targeted therapeutic alternative to chemotherapy. In ER-positive breast cancer, AR is a positive prognostic indicator as it is believed that activation of AR limits and/or opposes the effects of the ER in breast tissue and tumors. However, in the absence of ER, it is possible that AR actually supports the growth of breast cancer tumors. Though the role of AR is not fully understood in TNBC, we have evidence that certain TNBC's may be supported by androgen independent activation of AR-SVs lacking the LBD or androgen-dependent activation of AR full length. As such, darolutamide, enzalutamide, apalutamide, and other LBD-directed traditional AR antagonists would not be able to antagonize AR-SVs in these TNBC's. However, SARDs of this invention which are capable of destroying AR-SVs (see Table 1 and Example 2) through a binding site in the NTD of AR (see Example 9 of US2017-0368003) would be able to antagonize AR including AR-SV observed in TNBC patient derived xenograpfts and provide an anti-tumor effect, as shown in Example 8 of US2017-0368003.

Traditional antiandrogens such as bicalutamide and flutamide were approved for use in prostate cancer. Subsequent studies have demonstrated the utility of antiandrogens (e.g., flutamide, spironolactone, cyproterone acetate, finasteride and chlormadinone acetate) in androgen-dependent dermatological conditions such as androgenic alopecia (male pattern baldness), acne vulgaris, and hirsutism (e.g., in female facial hair). Prepubertal castration prevents sebum production and androgenic alopecia but this can be reversed by use of testosterone, suggesting its androgen-dependence.

The AR gene has a polymorphism of glutamine repeats (polyQ) within exon 1 which when shortened may augment AR transactivation (i.e., hyperandrogenism). It has been found that shortened polyQ polymorphisms are more common in people with alopecia, hirsutism, and acne. Classic antiandrogens are undesirable for these purposes because they are ineffective through dermal dosing and their long-term systemic use raises the risks of untoward sexual effects such as gynecomastia and impotence. Further, similar to CPRC discussed above, inhibition of ligand-dependent AR activity alone may not be sufficient as AR can be activated by various cellular factors other than the endogeneous androgens testosterone (T) and dihydrotestosterone (DHT), such as growth factors, kinases, co-activator overexpression and/or promiscuous activation by other hormones (e.g., estrogens or glucocorticoids). Consequently, blocking the binding of T and DHT to AR with a classical antiandrogen may not be sufficient to have the desired efficacy.

An emerging concept is the topical application of a SARD to destroy the AR locally to the affected areas of the skin or other tissue without exerting any systemic antiandrogenism. For this use, a SARD that does not penetrate the skin or is rapidly metabolized would be preferable.

Supporting this approach is the observation that cutaneous wound healing has been demonstrated to be suppressed by androgens. Castration of mice accelerates cutaneous wound healing while attenuating the inflammation in the wounds. The negative correlation between androgen levels and cutaneous healing and inflammation, in part, explains another mechanism by which high levels of endogenous androgens exacerbate hyperandrogenic dermatological conditions. Further, it provides a rationale for the treatment of wounds such as diabetic ulcers or even trauma, or skin disorders with an inflammatory component such as acne or psoriasis, with a topical SARD.

Androgenic alopecia occurs in ~50% of Caucasian males by midlife and up to 90% by 80 years old. Minoxidil (a topical vasodilator) and finasteride (a systemic 5alpha reductase type II inhibitor) are FDA approved for alopecia but require 4-12 months of treatment to produce a therapeutic effect and only arrest hair loss in most with mild to moderate hair regrowth in 30-60%. Since currently available treatments have slow and limited efficacy that varies widely between individuals, and produce unwanted sexual side effects, it is important to find a novel approach to treat androgenic alopecia and other hyperandrogenic dermatologic diseases.

Amyotrophic lateral sclerosis (ALS) is a fatal neurodegenerative disease characterized by selective loss of upper and lower motor neurons and skeletal muscle atrophy. Epidemiologic and experimental evidence suggest the involvement of androgens in ALS pathogenesis ("Anabolic/androgenic steroid nandrolone exacerbates gene expression modifications induced by mutant SOD1 in muscles of mice models of amyotrophic lateral sclerosis." Galbiati M, Onesto E, Zito A, Crippa V, Rusmini P, Mariotti R, Bentivoglio M, Bendotti C, Poletti A. *Pharmacol. Res.* 2012, 65(2), 221-230), but the mechanism through which androgens modify the ALS phenotype is unknown. A transgenic animal model of ALS demonstrated improved survival upon surgical castration (i.e., androgen ablation). Treatment of these castrated animals with the androgen agonist nandrolone decanoate worsened disease manifestations. Castration reduces the AR level, which may be the reason for extended survival. The survival benefit is reversed by androgen agonist ("Androgens affect muscle, motor neuron, and survival in a mouse model of SOD1-related amyotrophic lateral sclerosis."

Aggarwal T, Polanco M J, Scaramuzzino C, Rocchi A, Milioto C, Emionite L, Ognio E, Sambataro F, Galbiati M, Poletti A, Pennuto M. *Neurobiol. Aging*. 2014 35(8), 1929-1938). Notably, stimulation with nandrolone decanoate promoted the recruitment of endogenous androgen receptor into biochemical complexes that were insoluble in sodium dodecyl sulfate, a finding consistent with protein aggregation. Overall, these results shed light on the role of androgens as modifiers of ALS pathogenesis via dysregulation of androgen receptor homeostasis. Antiandrogens should block the effects of nandrolone undecanoate or endogeneous androgens and reverse the toxicities due to AR aggregation. Further, an antiandrogen that can block action of LBD-dependent AR agonists and concomitantly lower AR protein levels, such as the SARDs of this invention, would be therapeutic in ALS. Riluzole is an available drug for ALS treatment, however, it only provides short-term effects. There is an urgent need for drugs that extend the survival of ALS patients.

Androgen receptor action promotes uterine proliferation. Hyperandrogenicity of the short polyQ AR has been associated with increased leiomyoma or uterine fibroids. (Hsieh Y Y, Chang C C, Tsai F J, Lin C C, Yeh L S, Peng C T. *J. Assist. Reprod. Genet.* 2004, 21(12), 453-457). A separate study of Brazilian women found that shorter and longer [CAG](n) repeat alleles of AR were exclusive to the leiomyoma group in their study (Rosa F E, Canevari Rde A, Ambrosio E P, Ramos Cirilo P D, Pontes A, Rainho C A, Rogatto S R. *Clin. Chem. Lab. Med.* 2008, 46(6), 814-823). Similarly, in Asian Indian women long polyQ AR was associated with endometriosis and leiomyoma and can be regarded as high-risk markers. SARDs could be used in women with uterine fibroids, especially those expressing shorter and longer [CAG](n) repeat alleles, to treat existing uterine fibroids, prevent worsening of fibroids and/or ameliorate carcinogenicity associated with fibroids.

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it is necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. J Vasc Surg (2016) 63(6): 1602-1612) showed that flutamide (50 mg/kg) or ketoconazole (150 mg/kg) attenuated porcine pancreatic elastase (0.35 U/mL) induced AAA by 84.2% and 91.5% compared to vehicle (121%). Further AR-/- mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

X-linked spinal-bulbar muscular atrophy (SBMA—also known as Kennedy's disease) is a muscular atrophy that arises from a defect in the androgen receptor gene on the X chromosome. Proximal limb and bulbar muscle weakness results in physical limitations including dependence on a wheelchair in some cases. The mutation results in a protracted polyglutamine tract added to the N-terminal domain of the androgen receptor (polyQ AR). Binding and activation of this lengthened polyQ AR by endogeneous androgens (testosterone and DHT) results in unfolding and nuclear translocation of the mutant androgen receptor. The androgen-induced toxicity and androgen-dependent nuclear accumulation of polyQ AR protein seems to be central to the pathogenesis. Therefore, the inhibition of the androgen-activated polyQ AR might be a therapeutic option (A. Baniahmad. Inhibition of the androgen receptor by antiandrogens in spinobulbar muscle atrophy. *J. Mol. Neurosci.* 2016 58(3), 343-347). These steps are required for pathogenesis and result in partial loss of transactivation function (i.e., an androgen insensitivity) and a poorly understood neuromuscular degeneration. Support of the use of antiandrogens comes in a report in which the antiandrogen flutamide protects male mice from androgen-dependent toxicity in three models of spinal bulbar muscular atrophy (Renier K J, Troxell-Smith S M, Johansen J A, Katsuno M, Adachi H, Sobue G, Chua J P, Sun Kim H, Lieberman A P, Breedlove S M, Jordan C L. *Endocrinology* 2014, 155(7), 2624-2634). Currently there are no disease-modifying treatments but rather only symptom directed treatments. Efforts to target the polyQ AR of Kennedy's disease as the proximal mediator of toxicity by harnessing cellular machinery to promote its degradation, i.e., through the use of a SARD, hold promise for therapeutic intervention. Selective androgen receptor degraders such as those reported herein bind to and degrade all androgen receptors tested (full length, splice variant, antiandrogen resistance mutants, etc.) so degradation of polyQ AR polymorphism is also expected, indicating that they are promising leads for treatment of SBMA.

Here selective androgen receptor degrader (SARD) compounds are described that may bind to the LBD and/or an alternate binding and degradation domain (BDD) located in the NTD, antagonize AR, and degrade AR thereby blocking ligand-dependent and ligand-independent AR activities. This novel mechanism produces improved efficacy when dosed systemically (e.g., for prostate cancer) or topically (e.g., dermatological diseases).

SUMMARY OF THE INVENTION

One embodiment of the invention encompasses a selective androgen receptor degrader (SARD) compound, or its isomer, optical isomer, or any mixture of optical isomers, pharmaceutically acceptable salt, pharmaceutical product, polymorph, hydrate or any combination thereof, wherein said SARD compound is represented by a compound of the following structures:

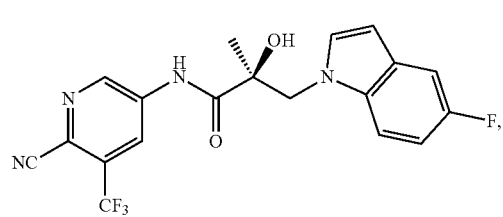

47

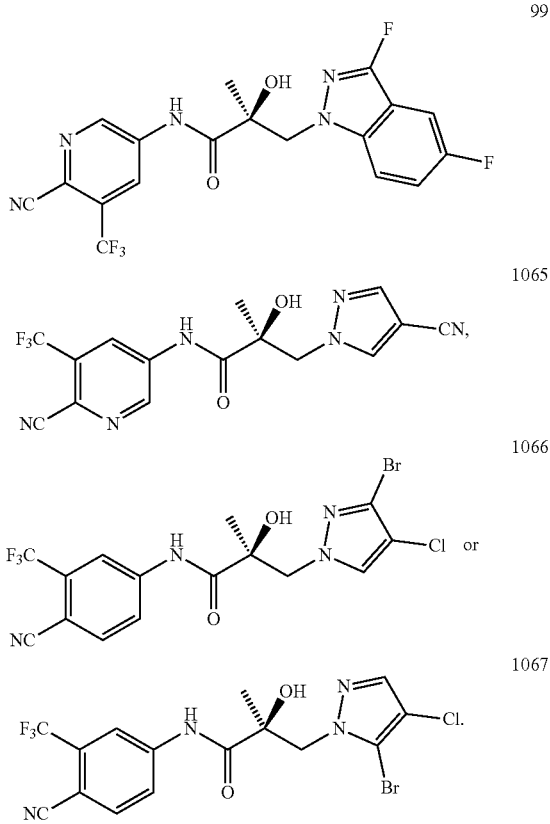

One embodiment of the invention encompasses the SARD compound having at least one of the following properties: binding to the AR through an alternate binding domain in the NTD; binds to the AR through the AR ligand binding domain (LBD); exhibits AR-splice variant (AR-SV) degradation activity; exhibits AR-full length (AR-FL) degradation activity including pathogenic mutations thereof; exhibits AR-SV inhibitory activity (i.e., is an AR-SV antagonist); exhibits AR-FL inhibitory activity (i.e., is an AR-FL antagonist) including pathogenic mutations thereof; possesses dual AR-SV degradation and AR-SV inhibitory functions; dual AR-FL degradation and AR-FL inhibitory functions and/or AR antagonism in vivo of an AR target organ.

Another embodiment of the invention encompasses pharmaceutical compositions comprising a SARD compound according to this invention, or its isomer, optical isomer, or any mixture of optical isomers, pharmaceutically acceptable salt, pharmaceutical product, polymorph, hydrate or any combination thereof, and a pharmaceutically acceptable carrier. The pharmaceutical composition may be formulated for topical use. The topical pharmaceutical composition may be a solution, lotion, salve, cream, ointment, liposome, spray, gel, foam, roller stick, cleansing soaps or bars, emulsion, mousse, aerosol, or shampoo. The pharmaceutical composition may be formulated for oral use.

The invention encompasses a method of treating prostate cancer (PCa) or increasing survival in a male subject in need of treatment comprising administering to the subject a therapeutically effective amount of a compound defined by formulas 47, 99, 1065, 1066 and 1067. The prostate cancer includes, but is not limited to, advanced prostate cancer, castration resistant prostate cancer (CRPC), metastatic CRPC (mCRPC), non-metastatic CRPC (nmCRPC), high-risk nmCRPC or any combination thereof. Another embodiment of the invention encompasses the method further comprising administering androgen deprivation therapy (ADT). Alternatively, the method may treat a prostate or other cancer that is resistant to treatment with known androgen receptor antagonist(s) or ADT. In another embodiment, the method may treat enzalutamide resistant prostate cancer. In another embodiment, the method may treat apalutamide resistant prostate cancer. In another embodiment, the method may treat abiraterone resistant prostate cancer. In another embodiment, the method may treat darolutamide resistant prostate cancer. Yet another embodiment of the invention encompasses a method of treating prostate or other AR antagonist resistant cancer with a SARD compound of the invention wherein the androgen receptor antagonist(s) is at least one of darolutamide, apalutamide, enzalutamide, bicalutamide, abiraterone, ARN-509, ODM-201 [darolutamide], EPI-001, EPI-506, AZD-3514, galeterone, ASC-J9, flutamide, hydroxyflutamide, nilutamide, cyproterone acetate, ketoconazole, or spironolactone.

In some embodiments, the prostate cancer is AR antagonist resistant prostate cancer which overexpresses the glucocorticoid receptor (GR). In some embodiments, activation of the GR provides support for growth of the prostate cancer and/or confers antiandrogen resistance to the prostate cancer. In some embodiments, SARDs of this invention can be used to treat GR-dependent or GR-overexpressing prostate cancers, whether antiandrogen resistant or not. In some embodiments, SARDs of this invention can be used to treat PR-dependent or PR-overexpressing prostate cancers, whether antiandrogen resistant or not.

Yet another embodiment of the invention encompasses a method of treating prostate or other AR-expressing cancers using a SARD compound of the invention wherein the other cancers are selected from breast cancer such as triple negative breast cancer (TNBC), testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer. In another embodiment, the breast cancer is triple negative breast cancer (TNBC).

The invention encompasses a method of reducing the levels of AR-splice variants in a subject comprising administering to the subject a therapeutically effective amount of a compound of this invention, or its isomer, optical isomer, or any mixture of optical isomers, pharmaceutically acceptable salt, pharmaceutical product, polymorph, hydrate or any combination thereof. The method may comprise further reducing the levels of AR-full length in the subject.

Another embodiment of the invention encompasses a method of treating Kennedy's disease in a subject comprising administering to the subject a compound of formulas 47, 99, 1065, 1066 and 1067.

Yet another embodiment of the invention encompasses a method of: (a) treating acne in a subject, e.g., acne vulgaris; (b) decreasing sebum production in a subject, e.g., treats sehorrhea, seborrheic dermatitis, or acne; (c) treating hirsutism in a subject, e.g., female facial hair; (d) treating alopecia in a subject, e.g., androgenic alopecia, alopecia areata, alopecia secondary to chemotherapy, alopecia secondary to radiation therapy, alopecia induced by scarring, or alopecia induced by stress; (e) treating a hormonal condition in female, e.g., precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, or vaginal dryness; (f) treating sexual perversion, hypersexuality, or paraphilias in a subject; (g) treating androgen psychosis in a subject; (h) treating virilization in a subject; (i) treating complete or partial androgen insensitivity syndrome in a subject; (j) increasing or modulating ovulation in an animal; (k) treating of cancer in a subject; or any combination thereof, by administering a compound of this invention or a pharmaceutical composition thereof.

One embodiment of the invention encompasses methods of reducing the levels of polyglutamine (polyQ) AR polymorphs in a subject comprising administering a compound according to this invention. The method may inhibit, degrade, or both the function of the polyglutamine (polyQ) AR polymorphs (polyQ-AR). The polyQ-AR may be a short polyQ polymorph or a long polyQ polymorph. When the polyQ-AR is a short polyQ polymorph, the method further treats dermal disease. When the polyQ-AR is a long polyQ polymorph, the method further treats Kennedy's disease.

Another embodiment of the invention encompasses methods of treating amyotrophic lateral sclerosis (ALS) in a subject by administering a therapeutically effective amount of the compound of the invention, or its isomer, optical isomer, or any mixture of optical isomers, pharmaceutically acceptable salt, pharmaceutical product, polymorph, hydrate or any combination thereof; or a pharmaceutical composition thereof.

Another embodiment of the invention encompasses methods of treating abdominal aortic aneurysm (AAA) in a subject by administering a therapeutically effective amount of the compound of the invention, or its isomer, optical isomer, or any mixture of optical isomers, pharmaceutically acceptable salt, pharmaceutical product, polymorph, hydrate or any combination thereof; or a pharmaceutical composition thereof.

Yet another embodiment of the invention encompasses methods of treating uterine fibroids in a subject by administering a therapeutically effective amount of the compound of this invention, or its isomer, optical isomer, or any mixture of optical isomers, pharmaceutically acceptable salt, pharmaceutical product, polymorph, hydrate or any combination thereof; or a pharmaceutical composition thereof.

In yet another aspect, the invention provides a method of treating, suppressing, reducing the incidence, reducing the severity, or inhibiting the progression of a hormonal condition in a male in need thereof, comprising administering to the subject a therapeutically effective amount of a selective androgen receptor degrader (SARD) compound of the invention. In one embodiment, the condition in the method of the invention is hypergonadism, hypersexuality, sexual dysfunction, gynecomastia, precocious puberty in a male, alterations in cognition and mood, depression, hair loss, hyperandrogenic dermatological disorders, precancerous lesions of the prostate, benign prostate hyperplasia, prostate cancer and/or other androgen-dependent cancers.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

FIGS. 5A and 5B) and prostate (FIGS. 5C and 5D) weight reductions for all the compounds dosed at 20 mg/kg over the two studies are reported together, several compounds produced comparable to slightly improved efficacies compared to 1002. However, it is clear that 1065 is the most efficacious AR antagonist in vivo in a Hershberger assay, reaching castration level androgenic organ weight reductions which are significantly more efficacious than all other compounds tested here or previously in our laboratory (or any other small AR antagonist to our knowledge). See FIG. 1C or Table 1 for compound structures.

FIGS. 13A, 13B, and 13C present the xenograft efficacy of 1002 in a model of enzalutamide resistance (MDV resistant VCaP cells or MDVR). FIGS. 13A and 13B: Xenograft (MDVR) reduction presented as % change in tumor volume (T.V.; FIG. 13A) and tumor weights (FIG. 13B) demonstrate that 1002 possessed dose responsive efficacy in MDVR xenografts in rats during the course of a 30 day treatment. FIG. 13C: demonstrated p-values for the differences in tumor size compared to vehicle treated. As can be seen, statistically significant tumor reductions were seen by day 5 of treatment in G2 (20 mg/kg or 20 mpk) and G3 (30 mg/kg or 30 mpk) and remained significant through day 30, whereas G1 (10 mg/kg) tumors were reduced but never attained p-values of less than 0.05.

FIGS. 14A and 14B: Xenograft (MDVR) reduction presented as % change in T.V. (FIG. 14A) or tumor weights (FIG. 14B) demonstrate that 20 mpk (mg/kg) of 1002 and 10 mpk of 1065 and 1058 produced similar reductions in tumor size. FIG. 14C: 1002, 1065, and 1058 were evaluated in MDVR xenograft in intact SRG rats. Starting from day 12 all three treatment groups were significantly different from the vehicle-treated group (p<0.05 to <0.0001). Although 1002-treated group had much lower p-value than the other two treatment groups, it was not statistically different from the other two groups. Tumors weights and levator ani muscle weights were also significantly different from the vehicle-treated group (p<0.001). N=7-8/group.

FIGS. 15A, 15B, and 15C present the comparative Hershberger efficacy of 1065, 1058 and 1002, which reveals pure antagonist pharmacology. FIG. 15A: Seminal vesicles weight (mg); FIG. 15B: prostate weight (mg); and FIG. 15C: Summary of comparative efficacy of the SARDs 1065, 1058 and 1002 with intact vehicle, enobosarm (nonsteroidal anabolic selective agonist), and castrated vehicle. Method: Male Sprague Dawley rats (80-100 g body weight) (n=4-5/group) were castrated (one intact group). One week after castration, the animals were randomized and dosed for 13 days p.o. as indicated below. Dosing solutions were be prepared in 20% DMSO+80% PEG. Body weights were be measured on day 1 and at the time of sacrifice. At sacrifice, prostate and seminal vesicles weights were taken. Results: No evidence of any agonistic activity of the SARDs was found in this study, whereas a structurally similar nonsteroidal anabolic agonist demonstrated significant agonism in these androgenic tissues. This result reveals that even at doses higher than necessary for MDVR efficacy, the SARDs of this invention do not possess any intrinsic agonist efficacy in vivo (i.e., are pure antagonists).

DETAILED DESCRIPTION OF THE PRESENT INVENTION

Figure 1A:
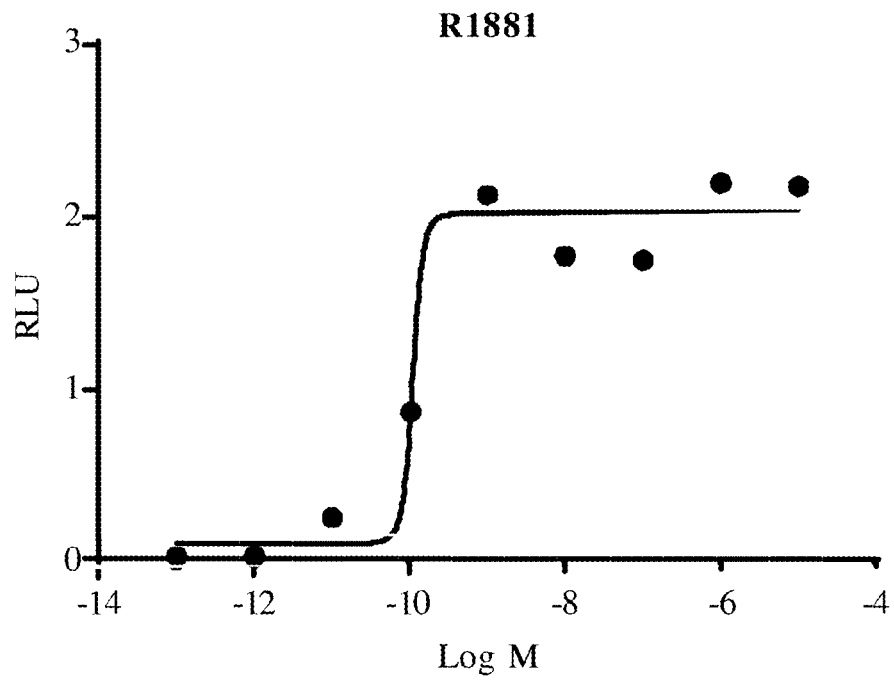
FIGS. 1A-1C present in vitro AR antagonism method. R1881 (FIG. 1A) and enzalutamide (FIG. 1B) served as positive controls for antagonist and agonist activity in this assay. Exemplary compounds (FIG. 1C) present AR antagonism activity, when compounds 1065 and 1048 exhibited approximately 2-fold more potent AR antagonism than 1002. COST cells were transfected with 0.25 µg GRE-LUC, 0.01 µg CMV-renilla LUC, and 25 ng CMV-hAR using Lipofectamine in OptiMEM® medium. Cells were treated 24 hours after transfection with a dose response at the indicated concentrations of the representative compounds, and luciferase assay performed 48 hours after transfection. Firefly luciferase values were normalized to renilla luciferase values. Structures shown below graph. See Table 1 for more data on these compounds.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Androgens act in cells by binding to the AR, a member of the steroid receptor superfamily of transcription factors. As the growth and maintenance of prostate cancer (PCa) is largely controlled by circulating androgens, treatment of PCa heavily relies on therapies that target AR. Treatment with AR antagonists such as darolutamide, enzalutamide, apalutamide, bicalutamide or hydroxyflutamide to disrupt receptor activation has been successfully used in the past to reduce PCa growth. All currently available AR antagonists competitively bind AR and recruit corepressors such as NCoR and SMRT to repress transcription of target genes. However, altered intracellular signaling, AR mutations, and increased expression of coactivators lead to functional impairment of antagonists or even transformation of antagonists into agonists. Studies have demonstrated that mutation of W741 and T877 within AR converts bicalutamide and hydroxyflutamide, respectively, to agonists. Similarly, increased intracellular cytokines recruit coactivators instead of corepressors to AR-responsive promoters subsequently converting bicalutamide to an agonist. Similarly, mutations that have been linked to enzalutamide or apalutamide resistance include F876, H874, T877, and di-mutants T877/5888, T877/D890, F876/T877 (i.e., MR49 cells), and H874/T877 (*Genome Biol.* (2016) 17:10 (doi: 10.1186/s13059-015-0864-1)). Abiraterone resistance mutations include L702H mutations which results in activation of the AR by glucocorticoids such as prednisone, causing resistance to abiraterone because abiraterone is usually prescribed in combination with prednisone. If resistance develops to enzalutamide or apalutamide then often the patient is refractory to abiraterone also and vice versa; or the duration of response is very short. This situation highlights the need for a definitive androgen ablation therapy to prevent AR reactivation in advanced prostate cancers. Arora et al. in *Cell* 155, 1309-1322 reported the induction of glucocorticoid receptor (GR) expression as a common feature of drug-resistant tumors from prostate cancer cell lines (LNCaP/AR) and clinical samples. GR substituted for the AR to activate a similar but distinguishable set of target genes and was necessary for maintenance of the resistant phenotype. The GR agonist dexamethasone was sufficient to confer enzalutamide (or apalutamide) resistance, whereas a GR antagonist restored sensitivity. Acute AR inhibition resulted in GR upregulation in a subset of prostate cancer cells due to relief of AR-mediated feedback repression of GR expression. These findings establish a mechanism of escape from AR blockade through expansion of cells primed to drive AR target genes via an alternative nuclear receptor upon drug exposure. In some cases, the SARDs of this invention are potent GR antagonists in addition to potent AR antagonists. As such, they would possibly prevent the emergence of GR-dependent antiandrogen resistance or treat antiandrogen resistant prostate cancers which are dependent on GR. Though specific AR mutations or AR bypass mechanisms for conferring resistance to darolutamide have not yet been reported, darolutamide binds to the same LBD target on AR and resistance mutations are likely to develop that will be sensitive to the SARDs of this invention, Despite initial response to androgen deprivation therapy (ADT), PCa disease progression is inevitable and the cancer emerges as castration-resistant prostate cancer (CRPC). The primary reason for castration resistant prostate cancer (CRPC) re-emergence is re-activation of androgen receptor (AR) by alternate mechanisms such as:
    (a) intracrine androgen synthesis;
    (b) expression of AR splice variants (AR-SV), e.g., that lack ligand binding domain (LBD);
    (c) AR-LBD mutations with potential to resist antagonists;
    (d) hyper-sensitization of AR to low androgen levels, e.g., due to AR gene amplification or AR mutation;
    (e) amplification of the AR gene within the tumor; and
    (f) over expression of coactivators and/or altered intracellular signal transduction.

The invention encompasses novel selective androgen receptor degrader (SARD) compounds encompassed by 47, 99, 1065, 1066 and 1067, which inhibit the growth of prostate cancer (PCa) cells and tumors that are dependent on AR full length (AR-FL) including pathogenic and resistance mutations and wildtype, and/or AR splice variants (AR-SV) for proliferation.

As used herein, unless otherwise defined, a "selective androgen receptor degrader" (SARD) compound is an androgen receptor antagonist capable of inhibiting the growth of PCa cells and tumors that are dependent on AR-full length (AR-FL) and/or AR splice variants (AR-SV) for proliferation. The SARD compound may not bind to ligand binding domain (LBD). Alternatively, a "selective androgen receptor degrader" (SARD) compound is an androgen receptor antagonist capable of causing degradation of a variety of pathogenic mutant variant AR's and wildtype AR and hence are capable of exerting anti-androgenism is a wide variety of pathogenic altered cellular environments found in the disease states embodied in this invention. In one embodiment, the SARD is orally active. In another embodiment, the SARD is applied topically to the site of action.

The SARD compound may bind to the N-terminal domain (NTD) of the AR; to an alternate binding and degradation domain (BDD) of the AR; to both the AR ligand binding domain (LBD) and to an alternate binding and degradation domain (BDD); or to both the N-terminal domain (NTD) and to the ligand binding domain (LBD) of the AR. In one embodiment, the BDD may be located in the NTD. In one embodiment, the BDD is located in the AF-1 region of the NTD. Alternatively, the SARD compound may be capable of: inhibiting growth driven by the N-terminal domain (NTD)-dependent constitutively active AR-SV; or inhibiting the AR through binding to a domain that is distinct from the AR LBD. Also, the SARD compound may be a strong (i.e., highly potent and highly efficacious) selective androgen receptor antagonist, which antagonizes the AR stronger than other known AR antagonists (e.g., darolutamide, enzalutamide, apalutamide, bicalutamide and abiraterone).

The SARD compound may be a selective androgen receptor antagonist, which targets AR-SVs, which cannot be inhibited by conventional antagonists. The SARD compound may exhibit any one of several activities including, but not limited to: AR-SV degradation activity; AR-FL degradation activity; AR-SV inhibitory activity (i.e., is an AR-SV antagonist); AR-FL inhibitory activity (i.e., is an AR-FL antagonist); inhibition of the constitutive activation of AR-SVs; or inhibition of the constitutive activation of AR-FLs. Alternatively, the SARD compound may possess dual AR-SV degradation and AR-SV inhibitory functions, and/or dual AR-FL degradation and AR-FL inhibitory functions; or alternatively possess all four of these activities.

The SARD compound may also degrade AR-FL and AR-SV. The SARD compound may degrade the AR through binding to a domain that is distinct from the AR LBD. The SARD compound may possess dual degradation and AR-SV inhibitory functions that are distinct from any available CRPC therapeutics. The SARD compound may inhibit the re-activation of the AR by alternate mechanisms such as: intracrine androgen synthesis, expression of AR-SV that lack ligand binding domain (LBD) and AR-LBD mutations with potential to resist antagonists, or inhibit re-activated androgen receptors present in pathogenic altered cellular environments.

Examples of AR-splice variants include, but are not limited to, AR-V7 and ARv567es (a.k.a. AR-V12; S. Sun, et al. Castration resistance in human prostate cancer is conferred by a frequently occurring androgen receptor splice variant. *J Clin Invest.* (2010) 120(8), 2715-2730). Nonlimiting examples of AR mutations conferring antiandrogen resistance are: W741L, T877A, and F876L (J. D. Joseph et al. A clinically relevant androgen receptor mutation confers resistance to second-generation antiandrogens enzalutamide and ARN-509 [apalutamide]. *Cancer Discov.* (2013) 3(9), 1020-1029) mutations. Many other LBD resistance conferring mutations are known in the art and will continue to be discovered. AR-V7 is a splice variant of AR that lacks the LBD (A. H. Bryce & E. S. Antonarakis. Androgen receptor splice variant 7 in castration-resistant prostate cancer: Clinical considerations. *Int J Urol.* (2016 Jun. 3) 23(8), 646-53. doi: 10.1111/iju.13134). It is constitutively active and has been demonstrated to be responsible for aggressive PCa and resistance to endocrine therapy.

The invention encompasses novel selective androgen receptor degrader (SARD) compounds of formulas 47, 99, 1065, 1066 and 1067 which bind to the AR through an alternate binding and degradation domain (BDD), e.g., the NTD or AF-1. The SARDs may further bind the AR ligand binding domain (LBD).

The SARD compounds may be used in treating CRPC that cannot be treated with any other antagonist. The SARD compounds may treat CRPC by degrading AR-SVs. The SARD compounds may maintain their antagonistic activity in AR mutants that normally convert AR antagonists to agonists. For instance, the SARD compounds maintain their antagonistic activity to AR mutants W741L, T877A, and F876L (J. D. Joseph et al. A clinically relevant androgen receptor mutation confers resistance to second-generation antiandrogens enzalutamide and ARN-509 [apalutamide]. *Cancer Discov.* (2013) 3(9), 1020-1029). Alternatively, the SARD compounds elicit antagonistic activity within an altered cellular environment in which LBD-targeted agents are not effective or in which NTD-dependent AR activity is constitutively active. Alternatively, SARD compounds can be co-antagonists of AR and GR and thereby overcome or prevent antiandrogen resistant CRPC in which GR is over-expressed and/or GR is activating the AR axis.

Selective Androgen Receptor Degrader (SARD) Compounds

The invention encompasses selective androgen receptor degrader (SARD) compounds selected from any one of the following structures:

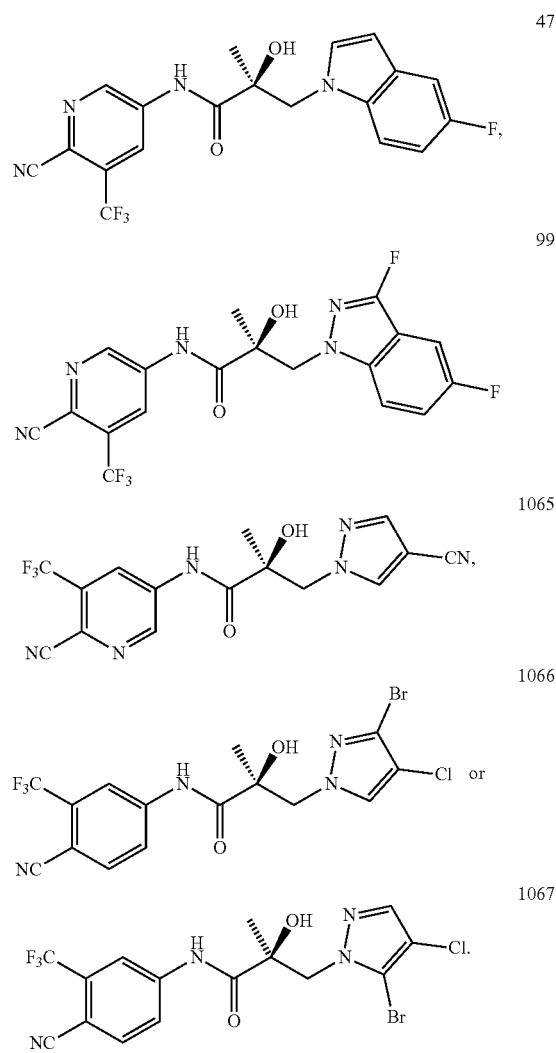

In one embodiment, this invention provides the compounds and/or its use and/or its derivative, optical isomer, mixtures of optical isomers including racemates, isomer, metabolite, pharmaceutically acceptable salt, pharmaceutical product, hydrate, N-oxide, prodrug, polymorph, crystal or combinations thereof.

In one embodiment, the methods of this invention make use of "pharmaceutically acceptable salts" of the compounds, which may be produced, by reaction of a compound of this invention with an acid or base.

The compounds of the invention may be converted into pharmaceutically acceptable salts. A pharmaceutically acceptable salt may be produced by reaction of a compound with an acid or base.

Suitable pharmaceutically acceptable salts of amines may be prepared from an inorganic acid or from an organic acid. Examples of inorganic salts of amines include, but are not limited to, bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphates, sulfates, sulfamates, sulfanilates, sulfonic acids (alkylsulfonates, arylsulfonates, halogen substituted alkylsulfonates, halogen substituted arylsulfonates), sulfonates, or thiocyanates.

Examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates. Examples of inorganic salts of carboxylic acids or phenols may be selected from ammonium, alkali metals, and alkaline earth metals. Alkali metals include, but are not limited to, lithium, sodium, potassium, or cesium Alkaline earth metals include, but are not limited to, calcium, magnesium, aluminium; zinc, barium, cholines, or quaternary ammoniums. Examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglumines, N-methyl-D-glucamines, N,N'-dibenzylethylenediamines, nicotinamides, organic amines, ornithines, pyridines, picolines, piperazines, procaine, tris(hydroxymethyl)methylamines, triethylamines, triethanolamines, trimethylamines, tromethamines and ureas.

In various embodiments, the pharmaceutically acceptable salts of the compounds of this invention include: HCl salt, oxalic acid salt, L-(+)-tartaric acid salt, HBr salt and succinic acid salt. Each represents a separate embodiment of this invention. E.g., the tartaric acid salt of 1002 (1002 Tart.) is exemplified in Table 1.

Salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

The methods of the invention may use an uncharged compound or a pharmaceutically acceptable salt of the compound. In particular, the methods use pharmaceutically acceptable salts of compounds of formulas 47, 99, 1065, 1066 and 1067. The pharmaceutically acceptable salt may be an amine salt or a salt of a phenol of the compounds of formulas 47, 99, 1065, 1066 and 1067.

In one embodiment, the methods of this invention make use of a free base, free acid, non charged or non-complexed compounds of formulas 47, 99, 1065, 1066 and 1067, and/or its isomer, optical isomer, or any mixture of optical isomers, pharmaceutical product, hydrate, polymorph, or combinations thereof.

In one embodiment, the methods of this invention make use of an optical isomer of a compound of formulas 47, 99, 1065, 1066 and 1067. In one embodiment, the methods of this invention make use of an isomer of a compound of formulas 47, 99, 1065, 1066 and 1067. In one embodiment, the methods of this invention make use of a pharmaceutical product of a compound of formulas. In one embodiment, the methods of this invention make use of a hydrate of a compound of formulas. In one embodiment, the methods of this invention make use of a polymorph of a compound of formulas. In one embodiment, the methods of this invention make use of a metabolite of a compound of formulas. In another embodiment, the methods of this invention make use of a composition comprising a compound of formulas, as described herein, or, in another embodiment, a combination of isomer, metabolite, pharmaceutical product, hydrate, polymorph of a compound of formulas.

As used herein, the term "isomer" includes, but is not limited to, optical isomers, structural isomers, or conformational isomers.

The term "isomer" is meant to encompass optical isomers of the SARD compound. It will be appreciated by those skilled in the art that the SARDs of the present invention contain at least one chiral center. Accordingly, the compounds may exist as optically-active (such as an (R) isomer or (S) isomer) or racemic forms. Optically active compounds may exist as enantiomerically enriched mixtures. Some compounds may also exhibit polymorphism. It is to be understood that the present invention encompasses any racemic, optically active, polymorphic, or stereoisomeric form, or mixtures thereof. Thus, the invention may encompass SARD compounds as pure (R)-isomers or as pure (S)-isomers. It is known in the art how to prepare optically active forms. For example, by resolution of the racemic form by recrystallization techniques, by synthesis from optically active starting materials, by chiral synthesis, or by chromatographic separation using a chiral stationary phase.

Compounds of the invention may be hydrates of the compounds. As used herein, the term "hydrate" includes, but is not limited to, hemihydrate, monohydrate, dihydrate, or trihydrate. The invention also includes use of N-oxides of the amino substituents of the compounds described herein.

This invention provides, in other embodiments, use of metabolites of the compounds as herein described. In one embodiment, "metabolite" means any substance produced from another substance by metabolism or a metabolic process.

In one embodiment, the compounds of this invention are prepared according to Example 1.

Biological Activity of Selective Androgen Receptor Degraders

A method of treating prostate cancer (PCa) or increasing the survival of a male subject suffering from prostate cancer comprising administering to the subject a therapeutically effective amount of a compound or its pharmaceutically acceptable salt, or isomer, represented by a compound of formulas 47, 99, 1065, 1066 and 1067.

The prostate cancer may be advanced prostate cancer, refractory prostate cancer, castration resistant prostate cancer (CRPC), metastatic CRPC (mCRPC), non-metastatic CRPC (nmCRPC), high-risk nmCRPC or any combination thereof.

The prostate cancer may depend on AR-FL and/or AR-SV for proliferation. The prostate or other cancer may be resistant to treatment with an androgen receptor antagonist. The prostate or other cancer may be resistant to treatment with darolutamide, enzalutamide, apalutamide, bicalutamide, abiraterone, ARN-509, ODM-201 [darolutamide], EPI-001, EPI-506, AZD-3514, galeterone, ASC-J9, flutamide, hydroxyflutamide, nilutamide, cyproterone acetate, ketoconazole, spironolactone, or any combination thereof. The method may also reduce the levels of AR, AR-FL, AR-FL with antiandrogen resistance-conferring AR-LBD mutations, AR-SV, gene-amplified AR, or any combination thereof.

In one embodiment, this invention provides a method of treating enzalutamide resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

In one embodiment, this invention provides a method of treating apalutamide resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

In one embodiment, this invention provides a method of treating abiraterone resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

The invention encompasses a method of treating or inhibiting the progression of apalutamide resistant prostate cancer (PCa) or increasing the survival of a male subject suffering from apalutamide resistant prostate cancer comprising administering to the subject a therapeutically effective amount of a SARD compound or pharmaceutically acceptable salt, wherein the compound is represented by a compound of formulas 47, 99, 1065, 1066, and 1067.

In one embodiment, this invention provides a method of treating darolutamide resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

The invention encompasses a method of treating or inhibiting the progression of darolutamide resistant prostate cancer (PCa) or increasing the survival of a male subject suffering from apalutamide resistant prostate cancer comprising administering to the subject a therapeutically effective amount of a SARD compound or pharmaceutically acceptable salt, wherein the compound is represented by a compound of formulas 47, 99, 1065, 1066, and 1067.

The method may further comprise administering androgen deprivation therapy to the subject.

In one embodiment, this invention provides a method of treating triple negative breast cancer (TNBC) comprising administering to the subject a therapeutically effective amount of a compound of this invention, or its optical isomer, isomer, pharmaceutically acceptable salt, pharmaceutical product, polymorph, hydrate or any combination thereof.

The method may further comprise a second therapy such as androgen deprivation therapy (ADT) or LHRH agonist or antagonist. LHRH agonists include, but are not limited to, leuprolide acetate.

The invention encompasses a method of treating or inhibiting the progression of prostate cancer (PCa) or increasing the survival of a male subject suffering from prostate cancer comprising administering to the subject a therapeutically effective amount of a SARD compound or pharmaceutically acceptable salt, wherein the compound is at least one of compounds 47, 99, 1065, 1066 and 1067.

The invention encompasses a method of treating or inhibiting the progression of refractory prostate cancer (PCa) or increasing the survival of a male subject suffering from refractory prostate cancer comprising administering to the subject a therapeutically effective amount of a SARD compound or pharmaceutically acceptable salt, wherein the compound is represented by a compound of formulas 47, 99, 1065, 1066 and 1067.

The invention encompasses a method of treating or increasing the survival of a male subject suffering from castration resistant prostate cancer (CRPC) comprising administering to the subject a therapeutically effective amount of a SARD wherein the compound is represented by a compound of formulas 47, 99, 1065, 1066 and 1067.

The method may further comprise administering androgen deprivation therapy to the subject.

The invention encompasses a method of treating or inhibiting the progression of enzalutamide resistant prostate cancer (PCa) or increasing the survival of a male subject suffering from enzalutamide resistant prostate cancer comprising administering to the subject a therapeutically effective amount of a SARD compound or pharmaceutically acceptable salt, wherein the compound is represented by a compound of formulas 47, 99, 1065, 1066 and 1067.

The method may further comprise administering androgen deprivation therapy to the subject.

The invention encompasses a method of treating or inhibiting the progression of triple negative breast cancer (TNBC) or increasing the survival of a female subject suffering from triple negative breast cancer comprising administering to the subject a therapeutically effective amount of a SARD compound or pharmaceutically acceptable salt, wherein the compound is represented by a compound of formulas 47, 99, 1065, 1066 and 1067.

As used herein, the term "increase the survival" refers to a lengthening of time when describing the survival of a subject. Thus in this context, the compounds of the invention may be used to increase the survival of men with advanced prostate cancer, refractory prostate cancer, castration resistant prostate cancer (CRPC); metastatic CRPC (mCRPC); non-metastatic CRPC (nmCRPC); or high-risk nmCRPC; or women with TNBC.

Alternatively, as used herein, the terms "increase", "increasing", or "increased" may be used interchangeably and refer to an entity becoming progressively greater (as in size, amount, number, or intensity), wherein for example the entity is sex hormone-binding globulin (SHBG) or prostate-specific antigen (PSA).

The compounds and compositions of the invention may be used for increasing metastasis-free survival (MFS) in a subject suffering from non-metastatic prostate cancer. The non-metastatic prostate cancer may be non-metastatic advanced prostate cancer, non-metastatic CRPC (nmCRPC), or high-risk nmCRPC.

The SARD compounds described herein may be used to provide a dual action. For example, the SARD compounds may treat prostate cancer and prevent metastasis. The prostate cancer may be refractory prostate cancer; advanced prostate cancer; castration resistant prostate cancer (CRPC); metastatic CRPC (mCRPC); non-metastatic CRPC (nmCRPC); or high-risk nmCRPC.

The SARD compounds described herein may be used to provide a dual action. For example, the SARD compounds may treat TNBC and prevent metastasis.

Men with advanced prostate cancer who are at high risk for progression to castration resistant prostate cancer (CRPC) are men on ADT with serum total testosterone concentrations greater than 20 ng/dL or men with advanced prostate cancer who at the time of starting ADT had either (1) confirmed Gleason pattern 4 or 5 prostate cancer, (2) metastatic prostate cancer, (3) a PSA doubling time <3 months, (4) a PSA ≥20 ng/mL, or (5) a PSA relapse in <3 years after definitive local therapy (radical prostatectomy or radiation therapy).

Normal levels of prostate specific antigen (PSA) are dependent on several factors, such as age and the size of a male subject's prostate, among others. PSA levels in the range between 2.5-10 ng/mL are considered "borderline high" while levels above 10 ng/mL are considered "high." A rate change or "PSA velocity" greater than 0.75/year is considered high. PSA levels may increase despite ongoing ADT or a history of ADT, surgical castration or despite treatment with antiandrogens and/or LHRH agonist.

Men with high risk non-metastatic castration resistant prostate cancer (high-risk nmCRPC) may include those with rapid PSA doubling times, having an expected progression-free survival of approximately 18 months or less (Miller K, Moul J W, Gleave M, et al. 2013. "Phase III, randomized, placebo-controlled study of once-daily oral zibotentan (ZD4054) in patients with non-metastatic castration-resistant prostate cancer," *Prostate Canc Prost Dis*. February; 16:187-192). This relatively rapid progression of their disease underscores the importance of novel therapies for these individuals.

The methods of the invention may treat subjects with PSA levels greater than 8 ng/mL where the subject suffers from high-risk nmCRPC. The patient population includes subjects suffering from nmCRPC where PSA doubles in less than 8 months or less than 10 months. The method may also treat patient populations where the total serum testosterone levels are greater than 20 ng/mL in a subject suffering from high-risk nmCRPC. In one case, the serum free testosterone levels are greater than those observed in an orchiectomized male in a subject suffering from high-risk nmCRPC.

The pharmaceutical compositions of the invention may further comprise at least one LHRH agonist or antagonist, antiandrogen, anti-programmed death receptor 1 (anti-PD-1) drug or anti-PD-L1 drug. LHRH agonists include, but are not limited to, leuprolide acetate (Lupron®) (U.S. Pat. Nos. 5,480,656; 5,575,987; 5,631,020; 5,643,607; 5,716,640; 5,814,342; 6,036,976 hereby incorporated by reference) or goserelin acetate (Zoladex®) (U.S. Pat. Nos. 7,118,552; 7,220,247; 7,500,964 hereby incorporated by reference). LHRH antagonists include, but are not limited to, degarelix or abarelix. Antiandrogens include, but are not limited to, bicalutamide, flutamide, finasteride, dutasteride, darolutamide, enzalutamide, apalutamide, nilutamide, chlormadinone, abiraterone, or any combination thereof. Anti-PD-1 drugs include, but are not limited to, AMP-224, nivolumab, pembrolizumab, pidilizumab, and AMP-554. Anti-PD-L1 drugs include, but are not limited to, BMS-936559, atezolizumab, durvalumab, avelumab, and MPDL3280A. Anti-CTLA-4 drugs include, but are not limited to, ipilimumab and tremelimumab.

Treatment of prostate cancer, advanced prostate cancer, CRPC, mCRPC and/or nmCRPC may result in clinically meaningful improvement in prostate cancer related symptoms, function and/or survival. Clinically meaningful improvement can be determined by an increase in radiographic progression free survival (rPFS) if cancer is metastatic, or an increase metastasis-free survival (MFS) if cancer is non-metastatic, among others.

The invention encompasses methods of lowering serum prostate specific antigen (PSA) levels in a male subject suffering from prostate cancer, advanced prostate cancer, metastatic prostate cancer or castration resistant prostate cancer (CRPC) comprising administering a therapeutically effective amount of a SARD compound, wherein the compound is represented by the structure of formulas 47, 99, 1065, 1066 and 1067.

The invention encompasses a method of secondary hormonal therapy that reduces serum PSA in a male subject suffering from castration resistant prostate cancer (CRPC) comprising administering a therapeutically effective amount of a compound of formulas 47, 99, 1065, 1066 and 1067 that reduces serum PSA in a male subject suffering from castration resistant prostate cancer.

The invention encompasses a method of reducing levels of AR, AR-full length (AR-FL), AR-FL with antiandrogen resistance-conferring AR-LBD mutations, AR-splice variant (AR-SV), and/or amplifications of the AR gene within the tumor in the subject in need thereof comprising administering a therapeutically effective amount of a compound of formulas 47, 99, 1065, 1066 and 1067 to reduce the level of AR, AR-full length (AR-FL), AR-FL with antiandrogen resistance-conferring AR-LBD or other AR mutations, AR-splice variant (AR-SV), and/or amplifications of the AR gene within the tumor.

The method may increase radiographic progression free survival (rPFS) or metastasis-free survival (MFS).

Subjects may have non-metastatic cancer; failed androgen deprivation therapy (ADT), undergone orchiectomy, or have high or increasing prostate specific antigen (PSA) levels; subjects may be a patient with prostate cancer, advanced prostate cancer, refractory prostate cancer, CRPC patient, metastatic castration resistant prostate cancer (mCRPC) patient, or non-metastatic castration resistant prostate cancer (nmCRPC) patient. In these subjects, the refractory may be enzalutamide resistant prostate cancer. In these subjects, the nmCRPC may be high-risk nmCRPC. Further the subject may be on androgen deprivation therapy (ADT) with or without castrate levels of total T.

Subjects may have non-metastatic cancer; failed androgen deprivation therapy (ADT), undergone orchidectomy, or have high or increasing prostate specific antigen (PSA) levels; subjects may be a patient with prostate cancer, advanced prostate cancer, refractory prostate cancer, CRPC patient, metastatic castration resistant prostate cancer (mCRPC) patient, or non-metastatic castration resistant prostate cancer (nmCRPC) patient. In these subjects, the refractory PC may be apalutamide resistant prostate cancer. In these subjects, the nmCRPC may be high-risk nmCRPC. Further the subject may be on androgen deprivation therapy (ADT) with or without castrate levels of total T.

As used herein, the phrase "a subject suffering from castration resistant prostate cancer" refers to a subject with at least one of the following characteristics: has been previously treated with androgen deprivation therapy (ADT); has responded to the ADT and currently has a serum PSA >2 ng/mL or >2 ng/mL and representing a 25% increase above the nadir achieved on the ADT; a subject which despite being maintained on androgen deprivation therapy is diagnosed to have serum PSA progression; a castrate level of serum total testosterone (<50 ng/dL) or a castrate level of serum total testosterone (<20 ng/dL). The subject may have rising serum PSA on two successive assessments at least 2 weeks apart; been effectively treated with ADT; or has a history of serum PSA response after initiation of ADT.

As used herein, the term "serum PSA progression" refers to a 25% or greater increase in serum PSA and an absolute increase of 2 ng/ml or more from the nadir; or to serum PSA >2 ng/mL, or >2 ng/mL and a 25% increase above the nadir after the initiation of androgen deprivation therapy (ADT). The term "nadir" refers to the lowest PSA level while a patient is undergoing ADT.

The term "serum PSA response" refers to at least one of the following: at least 90% reduction in serum PSA value prior to the initiation of ADT; to <10 ng/mL undetectable level of serum PSA (<0.2 ng/mL) at any time; at least 50% decline from baseline in serum PSA; at least 90% decline from baseline in serum PSA; at least 30% decline from baseline in serum PSA; or at least 10% decline from baseline in serum PSA.

The methods of this invention comprise administering a combination of forms of ADT and a compound of this invention. Forms of ADT include a LHRH agonist. LHRH agonist includes, but is not limited to, leuprolide acetate (Lupron®) (U.S. Pat. Nos. 5,480,656; 5,575,987; 5,631,020; 5,643,607; 5,716,640; 5,814,342; 6,036,976 hereby incorporated by reference) or goserelin acetate (Zoladex®) (U.S. Pat. Nos. 7,118,552; 7,220,247; 7,500,964 hereby incorporated by reference). Forms of ADT include, but are not limited to LHRH antagonists, reversible antiandrogens, or bilateral orchidectomy. LHRH antagonists include, but are not limited to, degarelix and abarelix. Antiandrogens include, but are not limited to, bicalutamide, flutamide, finasteride, dutasteride, enzalutamide, apalutamide, EPI-001, EPI-506, ODM-201 [darolutamide], nilutamide, chlormadinone, abiraterone, or any combination thereof.

The methods of the invention encompass administering at least one compound of the invention and a lyase inhibitor (e.g., abiraterone).

The term "advanced prostate cancer" refers to metastatic cancer having originated in the prostate, and having widely metastasized to beyond the prostate such as the surrounding tissues to include the seminal vesicles the pelvic lymph nodes or bone, or to other parts of the body. Prostate cancer pathologies are graded with a Gleason grading from 1 to 5 in order of increasing malignancy. Patients with significant risk of progressive disease and/or death from prostate cancer should be included in the definition and any patient with cancer outside the prostate capsule with disease stages as low as IIB clearly has "advanced" disease. "Advanced prostate cancer" can refer to locally advanced prostate cancer. Similarly, "advanced breast cancer" refers to metastatic cancer having originated in the breast, and having widely metastasized to beyond the breast to surrounding tissues or other parts of the body such as the liver, brain, lungs, or bone.

The term "refractory" may refer to cancers that do not respond to treatment. E.g., prostate or breast cancer may be resistant at the beginning of treatment or it may become resistant during treatment. "Refractory cancer" may also be referred to herein as "resistant cancer".

The term "castration resistant prostate cancer" (CRPC) refers to advanced prostate cancer that is worsening or progressing while the patient remains on ADT or other therapies to reduce testosterone, or prostate cancer which is considered hormone refractory, hormone naïve, androgen independent or chemical or surgical castration resistant. CRPC may be the result of AR activation by intracrine androgen synthesis; expression of AR splice variants (AR-SV) that lack ligand binding domain (LBD); or expression of AR-LBD or other AR mutations with potential to resist antagonists. Castration resistant prostate cancer (CRPC) is an advanced prostate cancer which developed despite ongoing ADT and/or surgical castration. Castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix or abarelix), antiandrogens (e.g., bicalutamide, flutamide, enzalutamide, apalutamide, darolutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometrig™, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

Castration resistant prostate cancer may be defined as hormone naïve prostate cancer. In men with castration resistant prostate cancer, the tumor cells may have the ability to grow in the absence of androgens (hormones that promote the development and maintenance of male sex characteristics).

Many early prostate cancers require androgens for growth, but advanced prostate cancers are androgen-independent, or hormone naïve.

The term "androgen deprivation therapy" (ADT) may include orchiectomy; administering luteinizing hormone-releasing hormone (LHRH) analogs; administering luteinizing hormone-releasing hormone (LHRH) antagonists; administering 5α-reductase inhibitors; administering antiandrogens; administering inhibitors of testosterone biosynthesis; administering estrogens; or administering 17α-hydroxylase/C17,20 lyase (CYP17A1) inhibitors. LHRH drugs lower the amount of testosterone made by the testicles. Examples of LHRH analogs available in the United States include leuprolide (Lupron®, Viadur®, Eligard®), goserelin (Zoladex®), triptorelin (Trelstar®), and histrelin (Vantas®). Antiandrogens block the body's ability to use any androgens. Examples of antiandrogens drugs include darolutamide (Nubeqa®), enzalutamide (Xtandi®), apalutamide (Erleada®), flutamide (Eulexin®), bicalutamide (Casodex®), and nilutamide (Nilandron®). Luteinizing hormone-releasing hormone (LHRH) antagonists include abarelix (Plenaxis®) or degarelix (Firmagon®) (approved for use by the FDA in 2008 to treat advanced prostate cancer). 5α-Reductase inhibitors block the body's ability to convert testosterone to the more active androgen, 5α-dihydrotestosterone (DHT) and include drugs such as finasteride (Proscar®) and dutasteride (Avodart®). Inhibitors of testosterone biosynthesis include drugs such as ketoconazole (Nizoral®). Estrogens include diethylstilbestrol or 17β-estradiol. 17α-Hydroxylase/C17,20 lyase (CYP17A1) inhibitors include abiraterone (Zytiga®).

The invention encompasses a method of treating antiandrogen-resistant prostate cancer. The antiandrogen may include, but is not limited to, bicalutamide, hydroxyflutamide, flutamide, darolutamide, enzalutamide, apalutamide or abiraterone.

Treatment of Triple Negative Breast Cancer (TNBC)

Triple negative breast cancer (TNBC) is a type of breast cancer lacking the expression of the estrogen receptor (ER), progesterone receptor (PR), and HER2 receptor kinase. As such, TNBC lacks the hormone and kinase therapeutic targets used to treat other types of primary breast cancers. Correspondingly, chemotherapy is often the initial pharmacotherapy for TNBC. Interestingly, AR is often still expressed in TNBC and may offer a hormone targeted therapeutic alternative to chemotherapy. In ER-positive breast cancer, AR is a positive prognostic indicator as it is believed that activation of AR limits and/or opposes the effects of the ER in breast tissue and tumors. However, in the absence of ER, it is possible that AR actually supports the growth of breast cancer tumors. Though the role of AR is not fully understood in TNBC, we have evidence that certain TNBC's may be supported by androgen independent activation of AR-SVs lacking the LBD or androgen-dependent activation of AR full length. As such, darolutamide, enzalutamide, apalutamide, and other LBD-directed traditional AR antagonists would not be able to antagonize AR-SVs in these TNBC's. However, SARDs of this invention which are capable of destroying AR-SVs (see Table 1 and Example 2) through a binding site in the NTD of AR (see Example 9 of US2017-0368003) would be able to antagonize AR in these TNBC's and provide an anti-tumor effect, as shown in Example 8 of US2017-0368003.

Treatment of Kennedy's Disease

Muscle atrophy (MA) is characterized by wasting away or diminution of muscle and a decrease in muscle mass. For example, post-polio MA is muscle wasting that occurs as part of the post-polio syndrome (PPS). The atrophy includes weakness, muscle fatigue, and pain. Another type of MA is X-linked spinal-bulbar muscular atrophy (SBMA—also known as Kennedy's Disease). This disease arises from a defect in the androgen receptor gene on the X chromosome, affects only males, and its onset is in late adolescence to adulthood. Proximal limb and bulbar muscle weakness results in physical limitations including dependence on a wheelchair in some cases. The mutation results in an extended polyglutamine tract at the N-terminal domain of the androgen receptor (polyQ AR).

Binding and activation of the polyQ AR by endogeneous androgens (testosterone and DHT) results in unfolding and nuclear translocation of the mutant androgen receptor. The androgen-induced toxicity and androgen-dependent nuclear accumulation of polyQ AR protein seems to be central to the pathogenesis. Therefore, the inhibition of the androgen-activated polyQ AR might be a therapeutic option (A. Baniahmad. Inhibition of the androgen receptor by antiandrogens in spinobulbar muscle atrophy. *J. Mol. Neurosci.* 2016 58(3), 343-347). These steps are required for pathogenesis and result in partial loss of transactivation function (i.e., an androgen insensitivity) and a poorly understood neuromuscular degeneration. Peripheral polyQ AR antisense therapy rescues disease in mouse models of SBMA (*Cell Reports* 7, 774-784, May 8, 2014). Further support of use antiandrogen comes in a report in which the antiandrogen flutamide protects male mice from androgen-dependent toxicity in three models of spinal bulbar muscular atrophy (Renier K J, Troxell-Smith S M, Johansen J A, Katsuno M, Adachi H, Sobue G, Chua J P, Sun Kim H, Lieberman A P, Breedlove S M, Jordan C L. *Endocrinology* 2014, 155(7), 2624-2634). These steps are required for pathogenesis and result in partial loss of transactivation function (i.e., an androgen insensitivity) and a poorly understood neuromuscular degeneration. Currently there are no disease-modifying treatments but rather only symptom directed treatments. Efforts to target the polyQ AR as the proximal mediator of toxicity by harnessing cellular machinery to promote its degradation hold promise for therapeutic intervention.

Selective androgen receptor degraders such as those reported herein bind to, inhibit transactivation, and degrade all androgen receptors tested to date (full length, splice variant, antiandrogen resistance mutants, etc.), indicating that they are promising leads for treatment diseases whose pathogenesis is androgen-dependent such as SBMA.

The invention encompasses methods of treating Kennedy's disease comprising administering a therapeutically effective amount of a compound of formulas 44-46, 98, 300-308, and 1050-1067.

As used herein, the term "androgen receptor associated conditions" or "androgen sensitive diseases or disorders" or "androgen-dependent diseases or disorders" are conditions, diseases, or disorders that are modulated by or whose pathogenesis is dependent upon the activity of the androgen receptor. The androgen receptor is expressed in most tissues of the body however it is overexpressed in, inter alia, the prostate and skin. ADT has been the mainstay of prostate cancer treatment for many years, and SARDs may also be useful in treating various prostate cancers, benign prostatic hypertrophy, prostamegaly, and other maladies of the prostate.

The invention encompasses methods of treating benign prostatic hypertrophy comprising administering a therapeutically effective amount of at least one compound of formulas 47, 99, 1065, 1066 and 1067.

The invention encompasses methods of treating prostamegaly comprising administering a therapeutically effective amount of at least one compound of formulas 47, 99, 1065, 1066 and 1067.

The invention encompasses methods of treating hyperproliferative prostatic disorders and diseases comprising administering a therapeutically effective amount of a compound of formulas 47, 99, 1065, 1066 and 1067.

The effect of the AR on the skin is apparent in the gender dimorphism and puberty related dermatological problems common to teens and early adults. The hyperandrogenism of puberty stimulates terminal hair growth, sebum production, and predisposes male teens to acne, acne vulgaris, seborrhea, excess sebum, hidradenitis suppurativa, hirsutism, hypertrichosis, hyperpilosity, androgenic alopecia, male pattern baldness, and other dermatological maladies. Although antiandrogens theoretically should prevent the hyperandrogenic dermatological diseases discussed, they are limited by toxicities, sexual side effects, and lack of efficacy when topically applied. The SARDs of this invention potently inhibit ligand-dependent and ligand-independent AR activation, and (in some cases) have short biological half-lives in the serum, suggesting that topically formulated SARDs of this invention could be applied to the areas affected by acne, seborrheic dermatitis, and/or hirsutism without risk of systemic side effects.

The invention encompasses methods of treating acne, acne vulgaris, seborrhea, seborrheic dermatitis, hidradenitis supporativa, hirsutism, hypertrichosis, hyperpilosity, or alopecia comprising administering a therapeutically effective amount of a compound of formulas 47, 99, 1065, 1066 and 1067.

The compounds and/or compositions described herein may be used for treating hair loss, alopecia, androgenic alopecia, alopecia areata, alopecia secondary to chemotherapy, alopecia secondary to radiation therapy, alopecia induced by scarring or alopecia induced by stress. Generally "hair loss" or "alopecia" refers to baldness as in the very common type of male-pattern baldness. Baldness typically begins with patch hair loss on the scalp and sometimes progresses to complete baldness and even loss of body hair. Hair loss affects both males and females.

The invention encompasses methods of treating androgenic alopecia comprising administering a therapeutically effective amount of a compound of formulas 47, 99, 1065, 1066 and 1067.

SARDs of this invention may also be useful in the treatment of hormonal conditions in females which can have hyperandrogenic pathogenesis such as precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, and/or vaginal dryness.

The invention encompasses methods of treating precocious puberty or early puberty, dysmenorrhea or amenorrhea, multilocular uterus syndrome, endometriosis, hysteromyoma, abnormal uterine bleeding, hyper-androgenic diseases (such as polycystic ovary syndrome (PCOS)), fibrocystic breast disease, fibroids of the uterus, ovarian cysts, polycystic ovary syndrome, pre-eclampsia, eclampsia of pregnancy, preterm labor, premenstrual syndrome, or vaginal dryness comprising administering a therapeutically effective amount of a compound of formulas 47, 99, 1065, 1066 and 1067.

The invention encompasses methods of treating, suppressing, reducing the incidence, reducing the severity, or inhibiting the progression of a hormonal condition in a male in need thereof, comprising administering a therapeutically effective amount of a compound of formulas 47, 99, 1065, 1066 and 1067, or its isomer, optical isomer, or any mixture of optical isomers, pharmaceutically acceptable salt, pharmaceutical product, polymorph, hydrate or any combination thereof. In one embodiment, the hormonal condition includes, but is not limited to, hypergonadism, hypersexuality, sexual dysfunction, gynecomastia, precocious puberty in a male, alterations in cognition and mood, depression, hair loss, hyperandrogenic dermatological disorders, precancerous lesions of the prostate, benign prostate hyperplasia, prostate cancer and/or other androgen-dependent cancers.

SARDs of this invention may also find utility in treatment of sexual perversion, hypersexuality, paraphilias, androgen psychosis, virilization, androgen insensitivity syndromes (AIS) (such as complete AIS (CAIS) and partial AIS (PAIS)), and improving ovulation in an animal.

The invention encompasses methods of treating sexual perversion, hypersexuality, paraphilias, androgen psychosis, virilization androgen, insensitivity syndromes, increasing or modulating or improving ovulation comprising administering a therapeutically effective amount of a compound of formulas 47, 99, 1065, 1066 and 1067.

SARDs of this invention may also be useful for treating hormone-dependent cancers such as prostate cancer, breast cancer, testicular cancer, ovarian cancer, hepatocellular carcinoma, urogenital cancer, etc. In another embodiment, the breast cancer is triple negative breast cancer. Further, local or systemic SARD administration may be useful for treatment of precursors of hormone-dependent cancers such as prostatic intraepithelial neoplasia (PIN) and atypical small acinar proliferation (ASAP).

The invention encompasses methods of treating breast cancer, testicular cancer, uterine cancer, ovarian cancer, urogenital cancer, precursors of prostate cancer, or AR related or AR expressing solid tumors, comprising administering a therapeutically effective amount of a compound of formulas 47, 99, 1065, 1066 and 1067. A precursor of prostate cancers may be prostatic intraepithelial neoplasia (PIN) or atypical small acinar proliferation (ASAP). The tumor may be hepatocellular carcinoma (HCC) or bladder cancer. Serum testosterone may be positively linked to the development of HCC. Based on epidemiologic, experimental observations, and notably the fact that men have a substantially higher risk of bladder cancer than women, androgens and/or the AR may also play a role in bladder cancer initiation.

Although traditional antiandrogens such as darolutamide, enzalutamide, apalutamide, bicalutamide and flutamide and androgen deprivation therapies (ADT) such as leuprolide were approved for use in prostate cancer, there is significant evidence that antiandrogens could also be used in a variety of other hormone-dependent and hormone-independent cancers. For example, antiandrogens have been successfully tested in breast cancer (enzalutamide; Breast Cancer Res (2014) 16(1): R7), non-small cell lung cancer (shRNAi AR), renal cell carcinoma (ASC-J9), partial androgen insensitivity associated malignancies such as gonadal tumors and seminoma, advanced pancreatic cancer (World J Gastroenterology 20(29):9229), cancer of the ovary, fallopian tubes, or peritoneum, cancer of the salivary gland (Head and Neck (2016) 38: 724-731; ADT was tested in AR-expressing recurrent/metastatic salivary gland cancers and was confirmed to have benefit on progression free survival and overall survival endpoints), bladder cancer (Oncotarget 6 (30): 29860-29876); Int J Endocrinol (2015), Article ID 384860), pancreatic cancer, lymphoma (including mantle cell), and hepatocellular carcinoma. Use of a more potent antiandrogen such as a SARD in these cancers may treat the progression of these and other cancers. Other AR-expressing cancers may also benefit from SARD treatment such as testicular cancer, uterine cancer, ovarian cancer, urogenital cancer, breast cancer, brain cancer, skin cancer, lymphoma, liver cancer, renal cancer, osteosarcoma, pancreatic cancer, endometrial cancer, lung cancer, non-small cell lung cancer (NSCLC), colon cancer, perianal adenoma, or central nervous system cancer.

SARDs of this invention may also be useful for treating other cancers containing AR such as breast, brain, skin, ovarian, bladder, lymphoma, liver, kidney, pancreas, endometrium, lung (e.g., NSCLC), colon, perianal adenoma, osteosarcoma, CNS, melanoma, hypercalcemia of malignancy and metastatic bone disease, etc.

Thus, the invention encompasses methods of treating hypercalcemia of malignancy, metastatic bone disease, brain cancer, skin cancer, bladder cancer, lymphoma, liver cancer, renal cancer, osteosarcoma, pancreatic cancer, endometrial cancer, lung cancer, central nervous system cancer, gastric cancer, colon cancer, melanoma, amyotrophic lateral sclerosis (ALS), and/or uterine fibroids comprising administering a therapeutically effective amount of a compound of formulas 47, 99, 1065, 1066 and 1067. The lung cancer may be non-small cell lung cancer (NSCLC).

SARDs of this invention may also be useful for the treating of non-hormone-dependent cancers. Non-hormone-dependent cancers include liver, salivary duct, etc.

In another embodiment, the SARDs of this invention are used for treating gastric cancer. In another embodiment, the SARDs of this invention are used for treating salivary duct carcinoma. In another embodiment, the SARDs of this invention are used for treating bladder cancer. In another embodiment, the SARDs of this invention are used for treating esophageal cancer. In another embodiment, the SARDs of this invention are used for treating pancreatic cancer. In another embodiment, the SARDs of this invention are used for treating colon cancer. In another embodiment, the SARDs of this invention are used for treating non-small cell lung cancer. In another embodiment, the SARDs of this invention are used for treating renal cell carcinoma.

AR plays a role in cancer initiation in hepatocellular carcinoma (HCC). Therefore, targeting AR may be an appropriate treatment for patients with early stage HCC. In late-stage HCC disease, there is evidence that metastasis is suppressed by androgens. In another embodiment, the SARDs of this invention are used for treating hepatocellular carcinoma (HCC).

Locati et al. in Head & Neck, 2016, 724-731 demonstrated the use of androgen deprivation therapy (ADT) in AR-expressing recurrent/metastatic salivary gland cancers and confirmed improved progression free survival and overall survival endpoints with ADT. In another embodiment, the SARDs of this invention are used for treating salivary gland cancer.

Kawahara et al. in Oncotarget, 2015, Vol 6 (30), 29860-29876 demonstrated that ELK1 inhibition, together with AR inactivation, has the potential of being a therapeutic approach for bladder cancer. McBeth et al. Int J Endocrinology, 2015, Vol 2015, Article ID 384860 suggested that the combination of antiandrogen therapy plus glucocorticoids as treatment of bladder cancer as this cancer is believed to have an inflammatory etiology. In another embodiment, the SARDs of this invention are used for treating bladder cancer, optionally in combination with glucocorticoids.

Abdominal Aortic Aneurysm (AAA)

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it is necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. J Vasc Surg (2016) 63(6): 1602-1612) showed that flutamide (50 mg/kg) or ketoconazole (150 mg/kg) attenuated AAA induced by porcine pancreatic elastase (0.35 U/mL) by 84.2% and 91.5% compared to vehicle (121%). Further AR−/− mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

Treatment of Wounds

Wounds and/or ulcers are normally found protruding from the skin or on a mucosal surface or as a result of an infarction in an organ. A wound may be a result of a soft tissue defect or a lesion or of an underlying condition. The term "wound" denotes a bodily injury with disruption of the normal integrity of tissue structures, sore, lesion, necrosis, and/or ulcer. The term "sore" refers to any lesion of the skin or mucous membranes and the term "ulcer" refers to a local defect, or excavation, of the surface of an organ or tissue, which is produced by the sloughing of necrotic tissue. "Lesion" generally includes any tissue defect. "Necrosis" refers to dead tissue resulting from infection, injury, inflammation, or infarctions. All of these are encompassed by the term "wound," which denotes any wound at any particular stage in the healing process including the stage before any healing has initiated or even before a specific wound like a surgical incision is made (prophylactic treatment).

Examples of wounds which can be treated in accordance with the present invention are aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores include, but are not limited to, bed sores, canker sores, chrome sores, cold sores, pressure sores, etc. Examples of ulcers include, but are not limited to, peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g., caused by gonorrhoea (including urethritis, endocervicitis and proctitis). Conditions related to wounds or sores which may be successfully treated according to the invention include, but are not limited to, burns, anthrax, tetanus, gas gangrene, scalatina, erysipelas, sycosis barbae, folliculitis, impetigo contagiosa, impetigo bullosa, etc. It is understood, that there may be an overlap between the use of the terms "wound" and "ulcer," or "wound" and "sore" and, furthermore, the terms are often used at random.

The kinds of wounds to be treated according to the invention include also: i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is by tissue loss, where: i) small tissue loss (due to surgical incisions, minor abrasions, and minor bites) or ii) significant tissue loss. The latter group includes ischemic ulcers, pressure sores, fistulae, lacerations, severe bites, thermal burns and donor site wounds (in soft and hard tissues) and infarctions. Other wounds include ischemic ulcers, pressure sores, fistulae, severe bites, thermal burns, or donor site wounds.

Ischemic ulcers and pressure sores are wounds, which normally only heal very slowly and especially in such cases an improved and more rapid healing is of great importance to the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

In one case, the wound to be treated is selected from the group consisting of aseptic wounds, infarctions, contused wounds, incised wounds, lacerated wounds, non-penetrating wounds, open wounds, penetrating wounds, perforating wounds, puncture wounds, septic wounds, and subcutaneous wounds.

The invention encompasses methods of treating a subject suffering from a wound comprising administering to the subject a therapeutically effective amount of a compound of formulas 47, 99, 1065, 1066 and 1067, pharmaceutically acceptable salt thereof, or a pharmaceutical composition thereof.

The invention encompasses methods of treating a subject suffering from a burn comprising administering to the subject a therapeutically effective amount of a compound of formulas 47, 99, 1065, 1066 and 1067, pharmaceutically acceptable salt thereof, or a pharmaceutical composition thereof.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process whereby the architecture and function of lost tissue are completely renewed. Repair, on the other hand, is a biological process whereby continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process which is almost always involved is the formation of a transient connective tissue in the area of tissue injury. This process starts by formation of a new extracellular collagen matrix by fibroblasts. This new extracellular collagen matrix is then the support for a connective tissue during the final healing process. The final healing is, in most tissues, a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing can be very slow and the wound may persist for an extended period of time, i.e. months or even years.

Burns are associated with reduced testosterone levels, and hypogonadism is associated with delayed wound healing. The invention encompasses methods for treating a subject suffering from a wound or a burn by administering at least one SARD compound according to this invention. The SARD may promote resolving of the burn or wound, participates in the healing process of a burn or a wound, or, treats a secondary complication of a burn or wound.

The treatment of burns or wounds may further use at least one growth factor such as epidermal growth factor (EGF), transforming growth factor-$\alpha$ (TGF-$\alpha$), platelet derived growth factor (PDGF), fibroblast growth factors (FGFs) including acidic fibroblast growth factor ($\alpha$-FGF) and basic fibroblast growth factor ($\beta$-FGF), transforming growth factor-$\beta$ (TGF-$\beta$) and insulin like growth factors (IGF-1 and IGF-2), or any combination thereof, which promote wound healing.

Wound healing may be measured by many procedures known in the art, including, but not limited to, wound tensile strength, hydroxyproline or collagen content, procollagen expression, or re-epithelialization. As an example, a SARD as described herein may be administered orally or topically at a dosage of about 0.1-100 mg per day. Therapeutic effectiveness is measured as effectiveness in enhancing wound healing as compared to the absence of the SARD compound. Enhanced wound healing may be measured by known techniques such as decrease in healing time, increase in collagen density, increase in hydroxyproline, reduction in complications, increase in tensile strength, and increased cellularity of scar tissue.

The term "reducing the pathogenesis" is to be understood to encompass reducing tissue damage, or organ damage associated with a particular disease, disorder or condition. The term may include reducing the incidence or severity of an associated disease, disorder or condition, with that in question or reducing the number of associated diseases, disorders or conditions with the indicated, or symptoms associated thereto.

Pharmaceutical Compositions

The compounds of the invention may be used in pharmaceutical compositions. As used herein, "pharmaceutical composition" means either the compound or pharmaceutically acceptable salt of the active ingredient with a pharmaceutically acceptable carrier or diluent. A "therapeutically effective amount" as used herein refers to that amount which provides a therapeutic effect for a given indication and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. The subjects may be a male or female subject or both.

Numerous standard references are available that describe procedures for preparing various compositions or formulations suitable for administration of the compounds of the invention. Examples of methods of making formulations and preparations can be found in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage form are closely related to the therapeutic amounts of the compounds or compositions which are desirable and efficacious for the given treatment application.

The pharmaceutical compositions of the invention can be administered to a subject by any method known to a person skilled in the art. These methods include, but are not limited to, orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, or intratumorally. These methods include any means in which the composition can be delivered to tissue (e.g., needle or catheter). Alternatively, a topical administration may be desired for application to dermal, ocular, or mucosal surfaces. Another method of administration is via aspiration or aerosol formulation. The pharmaceutical compositions may be administered topically to body surfaces, and are thus formulated in a form suitable for topical administration. Suitable topical formulations include gels, ointments, creams, lotions, drops and the like. For topical administrations, the compositions are prepared and applied as solutions, suspensions, or emulsions in a physiologically acceptable diluent with or without a pharmaceutical carrier.

Suitable dosage forms include, but are not limited to, oral, rectal, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterile administration, and other dosage forms for systemic delivery of active ingredients. Depending on the indication, formulations suitable for oral or topical administration are preferred.

Topical Administration:

The compounds of formulas 47, 99, 1065, 1066 and 1067 may be administered topically. As used herein, "topical administration" refers to application of the compounds of formulas 47, 99, 1065, 1066 and 1067 (and optional carrier) directly to the skin and/or hair. The topical composition can be in the form of solutions, lotions, salves, creams, ointments, liposomes, sprays, gels, foams, roller sticks, and any other formulation routinely used in dermatology.

Topical administration is used for indications found on the skin, such as hirsutism, alopecia, acne, and excess sebum. The dose will vary, but as a general guideline, the compound will be present in a dermatologically acceptable carrier in an amount of from about 0.01 to 50 w/w %, and more typically from about 0.1 to 10 w/w %. Typically, the dermatological preparation will be applied to the affected area from 1 to 4 times daily. "Dermatologically acceptable" refers to a carrier which may be applied to the skin or hair, and which will allow the drug to diffuse to the site of action. More specifically "site of action", it refers to a site where inhibition of androgen receptor or degradation of the androgen receptor is desired.

The compounds of formulas 47, 99, 1065, 1066 and 1067, may be used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for the balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds of formulas 47, 99, 1065, 1066 and 1067 will most typically be used to alleviate androgenic alopecia, the compounds may be used to alleviate any type of alopecia. Examples of non-androgenic alopecia include, but are not limited to, alopecia areata, alopecia due to radiotherapy or chemotherapy, scarring alopecia, or stress related alopecia.

The compounds of formulas 47, 99, 1065, 1066 and 1067 can be applied topically to the scalp and hair to prevent, or treat balding. Further, the compound of formulas 47, 99, 1065, 1066 and 1067 can be applied topically in order to induce or promote the growth or regrowth of hair on the scalp.

The invention also encompasses topically administering a compound of formula 47, 99, 1065, 1066 and 1067 to treat or prevent the growth of hair in areas where such hair growth in not desired. One such use will be to alleviate hirsutism. Hirsutism is excessive hair growth in areas that typically do not have hair (e.g., a female face). Such inappropriate hair growth occurs most commonly in women and is frequently seen at menopause. The topical administration of the compounds of formulas 47, 99, 1065, 1066 and 1067 will alleviate this condition leading to a reduction, or elimination of this inappropriate, or undesired, hair growth.

The compounds of formulas 47, 99, 1065, 1066 and 1067 may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the luminal duct so that it may be deposited on the surface of the skin.

In some individuals, an excessive quantity of sebum is secreted onto the skin. This can have a number of adverse consequences. It can exacerbate acne, since sebum is the primary food source for *Propionbacterium acnes*, the causative agent of acne. It can cause the skin to have a greasy appearance, typically considered cosmetically unappealing.

Formation of sebum is regulated by growth factors and a variety of hormones including androgens. The cellular and molecular mechanism by which androgens exert their influence on the sebaceous gland has not been fully elucidated. However, clinical experience documents the impact androgens have on sebum production. Sebum production is significantly increased during puberty, when androgen levels are their highest. The compounds of formulas 47, 99, 1065, 1066 and 1067 inhibit the secretion of sebum and thus reduce the amount of sebum on the surface of the skin. The compounds of formulas 47, 99, 1065, 1066 and 1067 can be used to treat a variety of dermal diseases such as acne or seborrheic dermatitis.

In addition to treating diseases associated with excess sebum production, the compounds of formulas 47, 99, 1065, 1066 and 1067 can also be used to achieve a cosmetic effect. Some consumers believe that they are afflicted with overactive sebaceous glands. They feel that their skin is oily and thus unattractive. These individuals may use the compounds of formulas 47, 99, 1065, 1066 and 1067 to decrease the amount of sebum on their skin. Decreasing the secretion of sebum will alleviate oily skin in individuals afflicted with such conditions.

To treat these topical indications, the invention encompasses cosmetic or pharmaceutical compositions (such as dermatological compositions), comprising at least one of the compounds of formulas 47, 99, 1065, 1066 and 1067. Such dermatological compositions will contain from 0.001% to 10% w/w % of the compound(s) in admixture with a dermatologically acceptable carrier, and more typically, from 0.1 to 5 w/w % of the compounds. Such compositions will typically be applied from 1 to 4 times daily. The reader's attention is directed to Remington's Pharmaceutical Science, Edition 17, Mark Publishing Co., Easton, Pa. for a discussion of how to prepare such formulations.

The compositions of the invention may also include solid preparations such as cleansing soaps or bars. These compositions are prepared according to methods known in the art.

Formulations such as aqueous, alcoholic, or aqueous-alcoholic solutions, or creams, gels, emulsions or mousses, or aerosol compositions with a propellant may be used to treat indications that arise where hair is present. Thus, the composition can also be a hair care composition. Such hair care compositions include, but are not limited to, shampoo, a hair-setting lotion, a treating lotion, a styling cream or gel, a dye composition, or a lotion or gel for preventing hair loss. The amounts of the various constituents in the dermatological compositions are those conventionally used in the fields considered.

Medicinal and cosmetic agents containing the compounds of formulas 47, 99, 1065, 1066 and 1067 will typically be packaged for retail distribution (i.e., an article of manufacture). Such articles will be labeled and packaged in a manner to instruct the patient how to use the product. Such instructions will include the condition to be treated, duration of treatment, dosing schedule, etc.

Antiandrogens, such as finasteride or flutamide, have been shown to decrease androgen levels or block androgen action in the skin to some extent but suffer from undesirable systemic effects. An alternative approach is to topically apply a selective androgen receptor degrader (SARD) compound to the affected areas. Such SARD compound would exhibit potent but local inhibition of AR activity, and local degradation of the AR, would not penetrate to the systemic circulation of the subject, or would be rapidly metabolized upon entry into the blood, limiting systemic exposure.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Oral and Parenteral Administration:

In preparing the compositions in oral dosage form, any of the usual pharmaceutical media may be employed. Thus, for liquid oral preparations, such as, suspensions, elixirs, and solutions, suitable carriers and additives include water, glycols, oils, alcohols, flavoring agents, preservatives, coloring agents, and the like. For solid oral preparations such as, powders, capsules, and tablets, suitable carriers and additives include starches, sugars, diluents, granulating agents, lubricants, binders, disintegrating agents, and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients may be included, such as ingredients that aid solubility or for preservation. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Methods of treatment using formulations suitable for oral administration may be presented as discrete units such as capsules, cachets, tablets, or lozenges, each containing a predetermined amount of the active ingredient. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more ingredient selected from diluents, buffers, flavoring agents, binders, disintegrants, surface active agents, thickeners, lubricants, preservatives (including antioxidants), and the like.

The formulations may be of immediate release, sustained release, delayed-onset release or any other release profile known to one skilled in the art.

For administration to mammals, and particularly humans, it is expected that the physician will determine the actual dosage and duration of treatment, which will be most suitable for an individual and can vary with the age, weight, genetics and/or response of the particular individual.

The methods of the invention comprise administration of a compound at a therapeutically effective amount. The therapeutically effective amount may include various dosages.

In one embodiment, a compound of this invention is administered at a dosage of 1-3000 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 100-250 mg per day, 125-300 mg per day, 20-50 mg per day, 5-50 mg per day, 200-500 mg per day, 125-500 mg per day, 500-1000 mg per day, 200-1000 mg per day, 1000-2000 mg per day, 1000-3000 mg per day, 125-3000 mg per day, 2000-3000 mg per day, 300-1500 mg per day or 100-1000 mg per day. In one embodiment, a compound of this invention is administered at a dosage of 25 mg per day. In one embodiment, a compound of this invention is administered at a dosage of 40 mg per day. In one embodiment, a compound of this invention is administered at a dosage of 50 mg per day. In one embodiment, a compound of this invention is administered at a dosage of 67.5 mg per day. In one embodiment, a compound of this invention is administered at a dosage of 75 mg per day. In one embodiment, a compound of this invention is administered at a dosage of 80 mg per day. In one embodiment, a compound of this invention is administered at a dosage of 100 mg per day. In one embodiment, a compound of this invention is administered at a dosage of 125 mg per day. In one embodiment, a compound of this invention is administered at a dosage of 250 mg per day. In one embodiment, a compound of this invention is administered at a dosage of 300 mg per day. In one embodiment, a compound of this invention is administered at a dosage of 500 mg per day. In one embodiment, a compound of this invention is administered at a dosage of 600 mg per day. In one embodiment, a compound of this invention is administered at a dosage of 1000 mg per day. In one embodiment, a compound of this invention is administered at a dosage of 1500 mg per day. In one embodiment, a compound of this invention is administered at a dosage of 2000 mg per day. In one embodiment, a compound of this invention is administered at a dosage of 2500 mg per day. In one embodiment, a compound of this invention is administered at a dosage of 3000 mg per day.

The methods may comprise administering a compound at various dosages. For example, the compound may be administered at a dosage of 3 mg, 10 mg, 30 mg, 40 mg, 50 mg, 80 mg, 100 mg, 120 mg, 125 mg, 200 mg, 250 mg, 300 mg, 450 mg, 500 mg, 600 mg, 900 mg, 1000 mg, 1500 mg, 2000 mg, 2500 mg or 3000 mg.

Alternatively, the compound may be administered at a dosage of 0.1 mg/kg/day. The compound may administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day, 30 mg/kg/day, 50 mg/kg/day or 100 mg/kg/day.

The pharmaceutical composition may be a solid dosage form, a solution, or a transdermal patch. Solid dosage forms include, but are not limited to, tablets and capsules.

The following examples are presented in order to more fully illustrate the preferred embodiments of the invention. They should in no way, however, be construed as limiting the broad scope of the invention.

EXAMPLES

Example 1

Synthesis of SARDs

Synthesis of (S)-3-(4-cyano-1H-pyrazol-1-yl)-N-(6-cyano-5-(trifluoromethyl)pyridin-3-yl)-2-hydroxy-2-methylpropanamide (1065)

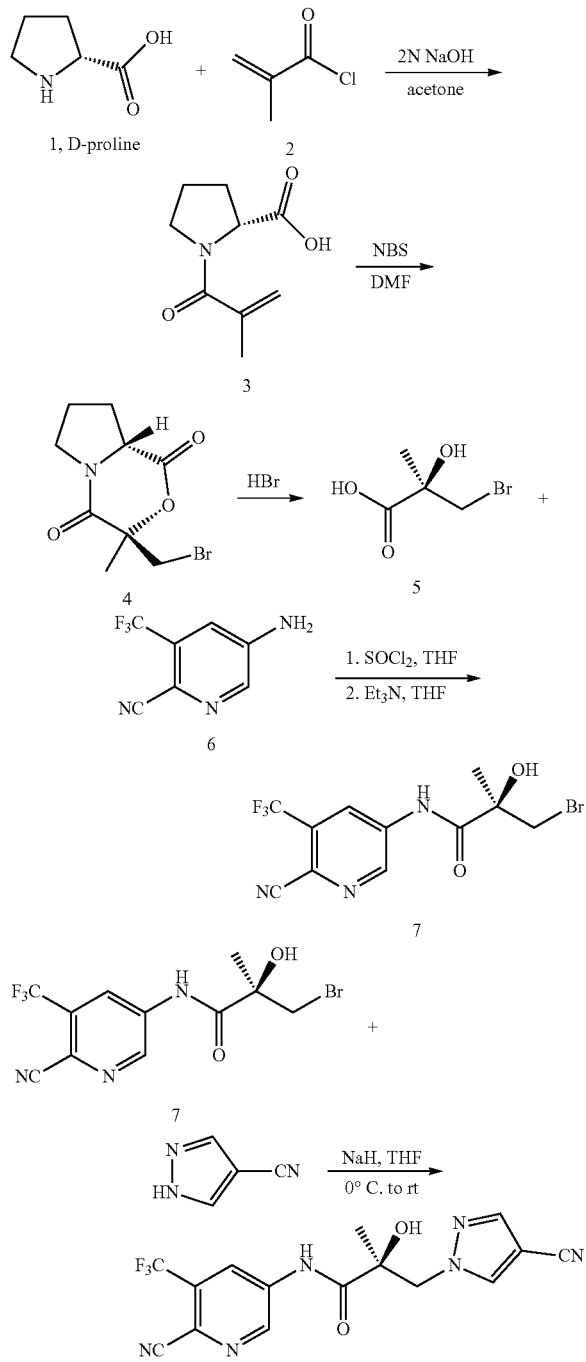

(2R)-1-Methacryloylpyrrolidin-2-carboxylic Acid (3)

D-Proline (14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (2, 13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded the designed compound (3, 16.2 g, 68%) as colorless crystals: mp 102-103° C. (lit. mp 102.5-103.5° C.); the NMR spectrum of this compound demonstrated the existence of two rotamers of the titled compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$+80.8° (c=1, MeOH); Anal. Calcd. for $C_9H_{13}NO_3$: C, 59.00; H, 7.15; N, 7.65. Found: C, 59.13; H, 7.19; N, 7.61.

(3R,8aR)-3-Bromomethyl-3-methyl-tetrahydro-pyrrolo[2,1-c][1,4]oxazine-1,4-dione (4)

A solution of NBS (23.5 g, 0.132 mol) in 100 mL of DMF was added dropwise to a stirred solution of the (methylacryloyl)-pyrrolidine (3, 16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried ~34%) of the titled compound as a yellow solid: mp 152-154° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$+124.5° (c=1.3, chloroform); Anal. Calcd. for $C_9H_{12}BrNO_3$: C, 41.24; H, 4.61; N, 5.34. Found: C, 41.46; H, 4.64; N, 5.32.

(2R)-3-Bromo-2-hydroxy-2-methylpropanoic Acid (5)

A mixture of bromolactone (4, 18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 107-109° C. (lit. mp 109-113° C. for the S-isomer); $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; [α]$_D^{26}$+10.5° (c=2.6, MeOH); Anal. Calcd. for C$_4$H$_7$BrO$_3$: C, 26.25; H, 3.86. Found: C, 26.28; H, 3.75.

(R)-3-Bromo-N-(6-cyano-5-(trifluoromethyl)pyridin-3-yl)-2-hydroxy-2-methylpropanamide (7)

Thionyl chloride (0.8 mL, 1.07 mol) was added dropwise to a cooled solution (less than 4° C.) of (R)-3-bromo-2-hydroxy-2-methylpropanoic acid (5, 1.27 g, 6.94 mmol) in 50 mL of THF under an argon atmosphere. The resulting mixture was stirred for 3 h under the same condition. To this was added Et$_3$N (1.8 mL, 1.28 mmol) and stirred for 20 min under the same condition. After 20 min, 5-amino-3-(trifluoromethyl)picolinonitrile (6, 1 g, 5.34 mmol) in 50 mL of THF were added and then the mixture was allowed to stir overnight at room temperature. The solvent was removed under reduced pressure to give a solid which was treated with 50 mL of H$_2$O, extracted with EtOAc (2×400 mL). The combined organic extracts were washed with saturated NaHCO$_3$ solution (2×50 mL) and brine (50 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 1.32 g (70.2%) of (R)-3-bromo-N-(6-cyano-5-(trifluoromethyl)pyridin-3-yl)-2-hydroxy-2-methylpropanamide (7) as a light-yellow solid. MS (ESI) m/z 351.08 [M−H]$^-$. $^1$H NMR (CDCl$_3$, 400 MHz) δ 9.15 (bs, 1H, NH), 8.90 (s, 1H), 8.78 (s, 1H), 4.02 (d, J=10.8 Hz, 1H), 3.60 (d, J=10.8 Hz, 1H), 3.17 (bs, 1H, OH), 1.66 (s, 3H).; $^{19}$F NMR (CDCl$_3$, 400 MHz) δ −62.09.

(S)-3-(4-Cyano-1H-pyrazol-1-yl)-N-(6-cyano-5-(trifluoromethyl)pyridin-3-yl)-2-hydroxy-2-methylpropanamide (1065)

To a dry, nitrogen-purged 100 mL round-bottom flask equipped a dropping funnel under argon atmosphere, NaH of 60% dispersion in mineral oil (511 mg, 12.8 mmol) was added in 60 mL of anhydrous THF solvent in the flask at ice-water bath, and 4-cyano-1H-pyrazole (8, 465 mg, 4.26 mmol) was stirred 30 min at the ice-water bath. Into the flask, the solution of (R)-3-bromo-N-(6-cyano-5-(trifluoromethyl)pyridin-3-yl)-2-hydroxy-2-methylpropanamide (7, 1.5 g, 4.26 mmol) in 5 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=3/4 (v/v) to produce the designed compound (1065) as white solid.

Yield 54%; UV max 195.45, 274.45; MS (ESI) m/z 363.1 [M−H]$^-$; 365.0 [M+H]$^+$; HRMS (ESI) m/z calcd for C$_{15}$H$_{11}$F$_3$N$_6$O$_2$ 365.0974 [M+H]$^+$ found 365.0931 [M+H]$^+$ 387.0754 [M+Na]$^+$; $^1$H NMR (CDCl$_3$, 400 MHz) δ 9.17 (bs, 1H, NH), 8.83 (s, 1H), 8.67 (d, J=1.6 Hz, 1H), 7.92 (s, 1H), 7.85 (s, 1H), 5.58 (s, OH), 4.73 (d, J=14.0 Hz, 1H), 4.34 (d, J=14.0 Hz, 1H), 1.53 (s, 3H); $^{19}$F NMR (CDCl$_3$, decoupled) δ −62.11; Assigned by NOESY and COSY.

Synthesis of (S)—N-(6-Cyano-5-(trifluoromethyl)pyridin-3-yl)-3-(5-fluoro-1H-indol-1-yl)-2-hydroxy-2-methylpropanamide (47)

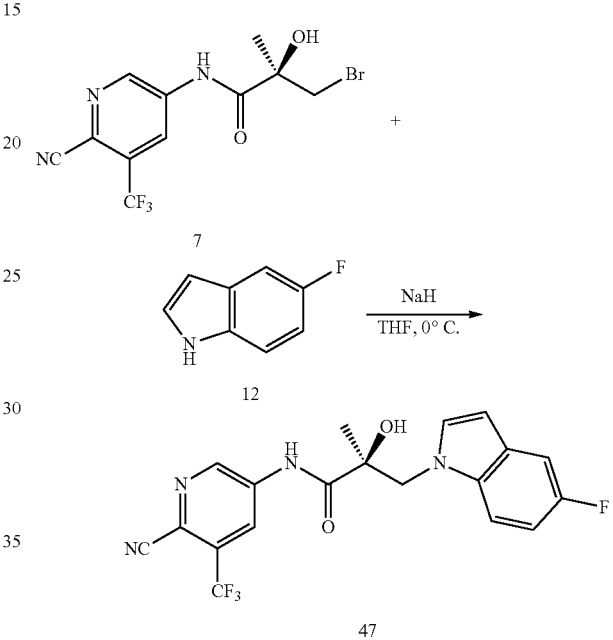

To a dry, nitrogen-purged 50 mL round-bottom flask equipped a dropping funnel under argon atmosphere, NaH of 60% dispersion in mineral oil (80 mg, 2.0 mmol) was added in 5 mL of anhydrous THF solvent in the flask at ice-water bath, and 5-fluoro-1H-indole (12, 154 mg, 1.0 mmol) was stirred 30 min at the ice-water bath. Into the flask, (R)-3-bromo-N-(6-cyano-5-(trifluoromethyl)pyridin-3-yl)-2-hydroxy-2-methylpropanamide (7, 352 mg, 1.0 mmol) in 5 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=2/3 to produce the designed compound (47) as white solid. Yield 83%; MS (ESI) m/z 407.20 [M+H]$^+$; 405.02 [M−H]$^-$; HRMS (ESI) m/z calcd for C$_{19}$H$_{14}$F$_4$N$_4$O$_2$ 407.1131 [M+H]$^+$ found 407.1128 [M+H]$^+$; $^1$H NMR (CDCl$_3$, 400 MHz) δ 8.85 (bs, 1H, NH), 8.58 (d, J=2.0 Hz, 1H), 8.51 (s, 1H), 7.33 (dd, J=8.8, 4.0 Hz, 1H), 7.19 (d, J=2.4 Hz, 1H), 7.17 (d, J=2.8 Hz, 1H), 6.92 (m, 1H), 6.45 (d, J=2.8 Hz, 1H), 4.64 (d, J=15.2 Hz, 1H), 4.33 (d, J=15.2 Hz, 1H), 2.93 (bs, 1H, OH), 1.64 (s, 3H);

$^{19}$F NMR (CDCl$_3$, 400 MHz) δ −82.08, −156.13; Assigned by NOESY and COSY.

Synthesis of (S)—N-(6-Cyano-5-(trifluoromethyl)pyridin-3-yl)-3-(3,5-difluoro-1H-indazol-1-yl)-2-hydroxy-2-methylpropanamide (99)

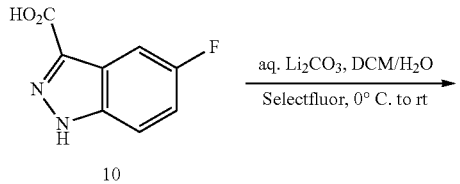

3,5-Difluoro-1H-indazole (11)

To a 50 mL round-bottle flask with a magnetic stirring bar were added Selectfluor® (872 mg, 2.0 mmol, 2.0 equiv), Li$_2$CO$_3$ (296 mg, 4.0 mmol, 4.0 equiv), dichloromethane (3.3 mL) and water (1.7 mL). Then carboxylic acid 10 (1.0 mmol, 1.0 equiv) was added. The reaction mixture was stirred for 2 h in ice bath. The reaction mixture was diluted with water (40 mL), followed by extracting with DCM (20 mL×2). The combined organic extracts were washed with brine, dried over anhydrous sodium sulfate and concentrated in vacuo. The crude product was purified by flash column chromatography (n-hexane:DCM=2:1) to afford the desired product (11) as white solid.

Yield 48%;

MS (ESI) m/z 154.8 [M+H]$^+$;

$^1$H NMR (CDCl$_3$, 400 MHz) δ 9.80 (bs, 1H, NH), 7.37 (dt, J=8.8, 2.4 Hz, 1H), 7.31 (dd, J=8.0, 1.6 Hz, 1H), 7.23 (td, J=8.8, 2.0 Hz, 1H);

$^{19}$F NMR (CDCl$_3$, decoupled) δ −121.46, −133.92.

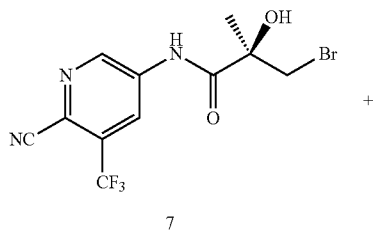

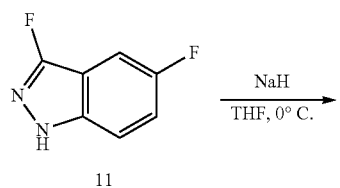

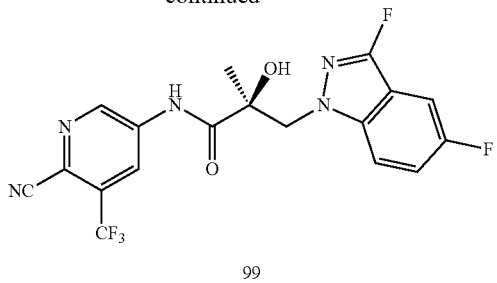

99

To a dry, nitrogen-purged 50 mL round-bottom flask equipped a dropping funnel under argon atmosphere, NaH of 60% dispersion in mineral oil (15 mg, 0.36 mmol) was added in 5 mL of anhydrous THF solvent in the flask at ice-water bath, and 3,5-difluoro-1H-indazole (11, 27 mg, 0.18 mmol) was stirred 30 min at the ice-water bath. Into the flask, (R)-3-bromo-N-(6-cyano-5-(trifluoromethyl)pyridin-3-yl)-2-hydroxy-2-methylpropanamide (7, 62 mg, 0.18 mmol) in 5 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=2/3 to produce the designed compound (99) as white solid.

Yield 56%;

MS (ESI) m/z 424.18 [M−H]$^-$; 426.22 [M+H]$^+$;

HRMS (ESI) m/z calcd for C$_{18}$H$_{12}$F$_5$N$_5$O$_2$ 426.0989 [M+H]$^+$ found 426.0997 [M+H]$^+$;

$^1$H NMR (CDCl$_3$, 400 MHz) δ 9.20 (bs, 1H, NH), 8.79 (s, 1H), 8.55 (s, 1H), 7.41 (s, 1H), 7.26 (m, 2H), 5.41 (bs, 1H, OH), 4.82 (d, J=12.4 Hz, 1H), 4.29 (d, J=12.4 Hz, 1H), 1.54 (s, 3H);

$^{19}$F NMR (CDCl$_3$, decoupled) δ −85.46, −156.21, −175.96.

Synthesis of (S)-3-(3-Bromo-4-chloro-1H-pyrazol-1-yl)-N-(4-cyano-3-(trifluoromethyl)phenyl)-2-hydroxy-2-methylpropanamide (1066)

To a solution of 3-bromo-4-chloro-pyrazole (0.20 g, 0.0011024 mol) in anhydrous THF (10 mL), which was cooled in an ice water bath under an argon atmosphere, was added sodium hydride (60% dispersion in oil, 0.154 g, 0.0038585 mol). After addition, the resulting mixture was stirred for three hours. (R)-3-Bromo-N-(4-cyano-3-(trifluoromethyl)phenyl)-2-hydroxy-2-methylpropanamide (0.387 g, 0.0011024 mol) was added to above solution, and the resulting reaction mixture was allowed to stir overnight at room temperature under argon. The reaction was quenched by water, and extracted with ethyl acetate. The organic layer was washed with brine, dried with MgSO$_4$, filtered, and concentrated under vacuum. The product was purified by a silica gel column using DCM and ethyl acetate (95:5) as eluent to afford 0.25 g (50%) of the titled compound as white solid.

$^1$H NMR (400 MHz, DMSO-d$_6$) δ 10.34 (s, 1H, NH), 8.41 (s, 1H, ArH), 8.20 (d, J=8.8 Hz, 1H, ArH), 8.11 (d, J=8.8 Hz, 1H, ArH), 7.93 (s, 1H, Pyrazole-H), 6.39 (s, 1H, OH), 4.43 (d, J=14.0 Hz, 1H, CH), 4.25 (d, J=14.0 Hz, 1H, CH), 1.38 (s, 3H, CH$_3$).

HRMS [$C_{15}H_{12}BrClF_3N_4O_2^+$]: calcd 450.9784, found 450.9807 [M+H]+. Purity: 96.55% (HPLC).

Synthesis of (S)-3-(5-Bromo-4-chloro-1H-pyrazol-1-yl)-N-(4-cyano-3-(trifluoromethyl)phenyl)-2-hydroxy-2-methylpropanamide (1067)

To a solution of 5-bromo-4-chloro-pyrazole (0.20 g, 0.0011024 mol) in anhydrous THF (10 mL), which was cooled in an ice water bath under an argon atmosphere, was added sodium hydride (60% dispersion in oil, 0.154 g, 0.0038585 mol). After addition, the resulting mixture was stirred for three hours. (R)-3-Bromo-N-(4-cyano-3-(trifluoromethyl)phenyl)-2-hydroxy-2-methylpropanamide (0.387 g, 0.0011024 mol) was added to above solution, and the resulting reaction mixture was allowed to stir overnight at room temperature under argon. The reaction was quenched by water, and extracted with ethyl acetate. The organic layer was washed with brine, dried with $MgSO_4$, filtered, and concentrated under vacuum. The product was purified by a silica gel column using DCM and ethyl acetate (95:5) as eluent to afford 62 mg (12%) of the titled compound as white solid.

$^1$H NMR (400 MHz, DMSO-$d_6$) δ 10.39 (s, 1H, NH), 8.49 (s, 1H, ArH), 8.26 (d, J=8.6 Hz, 1H, ArH), 8.11 (d, J=8.6 Hz, 1H, ArH), 7.71 (s, 1H, Pyrazole-H), 6.37 (s, 1H, OH), 4.48 (d, J=14.4 Hz, 1H, CH), 4.34 (d, J=14.4 Hz, 1H, CH), 1.43 (s, 3H, $CH_3$).
(ESI, Positive): 451.01 [M+Na]$^+$.

Example 2

Androgen Receptor Binding, Transactivation, Degradation, and Metabolism of SARDs Ligand Binding Assay Objective:
To determine SARDs binding affinity to the AR-LBD.
Method:
hAR-LBD (633-919) was cloned into pGex4t. 1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-2}$M) were incubated with [$^3$H]mibolerone and AR LBD using the conditions described above. Following incubation, the ligand bound AR-LBD complex was isolated using Bio Gel HT® hydroxyapatite, washed and counted in a scintillation counter after adding scintillation cocktail. Values are expressed as $K_i$.
Transactivation Assay with Wt AR
Objective:
To determine the effect of SARDs on androgen-induced transactivation of AR wildtype (wt).

Method:
HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) using Lipofectamine transfection reagent in optiMEM medium. Medium was changed 24 h after transfection to DME+5% csFBS without phenol red and treated with a dose response of various drugs (1 pM to 10 μM). SARDs and antagonists were treated in combination with 0.1 nM R1881. Luciferase assay was performed 24 h after treatment on a Biotek synergy 4 plate reader. Firefly luciferase values were normalized to renilla luciferase values.
Plasmid Constructs and Transient Transfection.
Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 μg GRE-LUC, 0.01 μg CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.
LNCaP Gene Expression Assay.
Method: LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.
LNCaP Growth Assay.
Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.
LNCaP or AD1 Degradation (AR FL).
Method: LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 μM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.
22RV1 and D567es Degradation (AR SV).
Method:
22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 Growth and Gene Expression.

Methods:

Cell growth was evaluated as described before by SRB assay. Cells were plated in a 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Determination of Metabolic Stability (In Vitro $CL_{int}$) of Test Compounds

Phase I Metabolism

The assay was done in a final volume of 0.5 ml in duplicates (n=2). Test compound (1 11M) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 μl aliquots were removed and quenched with 100 μl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (μl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

LC-MS/NIS Analysis

The analysis of the compounds under investigation was performed using LC-MS/MS system consisting of Agilent 1100 HPLC with an MDS/Sciex 4000 Q-Trap™ mass spectrometer. The separation was achieved using a C18 analytical column (Alltima™, 2.1×100 mm, 3 μm) protected by a C18 guard cartridge system (SecurityGuard™ ULTRA Cartridges UHPLC for 4.6 mm ID columns, Phenomenex). Mobile phase was consisting of channel A (95% acetonitrile+5% water +0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage of −4200 V (negative mode). Declustering potential, entrance potential, collision energy, product ion mass, and cell exit potential were optimized for each compound.

LC-MS/MS Analysis for Determining Rat Serum Concentrations

Serum was collected 24-30 hours after last dose. 100 μL of serum was mixed with 200 μL of acetonitrile/internal standard. Standard curves were prepared by serial dilution of standards in nM with 100 μL of rat serum, concentrations were 1000, 500, 250, 125, 62.5, 31.2, 15.6, 7.8, 3.9, 1.9, 0.97, and 0. Standards were with extracted with 200 μL of acetonitrile/internal standard. The internal standard for these experiments was (S)-3-(4-cyanophenoxy)-N-(3-(chloro)-4-cyanophenyl)-2-hydroxy-2-methylpropanamide.

The instrumental analysis of the analyte SARD was performed using LC-MS/MS system consisting of Agilent 1100 HPLC with an MDS/Sciex 4000 Q-Trap™ mass spectrometer. The separation was achieved using a C18 analytical column (Alltima™, 2.1×100 mm, 3 μm) protected by a C18 guard column (Phenomenex™ 4.6 mm ID cartridge with holder). Mobile phase was consisting of channel A (95% acetonitrile+5% water+0.1% formic acid) and channel C (95% water+5% acetonitrile+0.1% formic acid) and was delivered isocratically at a flow rate of 0.4 mL/min at 70% A and 30% B. The total runtime for analyte SARD was optimized but generally 2-4 minutes, and the volume injected was 10 μL. Multiple reaction monitoring (MRM) scans were made with curtain gas at 10; collision gas at medium; nebulizer gas at 60.0 and auxiliary gas at 60.0 and source temperature at 550° C. Molecular ions were formed using an ion spray voltage (IS) of 4200 (negative mode). Declustering potential (DP), entrance potential (EP), collision energy (CE), product ion mass, and cell exit potential (CXP) were optimized for each analyte SARD for the mass pair observed.

Log P: Octanol-Water Partition Coefficient (Log P)

Log P is the log of the octanol-water partition coefficient, commonly used early in drug discovery efforts as a rough estimate of whether a particular molecule is likely to cross biological membranes. Log P was calculated using ChemDraw Ultra version is 12.0.2.1016 (Perkin-Elmer, Waltham, Mass. 02451). Calculated Log P values are reported in Table 1 in the column labeled 'Log P (−0.4 to +5.6)'. Lipinski's rule of five is a set of criteria intended to predict oral bioavailability. One of these criteria for oral bioavailability is that the Log P is between the values shown in the column heading (−0.4 (relatively hydrophilic) to +5.6 (relatively lipophilic) range), or more generally stated <5. One of the goals of SARD design was to improve water solubility. The monocyclic templates of this invention such as the pyrazoles, pyrroles, etc. were more water soluble than earlier analogs. For instance, one may compare the Log P values of SARDs from other templates, e.g., compounds 47, 99, 1065-1067.

TABLE 1

In vitro screening of LBD binding ($K_i$), AR antagonism ($IC_{50}$), SARD activity, and metabolic stability

| Compound # | Structure | Log P (−0.4 to +5.6) | M.W. | wtAR Binding ($K_i$ (left)) & Transactivation ($IC_{50}$ (right)) (nM) | | SARD Activity (% inh): Full Length (left) and S.V. (right) | | DMPK (MLM) $T_{1/2}$ (min) & $CL_{int}$ (μL/min/mg) |
|---|---|---|---|---|---|---|---|---|
| | | | | $K_i$ (nM) (DHT = 1 nM) | $IC_{50}$ (nM) | Full Length % inhibition at 1, 10 μM | S.V. % inhibition at 10 μM | |
| Enobosarm (agonist) | F₃C-...-OH ...NC...CN | 3.44 | 389.89 | 20.21 | ~20 ($EC_{50}$) | Not applicable | Not applicable | |

TABLE 1-continued

In vitro screening of LBD binding (K$_i$), AR antagonism (IC$_{50}$), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (μL/min/mg) |
|---|---|---|---|---|---|---|---|---|
| | | | | K$_i$ (nM) (DHT = 1 nM) | IC$_{50}$ (nM) | Full Length % inhibition at 1, 10 μM | S.V. % inhibition at 10 μM | |
| R-Bicalutamide | 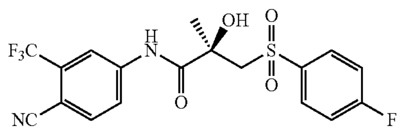 [SMILES: C[C@](O)(CS(=O)(=O)c1ccc(F)cc1)C(=O)Nc1ccc(C#N)c(C(F)(F)F)c1] | 2.57 | 430.37 | 508.84 | 248.2 | 0 | 0 | |
| Enzalutamide | 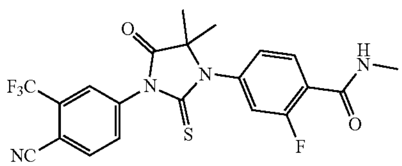 [SMILES: CNC(=O)c1ccc(N2C(=S)N(c3ccc(C#N)c(C(F)(F)F)c3)C(=O)C2(C)C)cc1F] | 4.56 | 464.44 | 3641.29 | 216.3 | 0 | 0 | |
| ARN-509 (Apalutamide) | 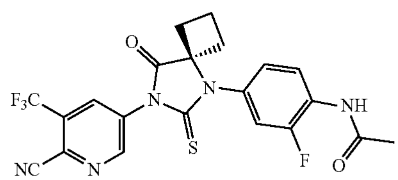 | 3.47 | 477.43 | 1452.29 | | 0 | 0 | |
| 17 | 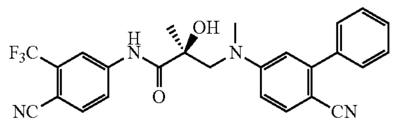 [SMILES: CN(C[C@](C)(O)C(=O)Nc1ccc(C#N)c(C(F)(F)F)c1)c1ccc(C#N)c(-c2ccccc2)c1] | 5.69 | 478.48 | 28.4 | 95 | | | |
| 1002 | 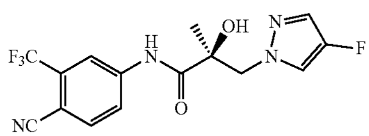 [SMILES: C[C@](O)(Cn1cc(F)cn1)C(=O)Nc1ccc(C#N)c(C(F)(F)F)c1] | 2.03 | 356.27 | No binding | 199.36 | 100 | 100 | 77.96 0.89 |
| 11 | 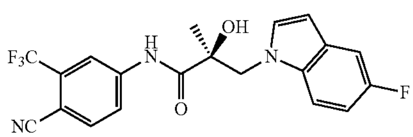 [SMILES: C[C@](O)(Cn1ccc2cc(F)ccc21)C(=O)Nc1ccc(C#N)c(C(F)(F)F)c1] | 3.47 | 405.35 | 267.39 | 85.10 | 65-83 | 60-100 | 12.35 56.14 |
| 1002 tartarate (1002 Tart.) | | | 506.36 | | 125.2 | | | |
| 1017 | 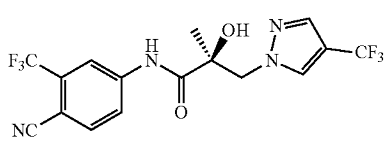 [SMILES: C[C@](O)(Cn1cc(C(F)(F)F)cn1)C(=O)Nc1ccc(C#N)c(C(F)(F)F)c1] | 2.79 | 406.28 | 898.23 | 71.2 | 80 | 100 | Infinity 0 |
| 1022 | 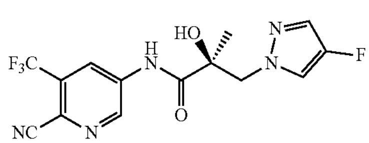 [SMILES: C[C@](O)(Cn1cc(F)cn1)C(=O)Nc1cnc(C#N)c(C(F)(F)F)c1] | 1.11 | 357.26 | No binding | 62.2 | 54 | 81 | |

TABLE 1-continued

In vitro screening of LBD binding (K$_i$), AR antagonism (IC$_{50}$), SARD activity, and metabolic stability

| Compound # | Structure | Log P (−0.4 to + 5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (μL/min/mg) |
|---|---|---|---|---|---|---|---|---|
| | | | | K$_i$ (nM) (DHT = 1 nM) | IC$_{50}$ (nM) | Full Length % inhibition at 1, 10 μM | S.V. % inhibition at 10 μM | |
| 1045 | | 3.73 | 433.36 | No binding | 383.3 | 84% | | |
| 1048 | | 1.90 | 363.29 | 1499 | 44.5 | 90 | 100 | |
| 1049 | | 2.43 | 372.73 | >10000 | 135.7 | 71 | 34 | |
| 1058 | | 3.32 | 435.17 | 606.5 | 83.7 | 70 | 80 | |
| 1065 | | 3.14 | 451.63 | | 59.4 | 17, +15 | | |
| 1066 | | 3.66 | 451.63 | 4934.871 | 138.2 | | | |
| 1067 | | 3.14 | 451.63 | | | 61, 86 | | |
| 47 | | 2.55 | 406.33 | 757.29032 | 20.68 | 57, 97 | | |

TABLE 1-continued

In vitro screening of LBD binding ($K_i$), AR antagonism ($IC_{50}$), SARD activity, and metabolic stability

| Compound # | Structure | Log P (−0.4 to +5.6) | M.W. | wtAR Binding ($K_i$ (left)) & Transactivation ($IC_{50}$ (right)) (nM) | | SARD Activity (% inh): Full Length (left) and S.V. (right) | | DMPK (MLM) $T_{1/2}$ (min) & $CL_{int}$ (μL/min/mg) |
|---|---|---|---|---|---|---|---|---|
| | | | | $K_i$ (nM) (DHT = 1 nM) | $IC_{50}$ (nM) | Full Length % inhibition at 1, 10 μM | S.V. % inhibition at 10 μM | |
| 99 | [Structure] | 2.79 | 425.31 | 0.00 | 26.74 | 66, 78 | | |

Example 3

In Vitro AR Antagonism

Figure 1B:
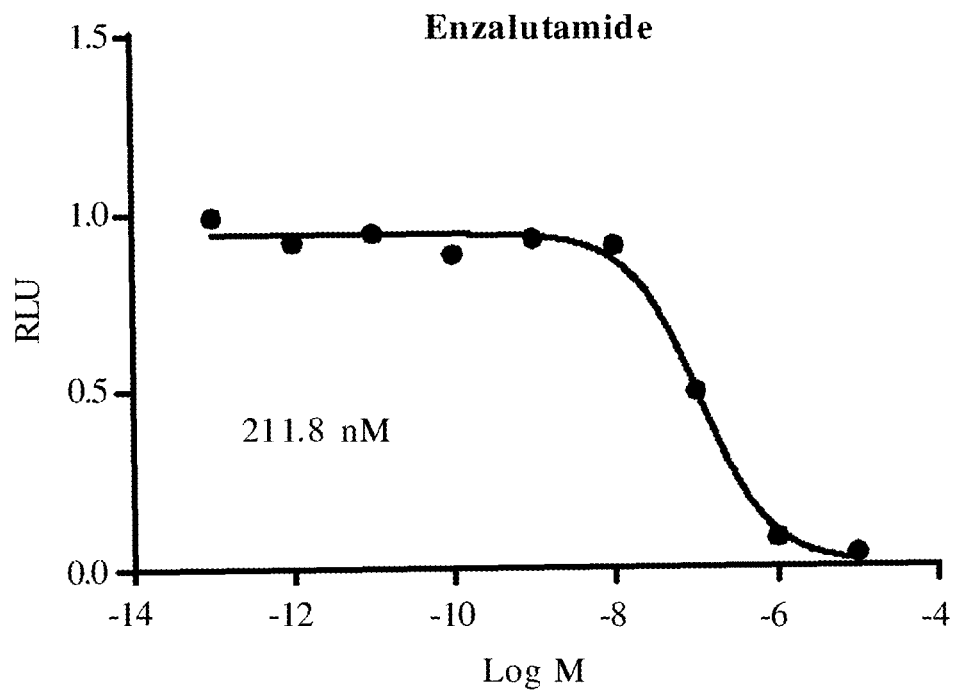
Figure 1C:
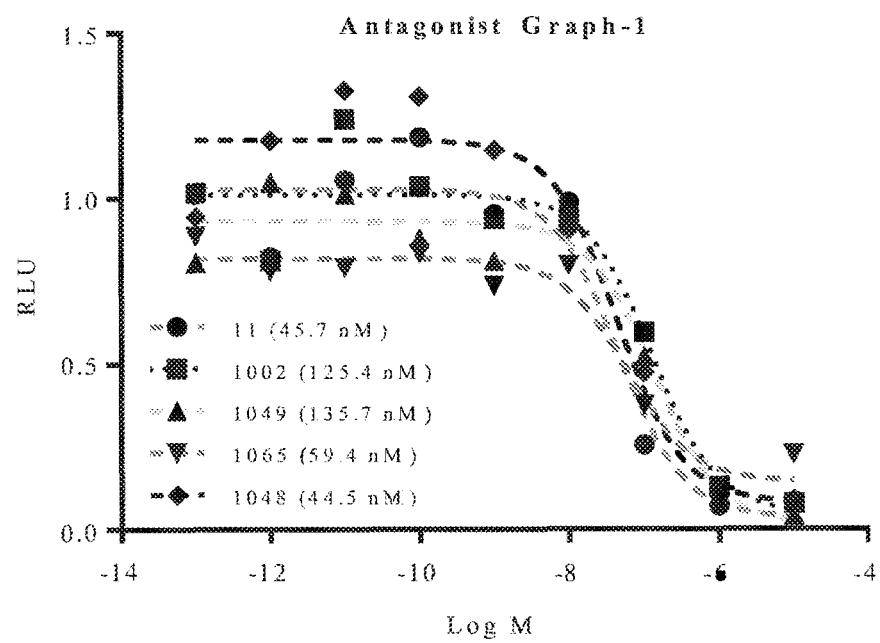
Figure 1C:
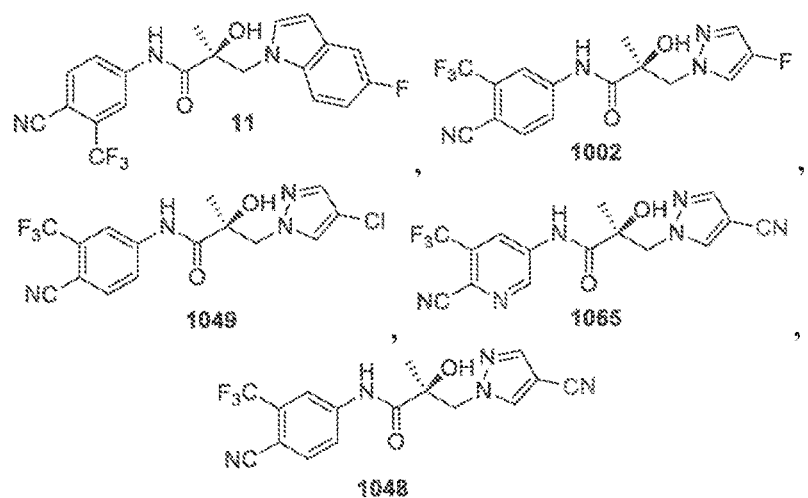

Indole 11 was a more potent AR antagonist in vitro (45 nM) than several representative pyrazoles which exhibited slightly less potent AR antagonism (see FIGS. 1A-1C). However 47 and 99 exhibited extremely (unexpectedly compared to 11) potent AR antagonist in vitro ($IC_{50}$ values of 20.38 and 26.74 nM, see Table 1) but rapid metabolism (data not shown). Enzalutamide and R1881 served as positive controls for antagonist and agonist activity in this assay, and behaved as expected. 11 is 4-5 fold more potent than enzalutamide in vitro but suffers from poor in vivo activity due to poor bioavailability. 1002 is the 4-fluoro pyrazole which is a relatively weak antagonist in vitro but exhibited in vivo antagonism in excess of 11 and was the lead SARD going into this experiment. 1065 and 1048 exhibited approximately 2-fold more potent AR antagonism in vitro than 1002 (FIGS. 1A-1C).

Example 4

In Vivo Antagonism of SARD Compounds

Hershberger Method:

Male rats (n=5/group) were left intact, except for a castrated positive control group as indicated in the figures, for 13 days. Intact rats were treated with the indicated compounds at the indicated dose by mouth daily for 13 days. Rats were sacrificed on day 14 of treatment and prostate and seminal vesicles organs were removed and weighed. Organ weights were either represented as is or were normalized to body weight. In overview, there was a 20 mg/kg fixed dose screening Hershberger which was (performed in 2 batches) for compounds 11 (indole), 1002, 1002(Tart), 1017, 1022, 1045, 1048 (toxic so no data), 1049, 1058, 1065, and 1066 (Example 4); and subsequently a dose response (1, 5, 10, and 20 mg/kg) Hershberger experiment performed with 1048 and 1065 (Example 5). The goal of the experiments was to find compounds with in vivo antiandrogen efficacies greater than 1002.

Figure 2:
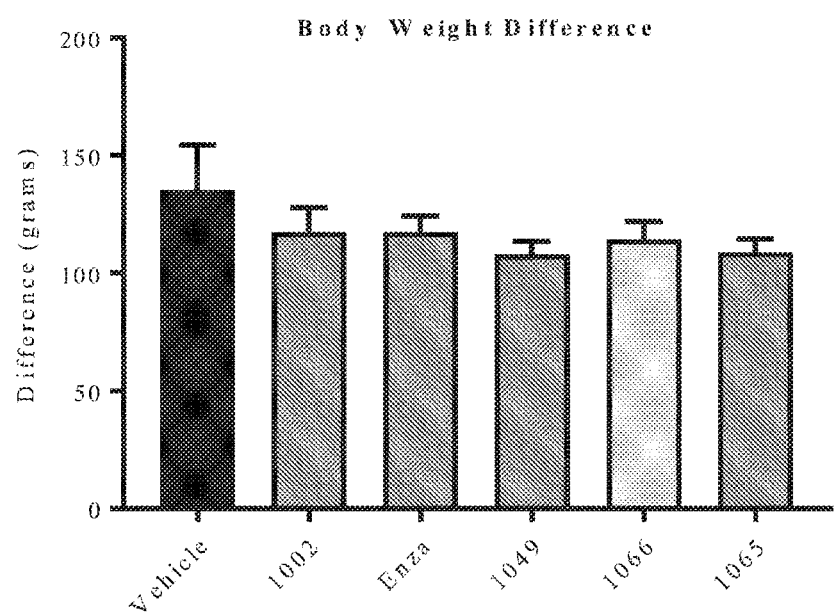
FIG. 2 presents body weight difference following treatment with representative compounds in intact Sprague Dawley rat Hershberger assay at 20 mg/kg for 13 days. The three pyrazoles tested, 1049, 1066 and 1065, produced mild body weight reductions compared to vehicle treated intact rats as shown in "Difference (grams)", whereas 1002 and enzalutamide produced similar body weight reductions which did not meet statistical significance. Slight reduction in body weight is likely to be an AR antagonist effect of reduced androgenic and anabolic tissue mass rather than toxicity, suggesting that there is no gross toxicity for these compounds at this dose. See Table 1 for compound structures.

The screening Hershberger experiment tested compounds in an intact Sprague Dawley rat Hershberger assay at 20 mg/kg for 13 days. The three pyrazoles tested, 1049, 1066 and 1065, produced mild body weight reductions compared to vehicle treated intact rats as shown in Difference (grams), whereas 1002 and enzalutamide produced similar body weight reductions which did not meet statistical significance. The slight reductions in body weight are likely to be an AR antagonist effect of reduced androgenic and anabolic tissue mass rather than toxicity, indicating the lack of general toxicity (FIG. 2).

Figure 3A:
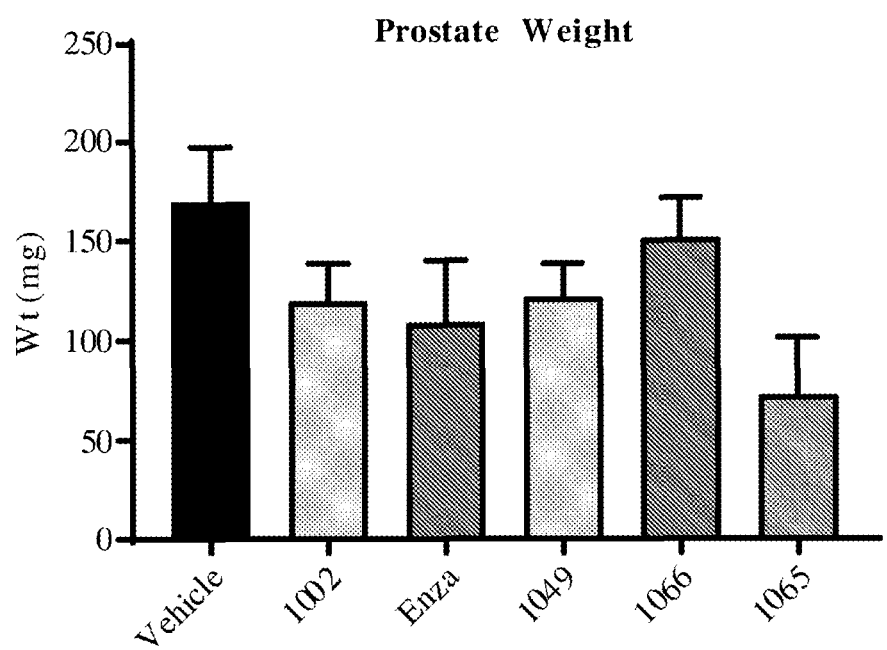
FIGS. 3A-3C present prostate weight reductions following treatment with 20 mg/kg of representative compounds. 1065 emerged as the most efficacious compound at 20 mg/kg in terms androgenic tissue weight reductions. It produced approximately 60% weight reduction in prostate tissue when normalized to body weight. Enzalutamide (30 mg/kg) and 1049 (20 mg/kg) produced prostate organ weight reductions similar to 1002 but 1049 was toxic at this dose, whereas 1066 demonstrated much lower activity despite equipotent in vitro AR antagonism compared to 1049.
Figure 3B:
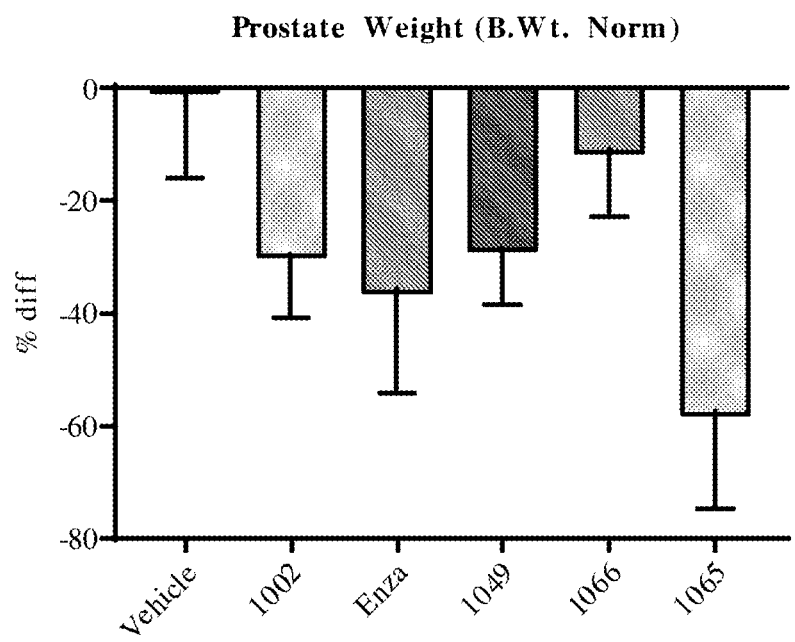
Figure 3C:
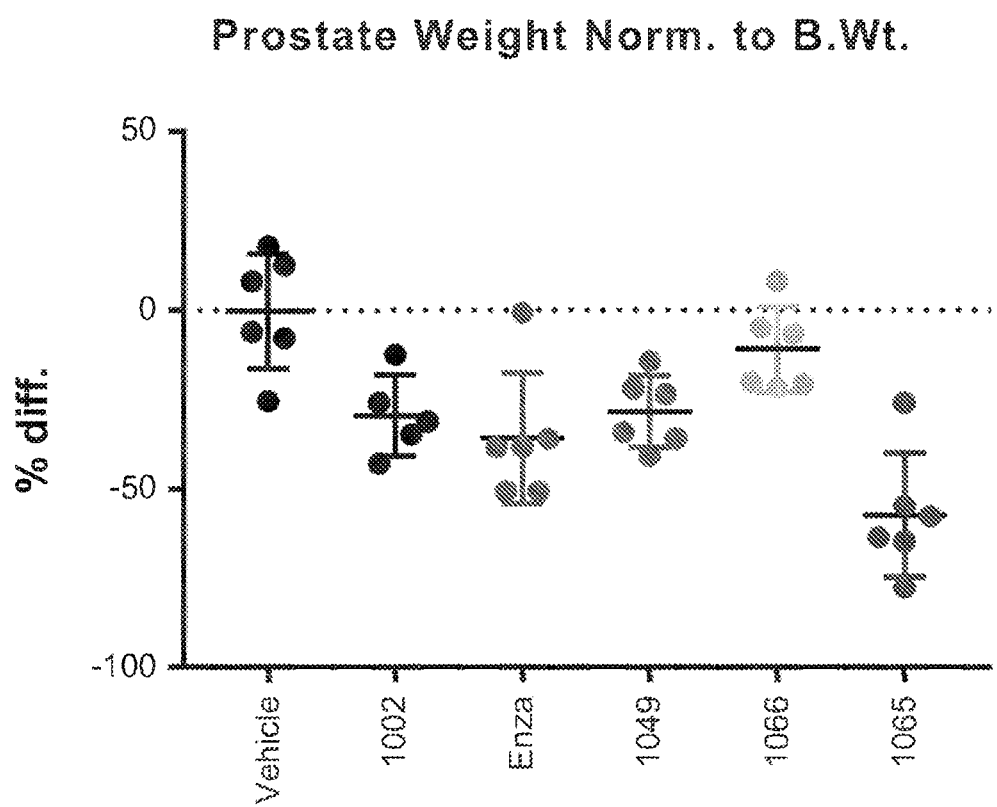

1065 emerged as the most efficacious compound at 20 mg/kg in terms androgenic tissue weight reductions. It produced approximately 60% weight reduction in prostate tissue when normalized to body weight. Enzalutamide (30 mg/kg) and 1049 (20 mg/kg) produced prostate organ weight reductions similar to 1002 but 1049 was toxic at this dose, whereas 1066 demonstrated much lower activity in prostate despite equipotent in vitro AR antagonism compared to 1049 (FIGS. 3A-3C).

Figure 4A:
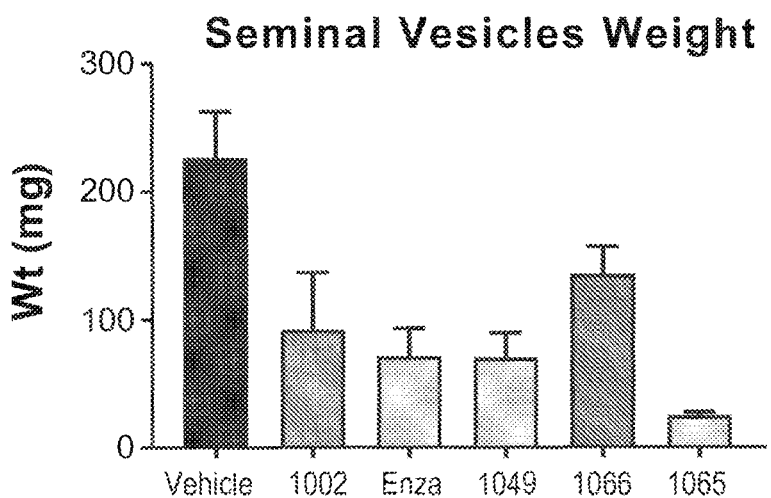
FIGS. 4A-4D present seminal vesicles weight reductions following treatment with 20 mg/kg of representative compounds. Seminal vesicles weight reductions was observed for 1049 and enzalutamide demonstrated similar efficacy to 1002 (60-70% reduced prostate weight normalized to body weight), but less efficacy for 1066 (~40%) but none reached chemical castration (i.e., ~90% reductions for the castration control group). However, the superior efficacy (comparable to castration) of 1065 in seminal vesicles weight was even more apparent than its effects on prostate weights. 1065 demonstrated castration level reductions in seminal vesicles weight for every animal tested (i.e., no variability in the data as seen in FIGS. 4C and 4D), suggesting a saturating dose of AR antagonist that could be reduced. To our knowledge, castration has never been achieved in an intact rat with a nonsteroidal small molecule AR antagonist. Further, these reductions were statistically significantly greater than the other compounds tested in this experiment. Chemical castration with a SARD is unprecedented and represents an unexpected result, i.e., unexpectedly efficacious in vivo AR antagonism.
Figure 4B:
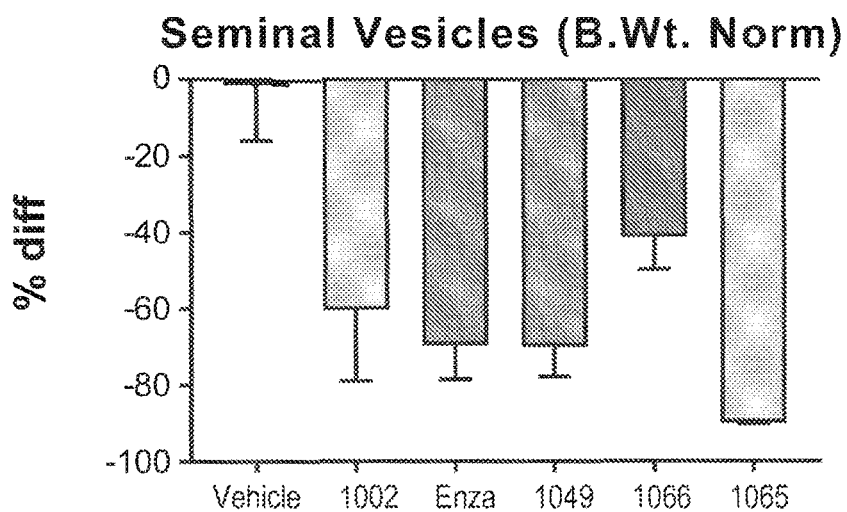
Figure 4C:
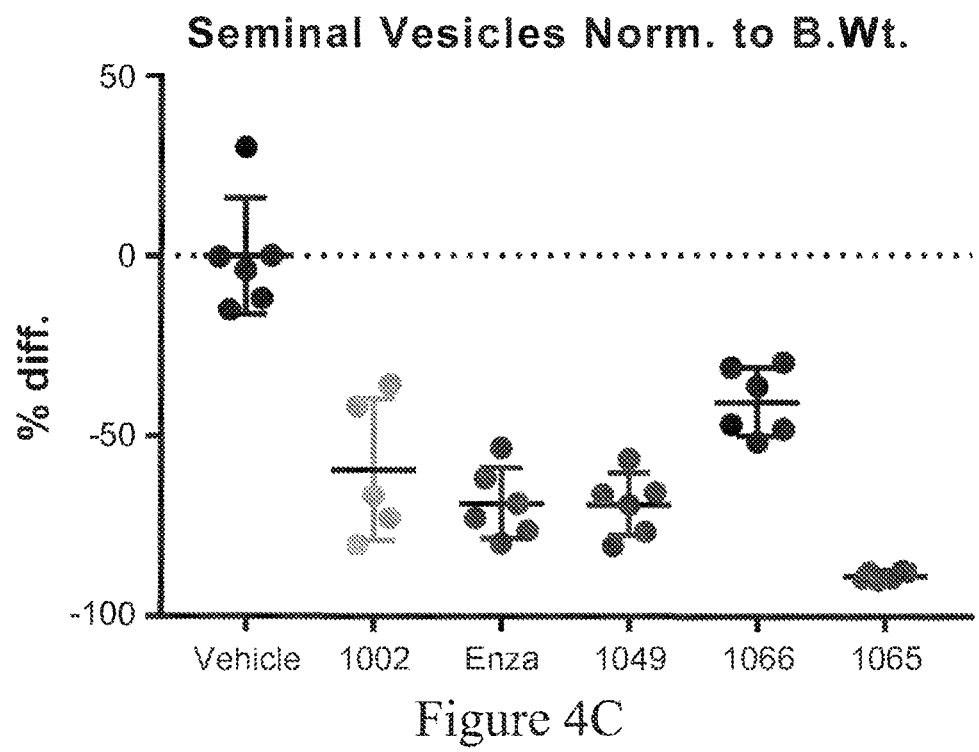
Figure 4D:
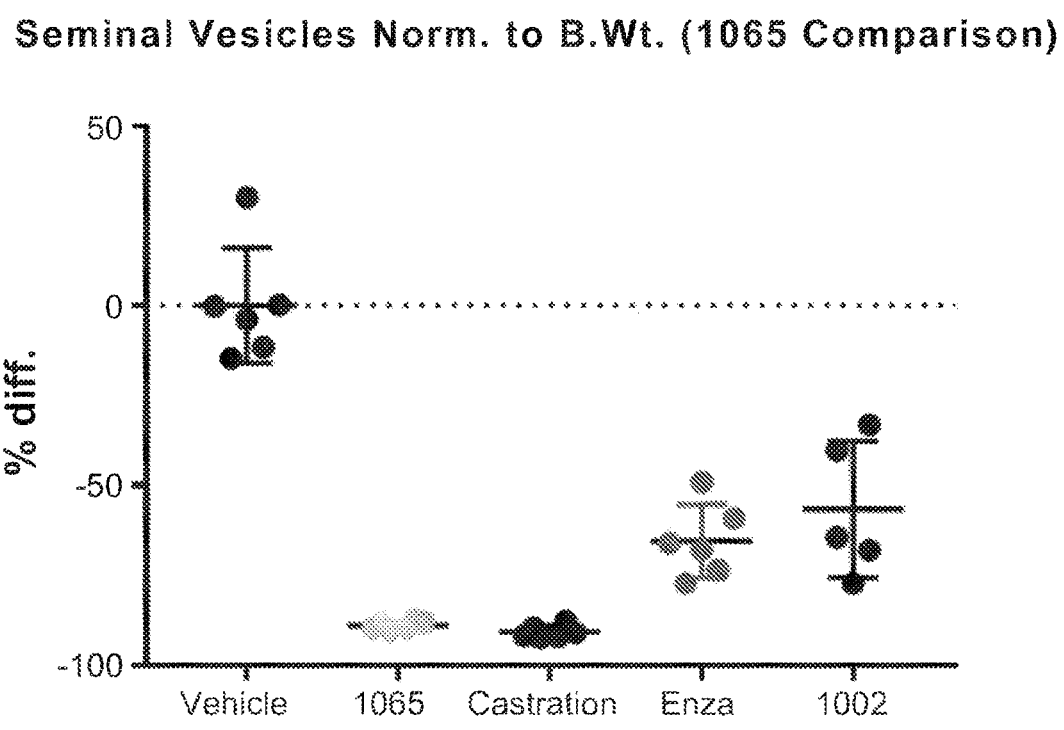
Figure 5A:
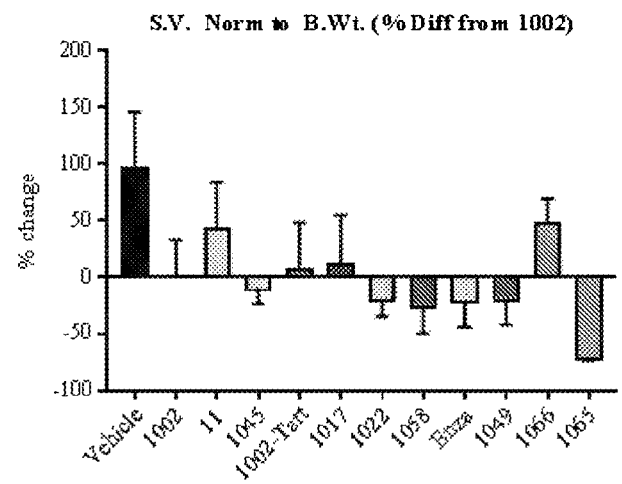
FIGS. 5A-5D present % difference in organ weight from 1002 (% Diff from 1002) with 1002 defined as 0% change and vehicle defined as 100% change. When seminal vesicles (S.V.
Figure 5B:
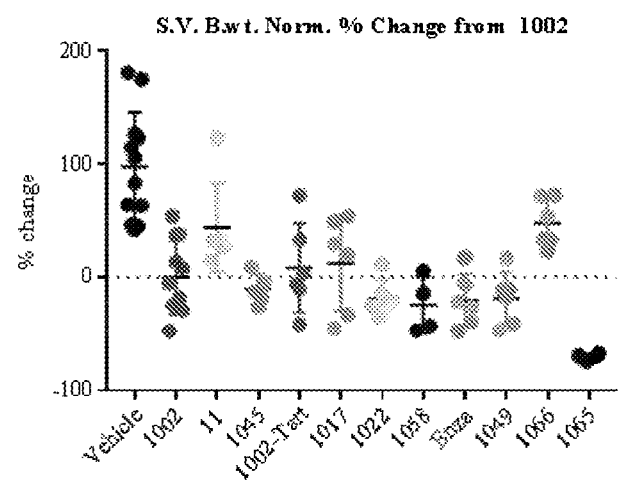
Figure 5C:
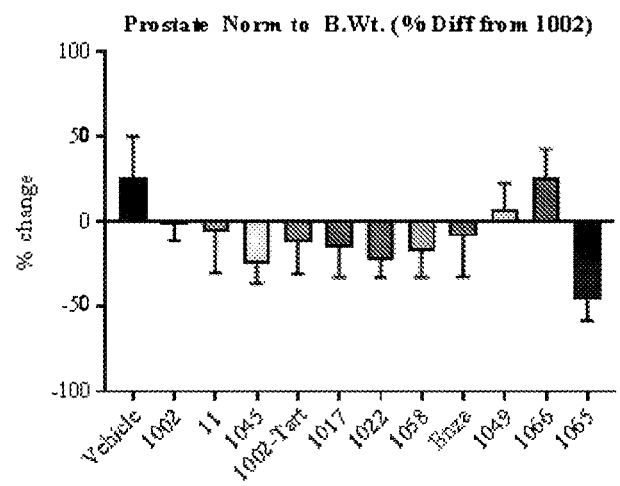
Figure 5D:
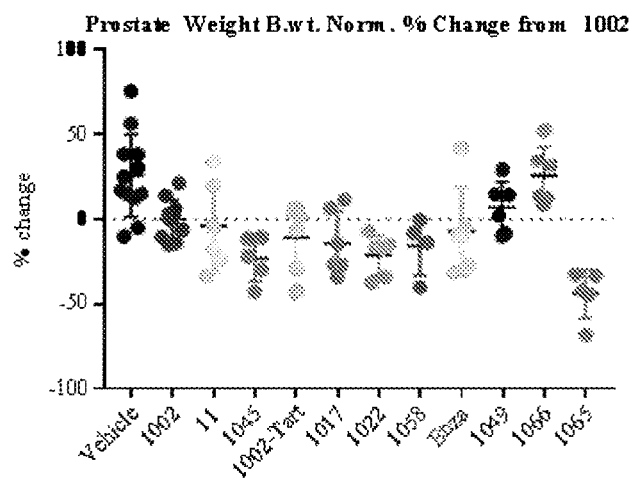

The same pattern was observed in seminal vesicles (SV) weight reductions with 1049 and enzalutamide demonstrating similar efficacy to 1002 (60-70% reduced seminal vesicles weight normalized to body weight (FIG. 4B) and less efficacy for 1066 (~40%) compared to −90% reductions for castration (FIG. 4D). However, the superiority of 1065 was even more apparent in seminal vesicles tissues (FIGS. 4A-4D). 1065 demonstrated castration level reductions in seminal vesicles weight for every animal tested (i.e., no variability in the data), suggesting a saturating antiandrogen dose that could be reduce and still produce chemical castration (FIGS. 4C and 4D). Further, the reduction in SV was statistically significantly greater than all other compounds tested (FIGS. 4A and 4B). Chemical castration with a SARD is unprecedented and represents an unexpected result, i.e., unexpectedly high efficacy in vivo AR antagonism (FIGS. 4A-4D).

The graphs presented in FIGS. 5A-5D show the % difference in organ weight from 1002 (% Diff from 1002) with 1002 defined as 0% change and vehicle defined as 100% change. When seminal vesicles (FIGS. 5A and 5B) and prostate (FIGS. 5C and 5D) weight reductions for all the compounds over the two studies are reported together, several compounds produced comparable to slightly improved efficacies compared to 1002. However, it is clear that 1065 is the most efficacious AR antagonist in vivo in a Hershberger assay, reaching castration levels for seminal vesicles which is significantly more efficacious than all other compounds tested and unprecedented to our knowledge.

Figure 6:
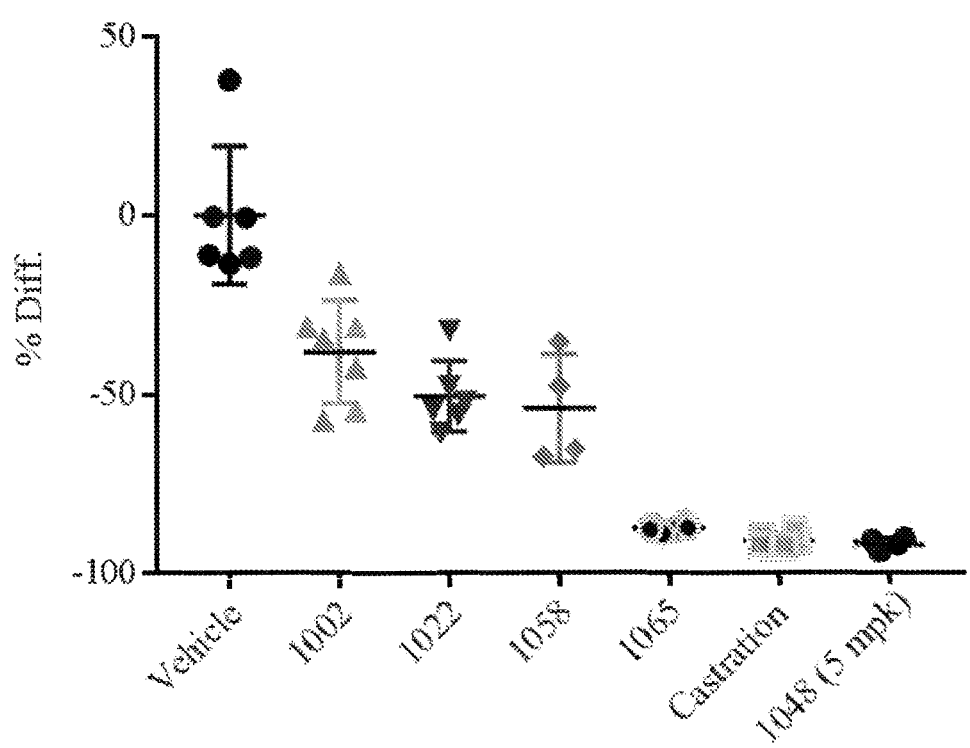
FIG. 6 presents in vivo AR antagonism of 1048, 1065, 1058, and 1022 with regard to seminal vesicles weight reduction and corresponding serum concentrations and in vitro antagonism and degradation. [Though all the animals treated with 1048 died at 20 mg/kg, in a subsequent experiment (described herein below) we attempted to separate toxic dose from therapeutic dose and the 5 mg/kg dose for 1048 is shown in this figure. All other compounds were dosed at 20 mg/kg in this figure. Each of the four compounds produced in vivo antagonism in excess of 1002 which, assuming similar bioavailabilities, agrees well with 3-4 fold increased in vitro antagonism and improved degradation. However, following this logic 1022 (~55% reduction) and 1065 (~90% reduction) should have produced similar in vivo effects but they did not. At sacrifice, blood samples were taken and serum drug levels were determined. These levels revealed that 1065, 1058, and 1022 had approximately 17-, 12- and 2-fold higher serum levels in rats when dosed at 20 mg/kg. Notably, 1065 demonstrated unexpectedly improved oral bioavailability compared to all previous SARD compounds, demonstrating full AR antagonism in vivo. (See Table 1 for structures.)

The four most efficacious compounds 1048, 1065, 1058, and 1022 are examined in FIG. 6 with regard to seminal vesicles (SV) weight reduction (in vivo AR antagonism) and corresponding serum concentrations (Table 2) and in vitro antagonism and degradation (Table 2). The animals treated with 1048 were dosed at 5 mg/kg dose (20 mg/kg was lethal). All other compounds were dosed at 20 mg/kg. Each of the four compounds produced in vivo antagonism in excess of 1002 which, assuming similar bioavailabilities, agrees well with 3-4 fold increased in vitro antagonism. However, following this logic 1022 (~55% reduction in SV weight) and 1065 (~90% reduction in SV weight) should have produced similar in vivo effects but they did not. At sacrifice, blood samples were taken and serum drug levels were determined. These levels revealed that 1065, 1058, and 1022 had approximately 17-, 12- and 2-fold higher serum levels than 1002 in rats when dosed at 20 mg/kg, helping to rationalize their rank order of in vivo AR antagonism. It is unexpected in view of previous data, that introducing a nitrogen into the A-ring would double bioavailability (64 nM for 1022 vs. 33 nM for 1002) and further exchanging 4-F with 4-CN would increase bioavailability by another 9-fold (561 nM for 1065 vs. 64 nM for 1022) (Table 2). Notably, 1065 demonstrated unexpectedly improved oral bioavailability compared to all previous SARD compounds, and this enabled the observation for the first time of full AR antagonism in vivo (i.e., chemical castration) with our SARDs (or any small molecule AR antagonist to our knowledge). This was despite relatively low SARD activity (Table 1). It is also unexpected that the introduction of a nitrogen atom into the A-ring of 1048 to produce 1065 would abrogate the dose-limiting toxicity observed with 1048 and allow a therapeutic index (toxic dose/effective dose) of >20 for 1065, as discussed below (see Table 4B). E.g., 1065 demonstrated no toxicity at 20 mg/kg whereas 1048 was toxic at 5 mg/kg and lethal at 10 and 20 mg/kg. Also, 1058 had unexpected improvement in oral bioavailability however, despite serum levels almost comparable to 1065 and comparable in vitro antagonism, did not produce chemical castration but instead was only marginally better than 1002 in vivo, indicating that high serum levels are not necessarily predictive of in vivo antagonism. (See also 1045 serum concentrations vs. in vivo efficacy reported infra.)

TABLE 2

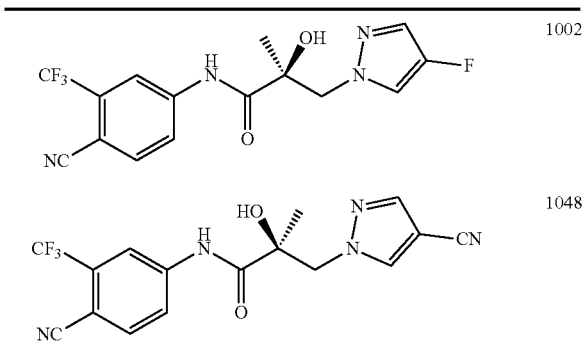

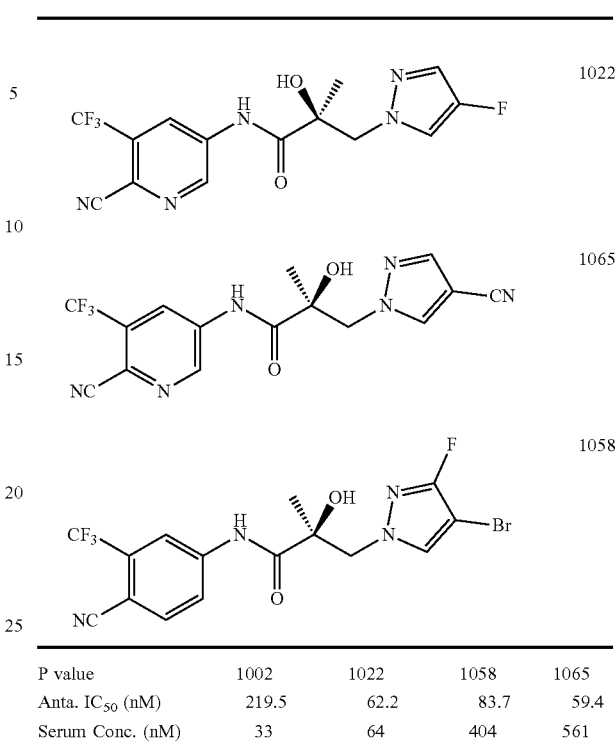

| P value | 1002 | 1022 | 1058 | 1065 |
|---|---|---|---|---|
| Anta. IC$_{50}$ (nM) | 219.5 | 62.2 | 83.7 | 59.4 |
| Serum Conc. (nM) | 33 | 64 | 404 | 561 |

Enza IC$_{50}$ is ~275 nM.

Serum concentrations in samples obtained 24-30 hours after last dose.

Table 3 below reports the in vitro efficacy (transactivation/degradation) and metabolism (RLM/HLM half-lives (i.e., disappearance on co-incubation with rat or human liver microsomes)) data, and in vivo efficacy (S.V. (seminal vesicles) and prostate % diff (i.e, from intact vehicle treated rats)) and serum concentration for all the compounds in the 20 mg/kg Hershberger experiment. Notably, triazole 1045 also demonstrated outstanding pharmacokinetic properties but relative weak AR antagonism. Similarly, 1049 improved bioavailability compared to 1002 by 4-fold but did not greatly increase in vivo antagonism at 20 mg/kg. These examples confirm that high serum concentrations are not necessarily sufficient to confer high potency and efficacy antiandrogenic activity in vivo. (Nor does in vitro degradation necessarily correlate with in vivo potency/efficacy.) Moreover, human liver microsome (HLM) data and RLM data were not necessarily predictive of serum concentrations (see 1017 and 1066), confounding candidate selection for in vivo testing.

TABLE 3

| | 1048 | Castration | 1065 | 1058 | 1022 | 1002 | 1045 | 1049 | 11 | 1017 | 1088 |
|---|---|---|---|---|---|---|---|---|---|---|---|
| Transactivation (nM) | 40.8 | | 59.4 | 83.7 | 62.2 | 219.5 | 383.3 | 132.7 | 28.95 | 71.2 | 138.2 |
| Degradation (% at 3 μM) | 87 | | | 82 | 52 | 53 | 47 | 42 | 60 | 80 | 0 |
| RLM Metebolism (H.L. min) | 86 | | 84 | 400 | 146 | 78 | 400 | 179 | 11 | 400 | 300 |

TABLE 3-continued

| | 1048 | Castration | 1065 | 1058 | 1022 | 1002 | 1045 | 1049 | 11 | 1017 | 1088 |
|---|---|---|---|---|---|---|---|---|---|---|---|
| HLM Metabolism (H.L. min) | 400 | | STABLE (0% metabolized after 60 min) | 138 | 108 | 82 | 204 | 102 | 6 | 400 | 319 |
| (S.V.) % diff | −90 (@ 5 mpk) | −90 | −88 | −54 | −50 | −40 | −45 | −65 | −12 | −31 | −35 |
| (Prostate) % diff | −90 (@ 5 mpk) | −88 | −58 | −30 | −34 | −24 | −35 | −20 | −19 | −28 | −9 |
| Serum Conc. (nM) | | | 561 | 404 | 64 | 33 | 1209 | 125 | 0 | 0 | 19 |
| Notes | | | Combination of excellent in vitro properties, in vivo efficacy, and PK properties make these molecules unique (especially DJ-VII-105) | | | | Outstanding PK property. | | Metabolism issue | | |

Table 4 below summarizes that 1065 produced unprecedented chemical castration in intact rats at 20 mg/kg without toxicity, whereas 1048 was toxic at this dose (and lower doses). Also illustrated is that AR LBD binding (Ki) and in vitro antagonism are not necessarily predictive of in vivo AR antagonism, which is partially due to unexpected disparities in oral bioavailability.

TABLE 4

| Cmpd. No. | Binding (Ki) | $IC_{50}$ (nM) | Seminal Vesicles (% inhibition) 20 mpk | Prostate (% inhibition) 20 mpk | Serum Conc. After 30 hrs 20 mpk (nM) | Degradation (% at 3 μM) |
|---|---|---|---|---|---|---|
| 1065 | N.B. | 59.4 | 88 | 52 | 561 | 15 |
| 1048 | 1499 | 44.5 | *** | *** | *** | 74 |
| 1022 | N.B. | 62.2 | 51 | 34 | 64 | 82 |
| 1002 | N.B. | 219 | 40 | 20 | 33 | 53 |
| Castration | — | — | 90 | 54 | — | — |

N.B. = No Binding
*** = Toxic at 20 mpk. All animals died between day 7 and 10

Example 5

Dose Response Hershberger: Unexpected In Vivo Potency, Efficacy, and Safety with 1065

Figure 7:
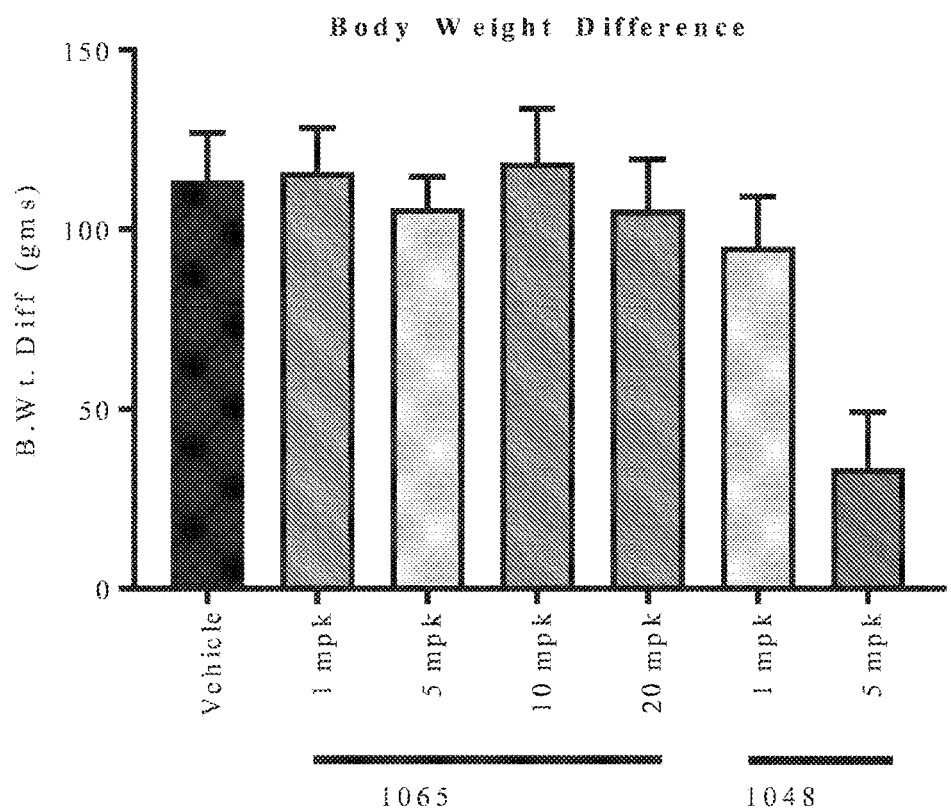
FIG. 7 presents body weights for 1048 and 1065 in a dose response (1, 5, 10, and 20 mg/kg) Hershberger experiment. In the course of the dose response Hershberger experiment, it was observed that 1065 did not demonstrate any toxicity in rats up to 20 mg/kg, as evidenced by the lack of body weight loss (i.e., B. Wt. Diff). In contrast, 1048 was toxic at 5 mg/kg and had to be sacrificed on day 9 (instead of day 14). There was no significant difference in body weight for all doses of 1065 but 1048 demonstrated a dramatic body weight loss of 70% at 5 mg/kg.
Figure 8A:
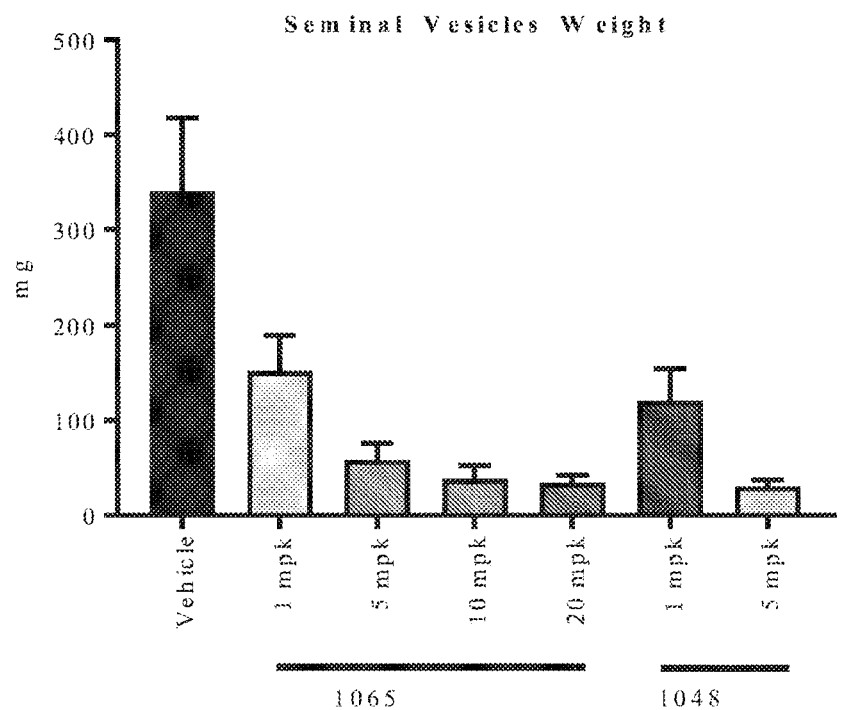
FIGS. 8A-8B present dose response of seminal vesicles weight for 1048 and 1065. 1065 produced complete regression (indistinguishable from castration) of seminal vesicles weight in intact rats by 5 to 10 mg/kg with 83% and 89% weight reduction (% inhibition compared to intact vehicle) and similar reduction at 20 mg/kg. 1065 demonstrated an $IC_{50}$ value of less than 1 mg/kg (i.e., 55% reduction at this dose). 1048 appears to be comparably efficacious at 1 mg/kg, i.e., has similar potency in vivo, however is toxic at 5 mg/kg and lethal at 10 and 20 mg/kg, suggesting that the therapeutic index for 1048 may be unacceptably narrow. By comparison, 1065 demonstrated a therapeutic index for chemical castration in this experiment of at >2-fold or >4-fold based on prostate or seminal vesicles data, respectively and much higher based on a subsequent Hershberger experiment with 100 and 200 mg/kg doses without gross pathology (Table 4B). We still do not know the maximum tolerated dose. All reductions were statistically significant compared to intact vehicle treated animals. It is unexpected that adding a N-atom into the A-ring of 1065 would improve the therapeutic index over 1048 by at least four-fold.
Figure 8B:
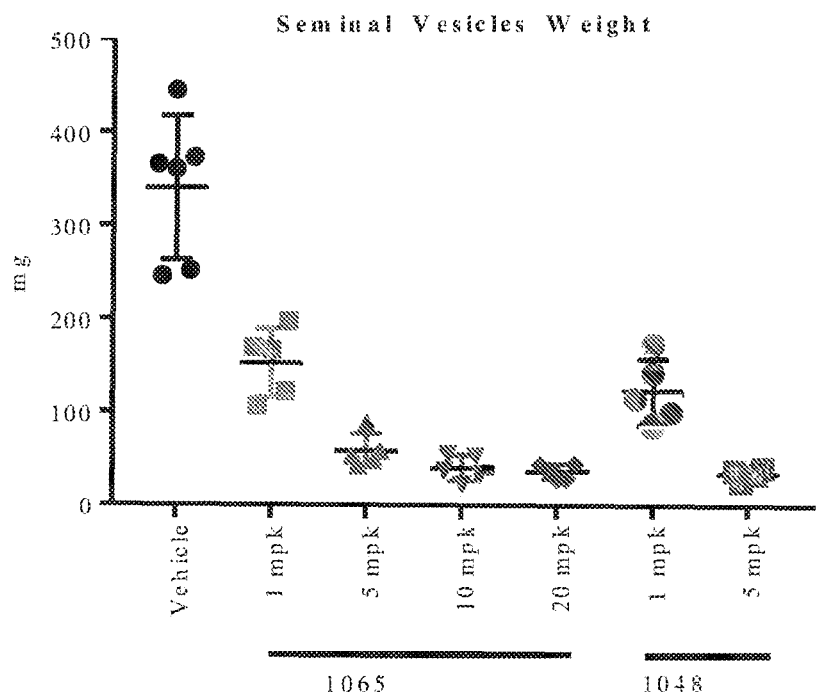

Given that higher in vivo potency and efficacy in a Hershberger assay was seen with 1065 and 1048 than any previous SARD of this template or any other template, a dose response Hershberger experiment was performed. In the course of the dose response, it was observed that 1065 did not demonstrate any toxicity in rats up to 20 mg/kg, as evidenced by the lack of body weight loss (i.e., B. Wt. Diff). In contrast, 1048 was toxic at 5 mg/kg requiring early sacrificed on day 9 and was lethal at higher doses. There was no significant difference in body weight for all doses of 1065, but 1048 demonstrated significant body weight loss of −70% at 5 mg/kg (FIG. 7).

In contrast, 1065 was non-toxic at all doses up to 20 mg/kg and produced complete regression (indistinguishable from castration) of seminal vesicles weight in intact rats by 5 to 10 mg/kg with 83% and 89% weight reduction (% inhibition compared to intact vehicle) and similar reduction at 20 mg/kg. 1065 demonstrated an $IC_{50}$ value of less than 1 mg/kg (i.e., 55% reduction at this dose). 1048 appeared to be comparably potent at 1 mg/kg however was toxic at 5 mg/kg, suggesting that the therapeutic index for 1048 may be unacceptably narrow. All reductions were statistically significant compared to intact vehicle treated animals. It is unexpected that adding a N-atom into the A-ring of 1048 to produce 1065 would improve the therapeutic index many fold (Table 4B, discussed below).

Figure 9A:
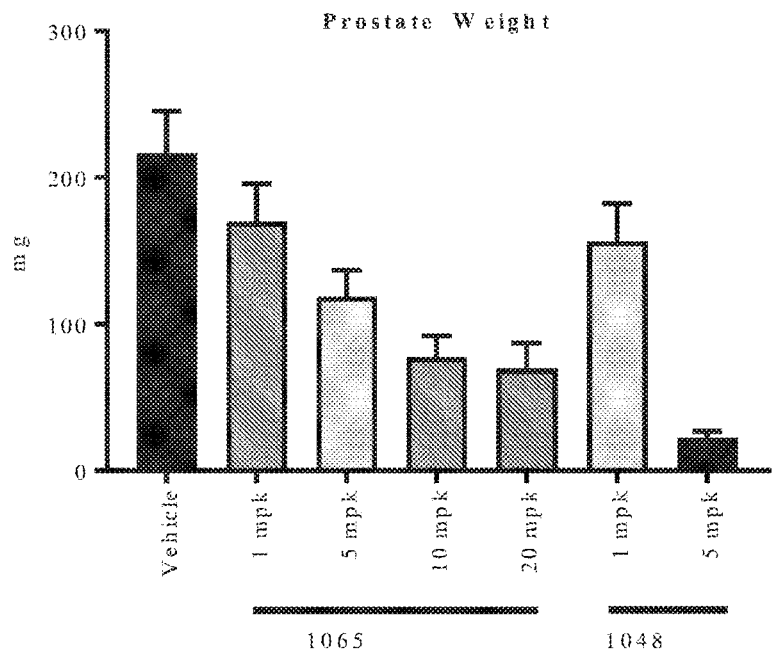
FIGS. 9A-9B present dose response of prostate weight for 1048 and 1065. 1065 also reduced the prostate weight in intact rats to castration by 10 mg/kg, with statistically significant reductions at doses as low as 1 mg/kg and an $IC_{50}$ value near 5 mg/kg. As is typical in Hershberger assays, the prostate weights are not as sensitive to AR antagonism and take longer to reach Emax effects. The inadequate therapeutic index of 1048 is more apparent here with castration levels reductions coming at toxic doses. All reductions in prostate weight were statistically significant differences from intact vehicle treated animals.
Figure 9B:
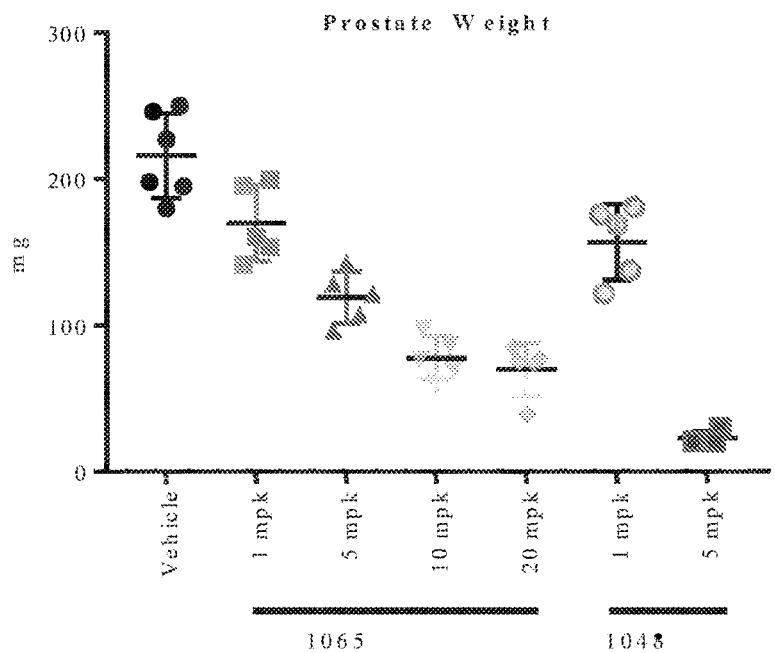

Similarly, 1065 also reduced the prostate weight in intact rats to castration by 10 mg/kg, with statistically significant reductions at doses as low as 1 mg/kg and an $IC_{50}$ value near 5 mg/kg. As is typical in Hershberger assays, the prostate weights are not as sensitive to AR antagonism and take longer to reach $E_{max}$ effects compared to seminal vesicles. The inadequate therapeutic index of 1048 is more apparent here with castration level reductions coming at toxic doses. All reductions in prostate weight were statistically significantly different from intact vehicle treated animals (FIG. 9A-9B).

High Dose Hershberger Experiment to Explore Limits of the Therapeutic Index of 1065
Method:

Intact Sprague Dawley rats (300 grams) were treated with 100 mg/kg of 1058, 100 mg/kg of 1065, or 200 mg/kg of 1065 orally for 7 days. Body weights were recorded on day 0 and day 7 (Table 4B). On day 7, animals were sacrificed and organs were observed.
Result:

No mortality occurred during the seven days of treatment. All the animals gained body weight and exhibited no signs of toxicity. Gross pathological observation at the end of the treatment demonstrated the expected AR antagonism (atrophy) of seminal vesicles and prostate organs but did not show any abnormality in any of the treated animals.
Conclusion.

1065 produced no gross pathology at 100 and 200 mpk. Given xenograft and Hershberger efficacies at 10 mpk (discussed above), 1065 has at least 20 fold margin of safety (i.e., therapeutic index), whereas 1048 is toxic at doses similar to Hershberger efficacy. Doses higher than 200 mg/kg were not tested, so the maximum tolerated dose is not yet known.

TABLE 4B

| Drug | Dose | Animal # | Day 0 body wt. (g) | Body wt. on sac. day (g) |
|---|---|---|---|---|
| 1058 | 100 mpk | 1 | 430 | 430 |
| | | 2 | 472 | 470 |
| 1065 | 100 mpk | 1 | 404 | 475 |
| | | 2 | 280 | 333 |
| | | 3 | 245 | 292 |
| 1065 | 200 mpk | 1 | 270 | 326 |
| | | 2 | 270 | 313 |
| | | 3 | 440 | 424 |

Methodology and Raw for Serum Concentration Determinations for 1065 and 1048.

Serum Concentration Determination for 1065 (Averages Presented in Tables 2-4 and Raw Data in Table 5).

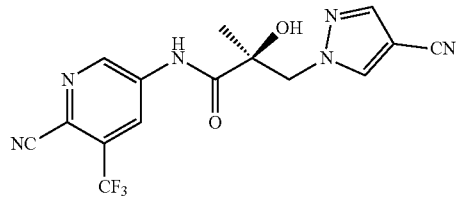 [SMILES: C[C@](O)(Cn1cc(C#N)cn1)C(=O)Nc1cnc(C#N)c(C(F)(F)F)c1]

Serum was collected 24-30 hours after last dose. 100 μL of serum was mixed with 200 0_, of acetonitrile/internal standard. Standard curves were prepared by serial dilution of standards in nM with 100 μL of rat serum, concentrations were 1000, 500, 250, 125, 62.5, 31.2, 15.6, 7.8, 3.9, 1.9, 0.97, and 0. Standards were with extracted with 200 μL of acetonitrile/internal standard. The internal standard for this experiment was (S)-3-(4-cyanophenoxy)-N-(3-(chloro)-4-cyanophenyl)-2-hydroxy-2-methylpropanamide.

LC-MS/MS Analysis:

The analysis of the 1065 was performed using LC-MS/MS system consisting of Shimadzu Nexera X2 HPLC with an AB/Sciex Triple Quad 4500 Q-Trap™ mass spectrometer. The separation was achieved using a C18 analytical column (Alltima™, 2.1×100 mm, 3 μm) protected by a C18 guard column (Phenomenex™ 4.6 mm ID cartridge with holder). Mobile phase was consisting of channel A (95% acetonitrile+5% water+0.1% formic acid) and channel C (95% water+5% acetonitrile+0.1% formic acid) and was delivered isocratically at a flow rate of 0.4 mL/min at 70% A and 30% B. The total runtime for 1065 was 2.50 min, and the volume injected was 10 μL. Multiple reaction monitoring (MRM) scans were made with curtain gas at 10; collision gas at medium; nebulizer gas at 60.0 and auxiliary gas at 60.0 and source temperature at 550° C. Molecular ions were formed using an ion spray voltage of 4200 (negative mode). Declustering potential, entrance potential, collision energy, product ion mass, and cell exit potential were optimized with the values of −75, −10, −30, and −13, respectively, for the mass pair 363.1/185.6.

Raw data of 1065 concentrations for individual rats is shown in Table 5.

TABLE 5

| Dose | Samples | Extraction of 1065 Conc. 1065 (nM) |
|---|---|---|
| 1 mg/kg | Serum 1 | 81.57583 |
| | Serum 2 | 87.24625 |
| | Serum 3 | 120.1244 |
| | Serum 4 | 134.5505 |
| | Serum 5 | 129.9323 |
| 5 mg/kg | Serum 1 | 967.3936 |
| | Serum 2 | 798.7984 |
| | Serum 3 | 630.4879 |
| | Serum 4 | 691.1901 |
| | Serum 5 | 485.4264 |
| 10 mg/kg | Serum 1 | 637.641 |
| | Serum 2 | 915.1312 |
| | Serum 3 | 824.8076 |
| | Serum 4 | 681.9936 |
| | Serum 5 | 795.917 |
| 20 mg/kg | Serum 1 | 1286.902 |
| | Serum 2 | 1298.179 |
| | Serum 3 | 1360.687 |
| | Serum 4 | 1397.834 |
| | Serum 5 | 1193.986 |

Serum Concentration Determination for 1048 (Averages in Table 2-4 and Raw Data in Table 6)

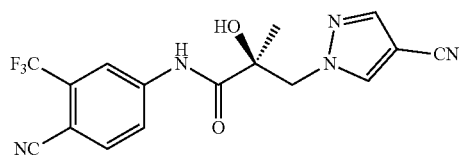 [SMILES: C[C@](O)(Cn1cc(C#N)cn1)C(=O)Nc1ccc(C#N)c(C(F)(F)F)c1]

Serum was collected 24-30 hours after last dose. 100 μL of serum was mixed with 200 μL of acetonitrile/internal standard. Standard curves were prepared by serial dilution of standards in nM with 100 μL of rat serum, concentrations were 1000, 500, 250, 125, 62.5, 31.2, 15.6, 7.8, 3.9, 1.9, 0.97, and 0. Standards were with extracted with 200 μL of acetonitrile/internal standard. The internal standard for this experiment was (S)-3-(4-cyanophenoxy)-N-(3-(chloro)-4-cyanophenyl)-2-hydroxy-2-methylpropanamide.

LC-MS/MS Analysis:

The analysis of the 1048 was performed using LC-MS/MS system consisting of Shimadzu Nexera X2 HPLC with an AB/Sciex Triple Quad 4500 Q-Trap™ mass spectrometer. The separation was achieved using a C18 analytical column (Alltima™, 2.1×100 mm, 3 μm) protected by a $C_{18}$ guard column (Phenomenex™ 4.6 mm ID cartridge with holder). Mobile phase was consisting of channel A (95% acetonitrile+5% water+0.1% formic acid) and channel C (95% water+5% acetonitrile+0.1% formic acid) and was delivered isocratically at a flow rate of 0.4 mL/min at 70% A and 30% B. The total runtime for 1048 was 2.50 min, and the volume injected was 10 μL. Multiple reaction monitoring (MRM) scans were made with curtain gas at 10; collision gas at medium; nebulizer gas at 60.0 and auxiliary gas at 60.0 and source temperature at 550° C. Molecular ions were formed using an ion spray voltage of 4200 (negative mode). Declustering potential, entrance potential, collision energy, product ion mass, and cell exit potential were optimized with the values of −100, −10, −34, and −9, respectively, for the mass pair 362.29/184.6.

Raw data for 1048 serum concentrations in individual rats is shown in Table 6. As can be seen from this raw data, 1048 reaches serum concentrations at 1 and 5 mg/kg that are ~5-fold higher than for 1065 at this dose (for this experiment), and the 5 mg/kg 1048 dose was toxic, necessitating early sacrifice of the rats at day 9. Notably, the μM serum concentrations (approximate 3 μM) for 1048 at 5 mg/kg are 100-fold higher than the in vitro AR antagonistic potency.

TABLE 6

| Dose | Sample | Extraction of 1048 Conc. of 1048 (nM) |
|---|---|---|
| 1 mg/kg | Serum 1 | 621.9929 |
|  | Serum 2 | 760.1658 |
|  | Serum 3 | 676.488 |
|  | Serum 4 | 419.7344 |
|  | Serum 5 | 370.0696 |
| 5 mg/kg | Serum 1 | 4191.451 |
|  | Serum 2 | 1636.436 |
|  | Serum 3 | 2047.831 |
|  | Serum 4 | 3162.571 |

Example 6

Chemical Castration without Lowering Serum Testosterone

Figure 10:
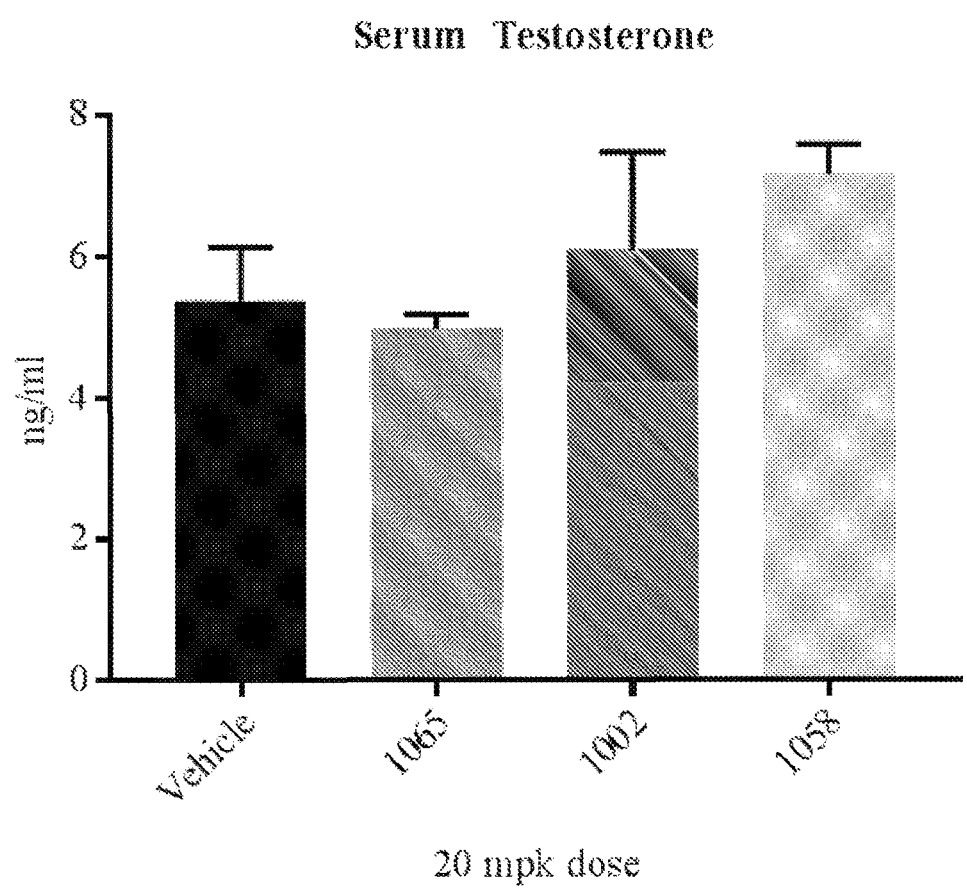
FIG. 10 presents serum testosterone levels of representative compounds. For animals treated with the 20 mg/kg, blood was drawn at the time of sacrifice and serum isolated. The serum was run through a LC-MS/MS to detect testosterone levels. As can be seen, even at levels much higher than those that produced chemical castration for 1065, there is no significant reduction in serum testosterone levels. Similar results were obtained for 1002 and 1058. This indicated that SARDs do not have any effect of the synthesis of testosterone but are potent in vivo AR antagonists by virtue of direct effects on AR (i.e., outside of AR in the CNS that may stimulate the HPG axis and endogenous androgen synthesis). Further, this highlights that SARDs are potent antagonists which are capable of overcoming the endogenous androgens present in intact animals. mpk—mg/kg. See Table 1 for compound structures.

For animals treated with the 20 mg/kg, blood was drawn at the time of sacrifice and serum isolated. The serum was run through a LC-MS/MS to detect testosterone levels. As can be seen in FIG. 10, even at levels much higher than castration for 1065, there is no significant reduction in serum testosterone levels. Similar results were obtained for 1002 and 1058. This indicates that SARDs do not have any effect of the synthesis of testosterone but are potent in vivo AR antagonists by virtue of direct effects on AR. Further, this highlights that SARDs are potent antagonists which are capable of overcoming the endogenous androgens present in intact animals.

Example 7

SARD as Hypothetical AR and GR Co-Antagonists

Figure 11A:
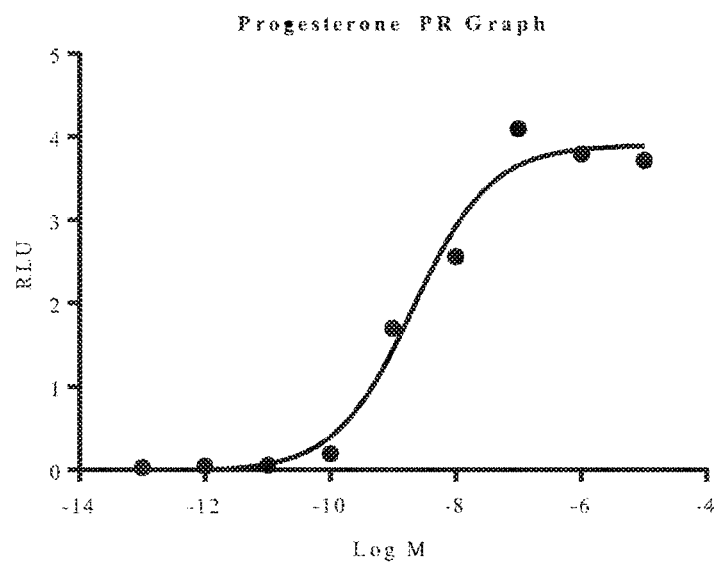
FIGS. 11A-11B present PR antagonism in vitro of representative compounds. The PR antagonism in vitro is often approximately equipotent with AR antagonism in vitro. A notable exception is 1048 which is a relatively weak PR antagonist at 507 nM compared to the other agents, and exhibits 10-fold selectivity for AR antagonism (44.5 nM).
Figure 11B:
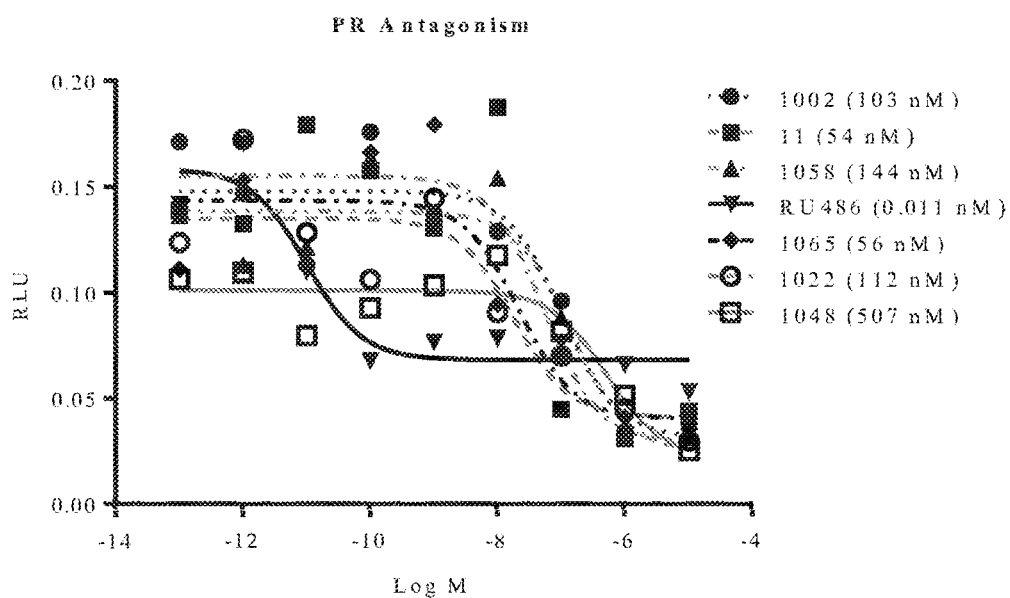

SARDs of this invention were potent AR antagonists in vitro and capable of high efficacy SV and FL AR degradation (Table 1). The tested SARDs demonstrated PR antagonism in vitro which was often approximately equipotent with AR antagonism in vitro. A notable exception was 1048 which was a relatively weak PR antagonist at 507 nM compared to the other agents, and exhibited 10-fold selectivity for AR antagonism (see Table; 44.5 nM) (FIGS. 11A-11B).

Further, SARDs of this invention are tested in a GR transcription activation assay in antagonist mode and produce potent and complete (comparable efficacy to RU486) GR antagonism in vitro. As a positive control, dexamethasone demonstrates potent and full efficacy agonism in the same assay system. If this were true, SARDs of this invention would be able to overcome or prevent the emergence of antiandrogen resistance mediated by GR, as discussed in Horm Cancer. (2014) 5(2), 72-89 or doi:10.1007/s12672-014-0173-2 and Cell (2013) 155, 1309-1322 or doi: 10.1016/j.cell.2013.11.012.

Example 8

Pharmacokinetic Properties of SARD Compounds

Animal Husbandry and Experimental Design

Male Sprague Dawley rats from Envigo RMS, Inc. were acclimated to study conditions for 5 days prior to initial dose administration. At initial dosing, the animals were 12 weeks of age. The animals were group housed (up to three animals/cage/group) in polycarbonate cages with hardwood chip bedding. Certified Rodent Diet #2016C (Envigo RMS, Inc.) was provided ad libitum. Water was provided fresh daily, ad libitum. Environmental controls for the animal room were set to maintain a temperature of 20 to 26° C., a relative humidity of 50±20%, and a 12-hour light/12-hour dark cycle. As necessary, the 12-hour dark cycle was interrupted to accommodate study procedures. The test article was prepared in 15% dimethyl sulfoxide (DMSO)/85% polyethylene glycol (PEG) 300 by Covance. Individual doses were calculated based on body weights recorded on Day 1 and Day 7 of dose administration. A single oral daily dose was administered via a gavage needle on seven consecutive days, and blood was sampled as described below. A single intravenous dose was administered via a tail vein and blood sample on Day 1.

Additional detailed information for the 1065 experiment, including the groups, number of animals per group, dose (oral 1, 5, 10, 20 mg/kg per day; iv 5 mg/kg on Day 1), and route are given in the Experimental Design Table 7 below. 1002 and 1058 were tested with the same experimental protocol except doses were higher. For 1002, target dose levels were oral 5, 20, 30 & 60 mg/kg per day; and iv 5 mg/kg on Day 1. For 1058, target dose levels were oral 5, 10, 20, & 30 mg/kg per day; and iv 10 mg/kg on Day 1. Animals were observed for mortality and signs of pain and distress twice daily (a.m. and p.m.), and cage side observations for general health and appearance were done once daily. Animals were weighed at the time of animal selection and on Day 1 and Day 7 of dose administration.

TABLE 7

EXPERIMENTAL DESIGN
Study Design
Group Designations and Dose Levels

| Group | Number of Male Animals | Test Article | Dose Route | Target Dose Level (mg/kg/day) | Target Dose Concentration (mg/mL) | Target Dose Volume (mL/kg) |
|---|---|---|---|---|---|---|
| 1 | 6 Males | 1065 | Oral[a] | 1 | 0.33 | 3 |
| 2 | 6 Males | 1065 | Oral[a] | 5 | 1.67 | 3 |
| 3 | 6 Males | 1065 | Oral[a] | 10 | 3.33 | 3 |
| 4 | 6 Males | 1065 | Oral[a] | 20 | 6.67 | 3 |
| 5 | 3 Males | 1065 | IV[b] | 5 | 5 | 1 |

IV Intravenous; given as a bolus injection.
[a]Animals received a single daily dose for seven consecutive days.
[b]Animals received a single bolus intravenous injection on Day 1 only.

Sample Collection

Blood (approximately 0.5 mL) was collected via a jugular vein via syringe and needle and transferred into tubes containing K₃EDTA on Days 1 and 7 from three animals/ group predose (Day 7 only) and at approximately 0.083, 0.25, 0.5, 1, 3, 6, 12, and 24 hours postdose. For i.v. group, blood (approximately 0.5 mL) was collected via a jugular vein at approximately 0.083, 0.25, 0.5, 1, 3, 6, 12, and 24 hours postdose. Blood was maintained in chilled cryoracks prior to centrifugation to obtain plasma. Centrifugation began within 1 hour of collection. Plasma was placed into 96-well tubes with barcode labels. Plasma was maintained on dry ice prior to storage at approximately −70° C. Drug concentrations were measured by established chromatography/mass spectrometry (LC-MS/MS) methods.

Results

Figure 12A:
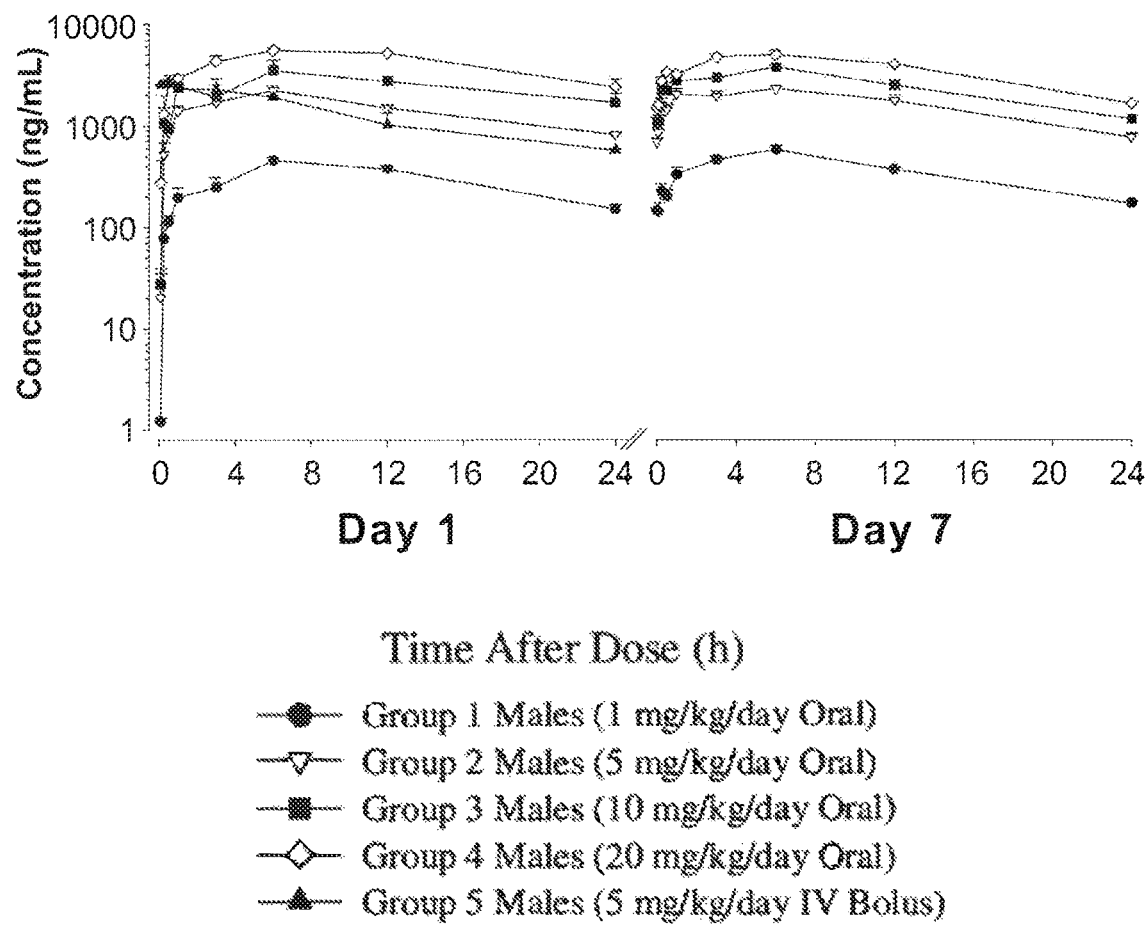
FIGS. 12A, 12B, and 12C present concentration-time profiles of 1065, 1002, and 1058, respectively.
Figure 12B:
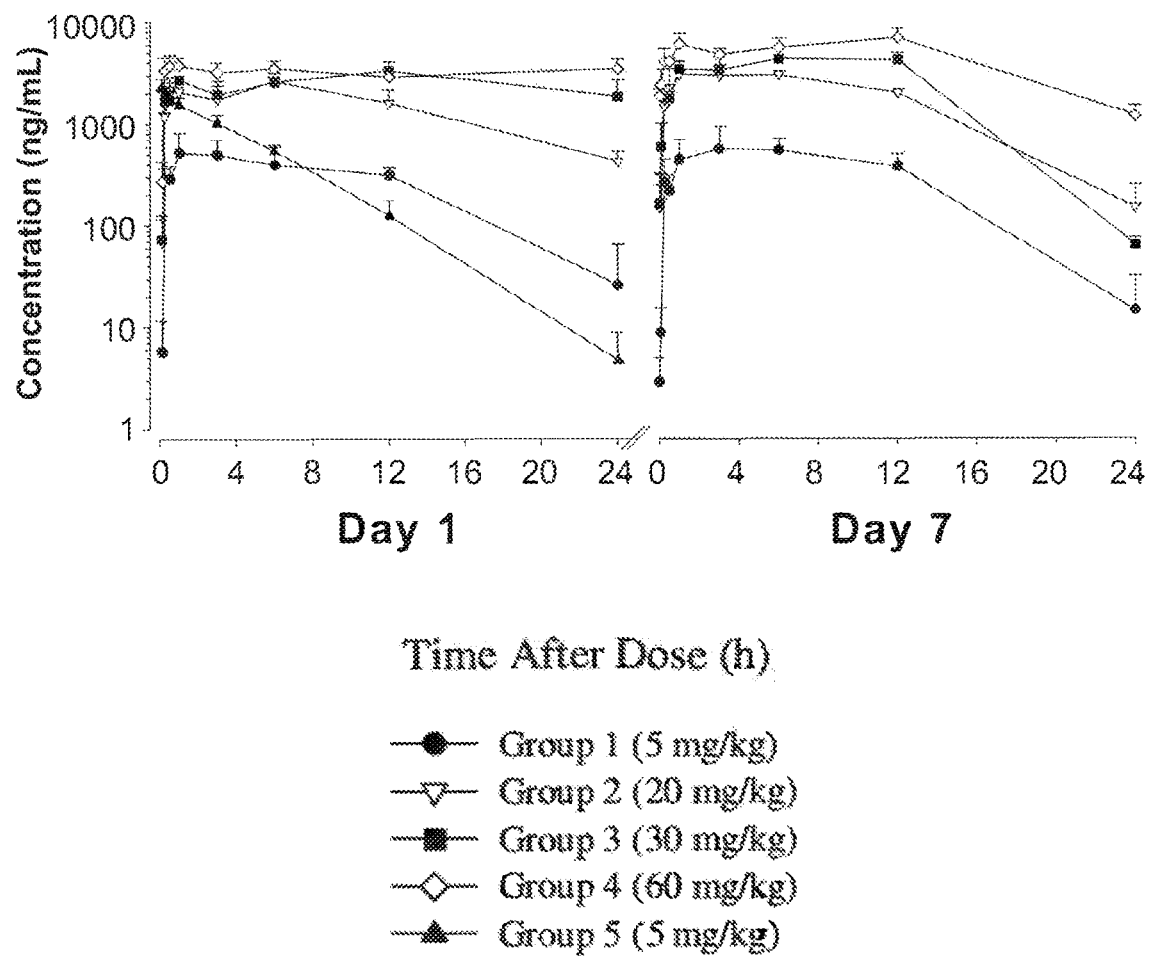
Figure 12C:
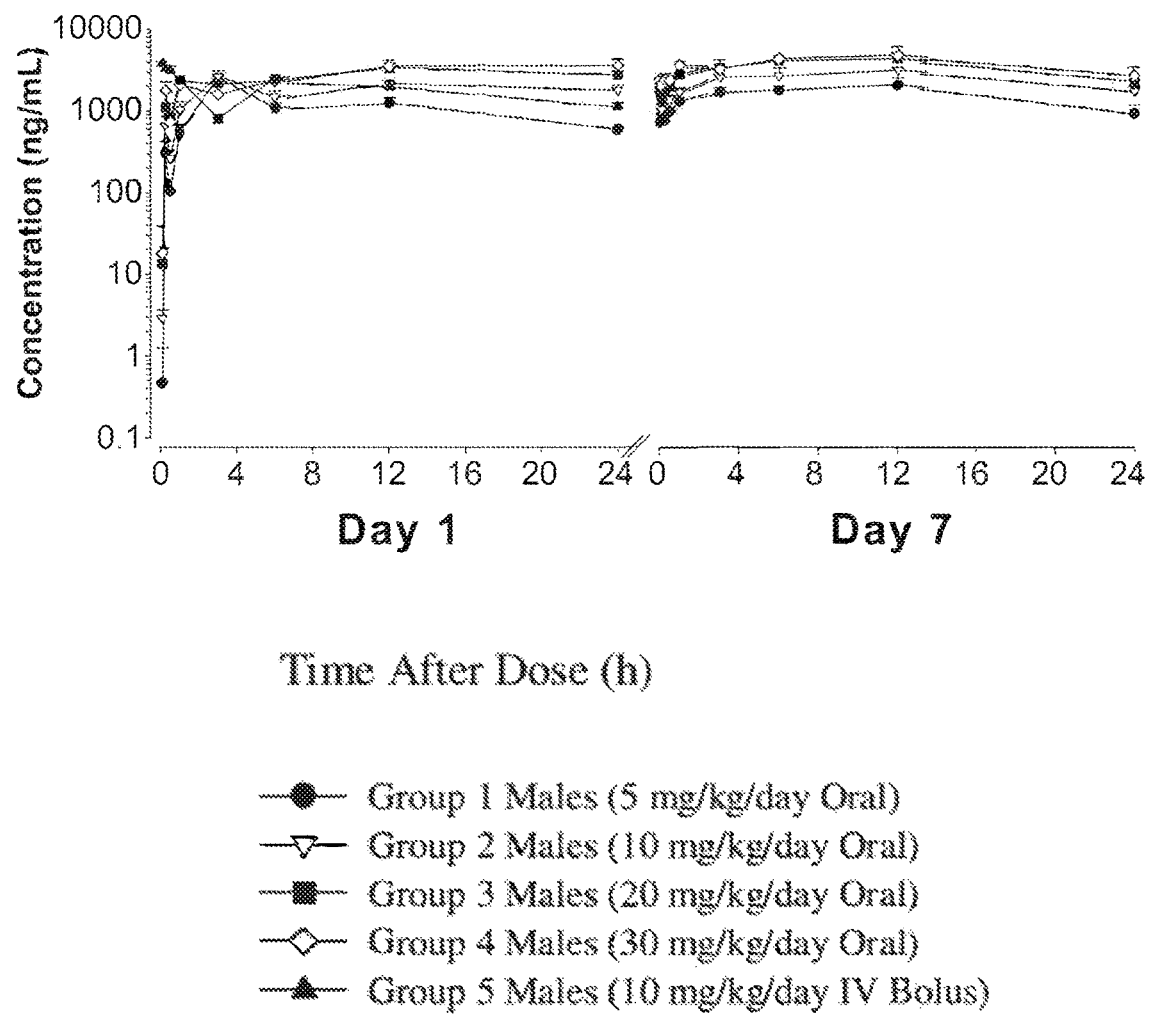

The concentration-time profile for each of 1065, 1002, and 1058 are shown in FIGS. 12A, 12B, and 12C, respectively. These graphs demonstrate that the terminal slopes of 1002 doses are much greater, i.e., shorter elimination half-life of 1002 (2.6 hours) than for 1065 (10.5 hours) as shown in Tables 8 and 9 for the iv dose. (Half-life of 1058 was not possible to calculate with this data, and so not reported.) Dose proportionally is also evident for 1065 and 1002 in FIG. 12, whereas 1058 concentrations were less dose proportional, as can be seen in $C_{max}$ and AUC values in Tables 8, 9, and 10 which should increase with dose. This saturation of effect can be seen in the DN $AUC_{0-24}$ (DN is dose normalized) values in Table 10 (1058) that decrease as dose increases (whereas these should be constant if dose proportionality is maintained), suggesting that higher doses will not increase blood levels of 1058 whereas 1065 blood concentrations can be increased further by increasing dose, if necessary, in order to achieve in vivo efficacy.

The area under the concentration-time curve from hour 0 to hour 24 ($AUC_{0-24}$) values of 1065 were much higher than those of 1002 and 1058. For example, even a small dose of 1 mg/kg of 1065 produced a significantly higher AUC of 7300 hr*ng/ml and 5 mg/kg produced around 35,000 hr*ng/ml. Only the 20 mg/kg dose of 1002 elicited an $AUC_0$-24 (37,000 hr*ng/ml) comparable to that of 5 mg/kg of 1065, whereas 20 mg/kg of 1058 produced around 64,100 hr*ng/ml or 37% decreased exposure at the same dose as 1065 (102,000 hr*ng/ml). The decreased exposure of 1058 relative to 1065 even at low doses and decreased dose proportionality for 1058 complicate the interpretation of dose response experiments and dose finding studies, and could lead to unpredictability of clinical efficacy.

These data clearly suggest that 1065 unexpectedly has superior pharmacokinetic properties such higher and more dose proportional AUC values, even when compared to compounds that are structurally similar compounds. Superior pharmacokinetics allow greater exposure of target organs or AR-dependent tumors to 1065 and help to rationalize its ability to achieve chemical castration at relatively low doses (whereas 1058 and 1002 failed to achieve castration at any dose), and improved anti-tumor properties.

TABLE 8

Summary of 1065 pharmacokinetic parameters

| Dose Group | Dose Level (mg/kg/day) | $C_0$ (ng/mL) | $C_{max}$ (ng/mL) | DN $C_{max}$ (ng/mL)/ (mg/kg/day) | $T_{max}$ (h) | $AUC_{0-t}$ (h * ng/mL) | $AUC_{0-24}$ (h * ng/mL) | DN $AUC_{0-24}$ (h * ng/mL)/ (mg/kg/day) | $AUC_{0-inf}$ (h * ng/mL) | $t_{1/2}$ (h) | CL (mL/h/kg) | Vss (mL/kg) |
|---|---|---|---|---|---|---|---|---|---|---|---|---|
| 1 | 1 | NA | 458 | 458 | 6.00 | 7300 | 7300 | 7300 | NA | NA | NA | NA |
| 2 | 5 | NA | 2220 | 443 | 6.00 | 34900 | 34900 | 6980 | NA | NA | NA | NA |
| 3 | 10 | NA | 3550 | 355 | 6.00 | 59500 | 59500 | 5950 | NA | NA | NA | NA |
| 4 | 20 | NA | 5550 | 278 | 6.00 | 102000 | 102000 | 5120 | NA | NA | NA | NA |
| 5 | 5 | 2510a | 2600 | 520 | 0.500 | 31800 | 31800 | 6360 | 40700 | 10.5 | 123 | 1860 |

TABLE 9

Summary of 1002 pharmacokinetic parameters

| Dose Group | Dose Level (mg/kg) | $C_0$ (ng/mL) | $C_{max}$ (ng/mL) | DN $C_{max}$ [(ng/mL)/ (mg/kg)] | $T_{max}$ (h) | $AUC_{0-t}$ (h * ng/mL) | $AUC_{0-24}$ (h * ng/mL) | DN $AUC_{0-24}$ [(h * ng/mL)/ (mg/kg)] | $AUC_{0-inf}$ (h * ng/mL) | $t_{1/2}$ (h) | CL (mL/hr/kg) | $V_{ss}$ (mL/kg) |
|---|---|---|---|---|---|---|---|---|---|---|---|---|
| 1 | 5 | NA | 526 | 105 | 1.00 | 6860 | 6860 | 1370 | 7050 | 4.87 | NA | NA |
| 2 | 20 | NA | 2620 | 131 | 6.00 | 37000 | 37000 | 1850 | NC | NC | NA | NA |
| 3 | 30 | NA | 3330 | 111 | 12.0 | 62000 | 62000 | 2070 | NC | NC | NA | NA |
| 4 | 60 | NA | 3800 | 63.3 | 1.00 | 77500 | 77500 | 1290 | NC | NC | NA | NA |
| 5 | 5 | 2460 | 2290 | 457 | 0.0830 | 9580 | 9580 | 1920 | 9600 | 2.62 | 521 | 2140 |

TABLE 10

Summary of 1058 pharmacokinetic parameters

| Dose Group | Dose Level (mg/kg/day) | $C_0$ (ng/mL) | $C_{max}$ (ng/mL) | DN $C_{max}$ [(ng/mL)/ (mg/kg/day)] | $T_{max}$ (h) | $AUC_{0-t}$ (h * ng/mL) | $AUC_{0-24}$ (h * ng/mL) | DN $AUC_{0-24}$ [(h * ng/mL)/ (mg/kg/day)] |
|---|---|---|---|---|---|---|---|---|
| 1 | 5 | NA | 2570 | 515 | 3.00 | 26800 | 26800 | 5350 |
| 2 | 10 | NA | 2680 | 268 | 3.00 | 44600 | 44600 | 4460 |
| 3 | 20 | NA | 3420 | 171 | 12.0 | 64100 | 64100 | 3200 |
| 4 | 30 | NA | 3650 | 122 | 24.0 | 71500 | 71500 | 2380 |
| 5 | 10 | 4200 | 3940 | 394 | 0.083 | 45500 | 45500 | 4550 |

| Parameters | Definition |
|---|---|
| $C_0$ | Back-extrapolated concentration at time 0 (Group 5 only). |
| $C_{max}$ | Maximum observed concentration. |
| $T_{max}$ | Time of maximum observed concentration. |
| $AUC_{0-t}$ | Area under the concentration-time curve from hour 0 to the last measurable concentration, estimated by the linear trapezoidal rule. |
| $AUC_{0-24}$ | Area under the concentration-time curve from hour 0 to hour 24, estimated by the linear trapezoidal rule. |
| $AUC_{0-inf}$ | Area under the concentration-time curve from hour 0 to infinity for Day 1, calculated as follows: $AUC_{0-inf} = AUC_{0-t} + C_t/\lambda_z$ Where $C_t$ is the last measurable concentration and $\lambda_z$ is the elimination rate constant estimated using log-linear regression during the terminal elimination phase. |
| $t_{1/2}$ | Elimination half-life, determined by $\ln(2)/\lambda_z$. |
| CL | Clearance, calculated as Dose/$AUC_{0-inf}$ on Day 1. |
| $V_{ss}$ | Volume of distribution at steady-state, calculated as CL * $MRT_{0-inf}$ (Group 5 only). |
| F | Bioavailability, calculated as; [[$AUC_{0-24}$ Oral]/[$AUC_{0-24}$ IV]] * [[Dose IV]/[Dose Oral]] |
| AR | Accumulation ratio, calculated as: [$C_{max}$ or $AUC_{0-24}$ [Day X]]/[$C_{max}$ or $AUC_{0-24}$ [Day X]]. |
| DN $C_{max}$ | Dose normalized $C_{max}$, calculated as $C_{max}$/dose level. |
| DN $AUC_{0-24}$ | Dose normalized $AUC_{0-24}$, calculated as $AUC_{0-24}$/dose level. |

Example 9

Inhibition of Enzalutamide-Resistant Cancer

Materials and Methods:

Male Sprague Dawley Rag2−/−; Il2rg−/− (SRG) rats were housed in group of three rats/cage. They were provided with food and water ad libitum and were maintained in a 12 hour light/dark cycle.

Cell Culture and Preparation:

MDVR (enzalutamide-resistant VCaP prostate cancer cells) cells were thawed and expanded according to recommendations by ATCC and in the presence of enzalutamide at 1 µM to maintain selection for enzalutamide-resistant cells.

Animal Preparation:

Cell inoculations were carried out in a Class II/A2 biosafety cabinet. The surgical space was cleaned with Clidox® and sterile drapes were placed on the surface. The animals were anesthetized using inhaled isoflurane. Prior to injection, the hind flank was shaved and cleaned with alcohol prep pads. Animals were placed back in their home cage and monitored until they recovered and sternal recumbency was observed.

Cell inoculation: All animals were inoculated with a total volume of 500 µL subcutaneously in the left hind flank. The inoculation suspension consisted of 250 µL of cell suspension mixed with 250 µL of Matrigel, diluted to 10 mg/mL working solution with DMEM, which was mixed on ice immediately by pipetting the cells into the Matrigel using a p1000 micropipette fitted with a sterile aerosol resistant tip prior to injection. The final concentration of Matrigel was 5 mg/mL. Cells were injected using a sterile 1 mL tuberculin syringe fitted with a 27 G ½ inch needle. Each needle/syringe was used for only 1 animal.

Test Article Preparation:

Vehicle was prepared by mixing 20% DMSO in PEG400 in a biosafety cabinet using sterile reagents and consumables.

SARDs were dissolved at 5-, 10-, or 15 mg/mL in vehicle in a biosafety cabinet using sterile reagents and consumables.

All were produced in bulk, from which aliquots were made for daily use in sterile glass amber vials. Aliquots were stored at −20° C., thawed immediately prior to dosing. Excess material was discarded per approved waste disposal guidelines.

Dosing:

Vehicle:

Animals in the vehicle control group were dosed by oral gavage daily for 30 consecutive days with flexible 16-gauge gavage tubes with 20% DMSO in PEG400 (Lot number maintained in the raw data file) at 2 mL/kg.

SARDs:

Animals in treatment groups were dosed by oral gavage daily for 30 consecutive days with flexible 16-gauge gavage tubes with 2 mL/kg, resulting in dosages of 10-, 20-, or 30 mg/kg of 1002 or 10 mg/kg of 1058 or 1065 dissolved in vehicle.

Statistics:

One-way ANOVA and Tukey's post-hoc test were used to compare the difference in percent change in body weight among treatment groups. Overall percent change in body weight from treatment initiation to termination was used for this analysis. One-way ANOVA followed by Tukey's test was used to determine statistical significance in tumor volume, percent change in tumor volume, and tumor weight between treatment groups.

Figure 14A:
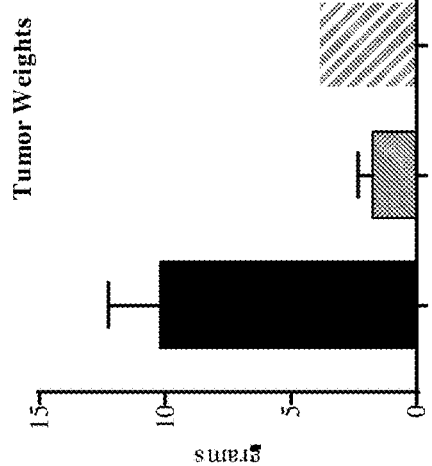
FIGS. 14A, 14B, and 14C present the comparative xenograft efficacy of 1065, 1058 and 1002 in a model of enzalutamide resistance (MDV resistant VCaP cells or MDVR).
Figure 14B:
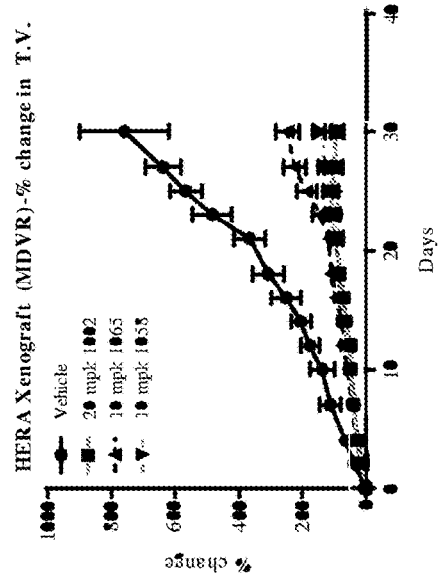
Figure 14C:
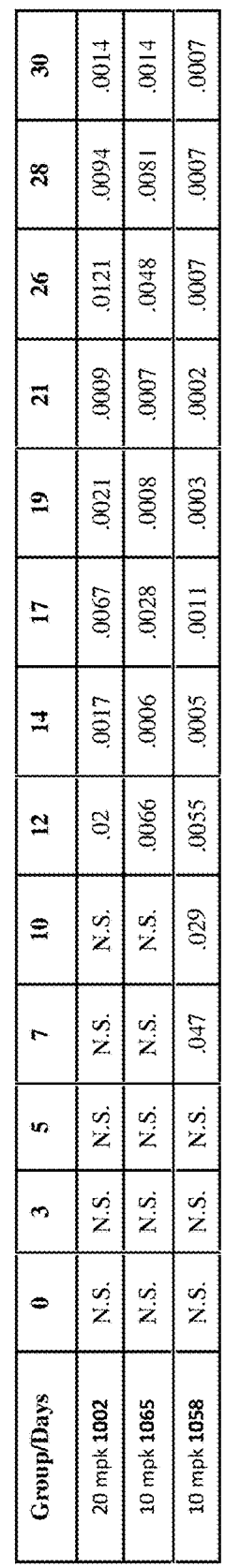

Results:

1002 inhibited the tumor growth statistically significantly at 20 and 30 mg/kg (G3 and G4 in FIGS. 13A-13C), while 10 mg/kg produced 30-40% tumor growth inhibition but failed to show statistically significant effect (see G2 in FIGS. 13A-13C). A comparison of 20 mg/kg of 1002 with 10 mg/kg of 1058 and 1065, as shown in FIGS. 14A-14C, produced comparable results between the three groups, indicating that 1065 is approximately two fold more potent than 1002 in inhibiting the enzalutamide-resistant prostate cancer. In a further in vivo experiment, rats were castrated and AR-dependent tissues were allowed to atrophy for 7 days followed by treatment at 20 mg/kg with enobosarm or 1065, 1058, or 1002 for 13 days (FIGS. 15A-15C). This experiment demonstrated that all three SARD were not able to act as agonists in ventral prostate (VP) or seminal vesicles (SV) but rather behaved similar to castrated vehicle group, whereas enobosarm (a nonsteroidal, anabolic tissue selective AR agonist) was a partial agonist supporting both SV and VP re-growth (~50-60% of intact vehicle). This establishes that the SARDs of this invention do not possess any intrinsic agonist activity in vivo even at dose higher than necessary for in vivo efficacy.

Example 10

SARD Cross-Reactivity Profile

Cross-Reactivity Profiling

Methods:

Compounds 1002, 1058, and 1065 were tested by a third party (DiscoveRx) to produce cross-reactivity profiles for each compound with regard to kinases (kinome) and G-protein coupled receptors (GCPR). Profiles consisted of >450 kinases and >160 GCPR's.

Kinomescan™ Screening:

Cross-reactivity is defined as <50% of Percent of Control, as shown in the Tables 11-13. Screening methodology for the kinase assays follows: The KINOMEscan™ screening platform employs a novel and proprietary active site-directed competition binding assay to quantitatively measure interactions between test compounds and more than 450 human kinases and disease relevant mutant variants. This robust and reliable assay technology affords investigators the ability to extensively annotate compounds with accurate, precise and reproducible data. KINOMEscan™ assays do not require ATP and thereby report true thermodynamic interaction affinities, as opposed to $IC_{50}$ values, which can depend on the ATP concentration.

Compounds that bind the kinase active site and directly (sterically) or indirectly (allosterically) prevent kinase binding to the immobilized ligand, will reduce the amount of kinase captured on the solid support. Conversely, test molecules that do not bind the kinase have no effect on the amount of kinase captured on the solid support. Screening "hits" are identified by measuring the amount of kinase captured in test versus control samples by using a quantitative, precise and ultra-sensitive qPCR method that detects the associated DNA label. In a similar manner, dissociation constants (Kds) for test compound-kinase interactions are calculated by measuring the amount of kinase captured on the solid support as a function of the test compound concentration.

For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Percent Control (% Ctrl):

The compound(s) were screened at the concentration(s) requested, and results for primary screen binding interactions are reported as '% Ctrl', where lower numbers indicate stronger hits in the matrix, as summarized in the Tables 11-13 The Percent Control calculation is [test compound signal−positive control signal/negative control signal−positive control signal]×100; where test compound is the SARD of this invention, negative control is DMSO (100% Ctrl), and positive control is a control compound (0% Ctrl).

Cross-Reactivity Profile—gcprMAX Panel

Goal: Antagonist Primary Screen of G-Couple Protein Receptors (GCPR's)

Methods.

The assays were performed utilizing the PathHunter beta-arrestin enzyme fragment complementation (EFC) technology.

Technology Principle:

The PathHunter® β-Arrestin assay monitors the activation of a GPCR in a homogenous, non-imaging assay format using a technology developed by DiscoveRx called Enzyme Fragment Complementation (EFC) with β-galactosidase (β-Gal) as the functional reporter. The enzyme is split into two inactive complementary portions (EA for Enzyme Acceptor and ED for Enzyme Donor) expressed as fusion proteins in the cell. EA is fused to β-Arrestin and ED is fused to the GPCR of interest. When the GPCR is activated and β-Arrestin is recruited to the receptor, ED and EA complementation occurs, restoring β-Gal activity which is measured using chemiluminescent PathHunter® Detection Reagents.

Assay Design: GPCR Arrestin: Cell Handling.

PathHunter cell lines were expanded from freezer. Cells were seeded in a total volume of 20 μL into white walled, 384-well microplates and incubated at 37° C. for the appropriate time prior to testing.

Antagonist Format.

For antagonist determination, cells were pre-incubated with antagonist followed by agonist challenge at the $EC_{80}$ concentration. Intermediate dilution of sample stocks was performed to generate 5× sample in assay buffer. 5 μL of 5× sample was added to cells and incubated at 37° C. or room temperature for 30 minutes. Vehicle concentration was 1%. 5 μL of 6×$EC_{80}$ agonist in assay buffer was added to the cells and incubated at 37° C. or room temperature for 90 or 180 minutes.

Signal Detection.

Assay signal was generated through a single addition of 12.5 or 15 μL (50% v/v) of PathHunter Detection reagent cocktail, followed by a one hour incubation at room temperature. Microplates were read following signal generation with a PerkinElmer Envision™ instrument for chemiluminescent signal detection.

Data Analysis.

Compound activity was analyzed using CBIS data analysis suite (ChemInnovation, CA). For antagonist mode assays, percentage inhibition was calculated using the following formula: % Inhibition=100%×(1−(mean RLU of test sample−mean RLU of vehicle control)/(mean RLU of $EC_{80}$ control−mean RLU of vehicle control) [where RLU is relative light unit]).

Results.

While 1065 showed the least cross-reactivity among the three compounds to kinases and GPCRs, 1058 showed the most cross-reactivity of the three compounds. Tables 11, 12, and 13 respectively specify which kinases are bound by 1065, 1002, and 1058. As can be seen in Table 13, 1058 has greater liability due to kinase cross-reactivity as it reacted with 15 different kinases in panel of >460 kinases and mutants, including very potent % inhibition of ROCK, whereas 1065 (Table 11) and 1002 (Table 12) only interacted with 2 or 3 kinases, respectively, and not ROCK.

TABLE 11

List of kinases bound by 1065

| Compound Name | DiscoveRx Gene Symbol | Entrez Gene Symbol | Percent Control |
|---|---|---|---|
| 1065 | GSK3A | GSK3A | 6.4 |
| 1065 | MYLK | MYLK | 45 |

TABLE 12

List of kinases bound by 1002

| Compound Name | DiscoveRx Gene Symbol | Entrez Gene Symbol | Percent Control |
|---|---|---|---|
| 1002 | CLK4 | CLK4 | 17 |
| 1002 | CLK1 | CLK1 | 27 |
| 1002 | MKNK2 | MKNK2 | 47 |

TABLE 13

List of kinases bound by 1058

| Compound Name | DiscoveRx Gene Symbol | Entrez Gene Symbol | Percent Control |
|---|---|---|---|
| 1058 | ROCK1 | ROCK1 | 3.1 |
| 1058 | ROCK2 | ROCK2 | 3.9 |
| 1058 | CLK4 | CLK4 | 8.1 |
| 1058 | CLK1 | CLK1 | 13 |
| 1058 | CDK7 | CDK7 | 28 |
| 1058 | CLK2 | CLK2 | 36 |
| 1058 | STK39 | STK39 | 37 |
| 1058 | SGK2 | SGK2 | 39 |
| 1058 | SGK | SGK1 | 44 |
| 1058 | BMPR1B | BMPR1B | 47 |
| 1058 | MKNK2 | MKNK2 | 47 |
| 1058 | PKAC-alpha | PRKACA | 47 |
| 1058 | DYRK1B | DYRK1B | 48 |
| 1058 | MYLK | MYLK | 48 |
| 1058 | PIM2 | PIM2 | 48 |

With regard to GCPR screening, 1058 again demonstrated more liability due to cross-reactivity as it inhibited three GPCR's, as listed in Table 14, whereas no GPCR was inhibited by 50% by 1065 and 1002. Unexpectedly, 1065 demonstrated a relative lack of liability due to cross-reactivity with various kinases and GCPR's. A person skilled in the art of compound screening would not have expected 1065 to possess less off-target liabilities based on the minor structural differences between 1065 and 1002 & 1058.

TABLE 14

List of G-protein coupled receptors antagonized by 1058

| GPCR ID | Compound ID | Assay Mode | Conc (μM) | % Inhibition |
|---|---|---|---|---|
| ADRA2B | 1058 | Antagonist | 10 | 48% |
| FSHR | 1058 | Antagonist | 10 | 50% |
| MLNR | 1058 | Antagonist | 10 | 52% |

The SARDs were tested for cross-reactivity with GPCRs and kinases, at DiscoveRx according to their protocols (described above).
Results:
No GPCR was inhibited by >50% by 1065 and 1002. While 1065 showed the least cross-reactivity among the three compounds to kinases and GPCRs, 1058 showed the most cross-reactivity of the three compounds.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A selective androgen receptor degrader (SARD) compound, optical isomer, or any mixture of optical isomers, pharmaceutically acceptable salt, pharmaceutical product, hydrate or any combination thereof, wherein said SARD compound is represented by a compound of the following structures:

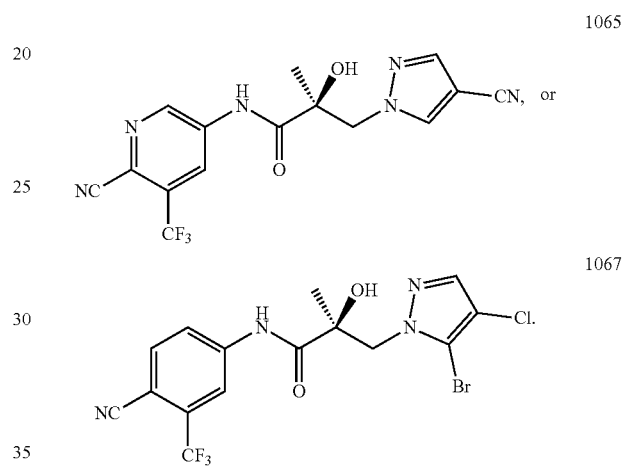

2. The compound according to claim 1, wherein the compound exhibits at least one of binding to the androgen receptor (AR) through an alternate binding domain in the N-terminal domain (NTD), AR antagonism in vivo of an AR target organ, AR-splice variant (AR-SV) degradation activity, AR-full length (AR-FL) degradation activity, AR-SV inhibitory, AR-FL inhibitory activity, or AR antagonism in vivo of an AR target organ.

3. A pharmaceutical composition comprising a SARD compound according to claim 1, optical isomer, or any mixture of optical isomers, pharmaceutically acceptable salt, pharmaceutical product, hydrate or any combination thereof, and a pharmaceutically acceptable carrier.

4. The pharmaceutical composition according to claim 3, wherein the pharmaceutical composition is formulated for topical use or for oral use.

5. A method of treating prostate cancer (PCa) or increasing the survival of a male subject suffering from prostate cancer comprising administering to the male subject a therapeutically effective amount of a SARD compound according to claim 1, optical isomer, or any mixture of optical isomers, pharmaceutically acceptable salt, pharmaceutical product, hydrate or any combination thereof.

6. The method according to claim 5, wherein the prostate cancer is at least one of advanced prostate cancer, refractory prostate cancer, castration resistant prostate cancer (CRPC), metastatic CRPC (mCRPC), non-metastatic CRPC (nmCRPC), or high-risk nmCRPC.

7. The method according to claim 5 further comprising administering androgen deprivation therapy (ADT).

8. The method according to claim 5, wherein the prostate cancer is resistant to treatment with an androgen receptor antagonist.

9. The method according to claim 8, wherein the androgen receptor antagonist is at least one of enzalutamide, apalutamide, bicalutamide, abiraterone, ODM-201 [darolutamide], EPI-001, EPI-506, AZD-3514, galeterone, ASC-J9, flutamide, hydroxyflutamide, nilutamide, cyproterone acetate, ketoconazole, or spironolactone.

10. A method of treating enzalutamide resistant prostate cancer, apalutamide resistant prostate cancer, or abiraterone resistant prostate cancer in a subject comprising administering to the subject a therapeutically effective amount of a SARD compound according to claim 1, optical isomer, or any mixture of optical isomers, pharmaceutically acceptable salt, pharmaceutical product, hydrate or any combination thereof.

11. A method of treating triple negative breast cancer in a subject comprising administering to the subject a therapeutically effective amount of a SARD compound according to claim 1, optical isomer, or any mixture of optical isomers, pharmaceutically acceptable salt, pharmaceutical product, hydrate or any combination thereof.

12. A method of reducing the levels of AR-splice variants in a subject comprising administering to the subject a therapeutically effective amount of a SARD compound according to claim 1, optical isomer, or any mixture of optical isomers, pharmaceutically acceptable salt, pharmaceutical product, hydrate or any combination thereof.

13. The method according to claim 12, wherein the method further reduces the levels of AR-full length (AR-FL) in the subject.

14. A method of treating Kennedy's disease, acne, hirsutism, alopecia, a hormonal condition in a female, sexual perversion, hypersexuality, paraphilias, androgen psychosis, virilization, androgen insensitivity syndrome, an AR-expressing cancer, amyotrophic lateral sclerosis (ALS), uterine fibroids, abdominal aortic aneurysm (AAA), or hormonal condition in a male, decreasing sebum production, increasing or modulating ovulation, or reducing the levels of polyglutamine (polyO) AR polymorphs in a subject comprising administering to the subject a therapeutically effective amount of the SARD compound of claim 1, optical isomer, or any mixture of optical isomers, pharmaceutically acceptable salt, pharmaceutical product, hydrate or any combination thereof.

15. The method according to claim 14, wherein the hormonal condition in a female is at least one of precocious puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, or vaginal dryness.

16. The method according to claim 14, wherein the AR-expressing cancer is at least one of breast cancer, testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer.

17. The method according to claim 16, wherein the breast cancer is triple negative breast cancer.

18. The method according to claim 14, wherein the polyQ-AR polymorphs is a short polyQ polymorph and the method further treats dermal disease.

19. The method according to claim 14, wherein the polyQ-AR polymorphs is a long polyQ polymorph and the method further treats Kennedy's disease.

20. The method of according to claim 14, wherein said hormonal condition in a male is hypergonadism, hypersexuality, sexual dysfunction, gynecomastia, precocious puberty in a male, alterations in cognition and mood, depression, hair loss, hyperandrogenic dermatological disorders, precancerous lesions of the prostate, benign prostate hyperplasia, prostate cancer and/or other androgen-dependent cancers.

21. The compound of claim 1, wherein said SARD compound is

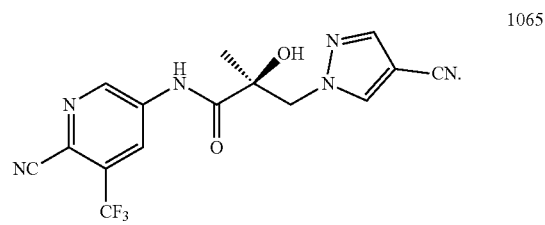 [SMILES: C[C@](O)(Cn1cc(C#N)cn1)C(=O)Nc1cnc(C#N)c(C(F)(F)F)c1]

1065

22. The compound according to claim 21, wherein the compound exhibits at least one of binding to the androgen receptor (AR) through an alternate binding domain in the N-terminal domain (NTD), AR antagonism in vivo of an AR target organ, AR-splice variant (AR-SV) degradation activity, AR-full length (AR-FL) degradation activity, AR-SV inhibitory, AR-FL inhibitory activity, or AR antagonism in vivo of an AR target organ.

23. A method of treating prostate cancer (PCa) or increasing the survival of a male subject suffering from prostate cancer comprising administering to the subject a therapeutically effective amount of a compound according to SARD claim 21, optical isomer, or any mixture of optical isomers, pharmaceutically acceptable salt, pharmaceutical product, hydrate or any combination thereof.

24. The method according to claim 23, wherein the prostate cancer is at least one of advanced prostate cancer, refractory prostate cancer, castration resistant prostate cancer (CRPC), metastatic CRPC (mCRPC), non-metastatic CRPC (nmCRPC), or high-risk nmCRPC.

25. The method according to claim 24, further comprising administering androgen deprivation therapy (ADT).

26. The method according to claim 24, wherein the prostate cancer is resistant to treatment with an androgen receptor antagonist(s).

27. The method according to claim 26, wherein the androgen receptor antagonist is at least one of enzalutamide, apalutamide, bicalutamide, abiraterone, ODM-201 [darolutamide], EPI-001, EPI-506, AZD-3514, galeterone, ASC-J9, flutamide, hydroxyflutamide, nilutamide, cyproterone acetate, ketoconazole, or spironolactone.

* * * * *